US008642295B2

(12) United States Patent
De Laat et al.

(10) Patent No.: US 8,642,295 B2
(45) Date of Patent: *Feb. 4, 2014

(54) CIRCULAR CHROMOSOME CONFORMATION CAPTURE (4C)

(75) Inventors: Wouter De Laat, Rotterdam (NL); Frank Grosveld, Rotterdam (NL)

(73) Assignee: Erasmus University Medical Center (NL)

( * ) Notice: Subject to any disclaimer, the term of this patent is extended or adjusted under 35 U.S.C. 154(b) by 515 days.

This patent is subject to a terminal disclaimer.

(21) Appl. No.: 12/522,555

(22) PCT Filed: Jan. 10, 2008

(86) PCT No.: PCT/IB2008/000625
§ 371 (c)(1),
(2), (4) Date: Jul. 9, 2009

(87) PCT Pub. No.: WO2008/084405
PCT Pub. Date: Jul. 17, 2008

(65) Prior Publication Data
US 2010/0062947 A1  Mar. 11, 2010

Related U.S. Application Data

(60) Provisional application No. 60/999,750, filed on Jan. 11, 2007, provisional application No. 60/977,900, filed on Oct. 5, 2007.

(51) Int. Cl.
*C12P 19/34* (2006.01)

(52) U.S. Cl.
USPC ........................................... 435/91.2

(58) Field of Classification Search
USPC ........................................... 435/91.2
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,683,195 A | 7/1987 | Mullis et al. |
| 4,683,202 A | 7/1987 | Mullis |
| 4,965,188 A | 10/1990 | Mullis et al. |
| 5,143,854 A | 9/1992 | Pirrung et al. |
| 5,571,639 A | 11/1996 | Hubbell et al. |
| 5,593,839 A | 1/1997 | Hubbell et al. |
| 5,837,832 A | 11/1998 | Chee et al. |
| 2005/0130161 A1 | 6/2005 | Fraser et al. |

FOREIGN PATENT DOCUMENTS

| | | |
|---|---|---|
| EP | 0 239 400 A2 | 9/1987 |
| EP | 0 717 113 A2 | 6/1996 |
| EP | 0 728 520 A1 | 8/1996 |
| WO | WO 90/15070 A1 | 12/1990 |
| WO | WO 92/10092 A1 | 6/1992 |
| WO | WO 93/09668 A1 | 5/1993 |
| WO | WO 95/11995 A1 | 5/1995 |
| WO | WO 97/29212 A1 | 8/1997 |
| WO | WO 98/09985 A2 | 3/1998 |
| WO | 2007/004057 A2 | 1/2007 |
| WO | WO 2007/004057 A2 | 1/2007 |

OTHER PUBLICATIONS

Simonis Marieke et al., "Nuclear organization of active and inactive chromatin domains uncovered by chromosome conformation capture-on-chip (4C)", Nature Genetics, 38(11):1348-1354 (2006).
Zhao Zhihu et al., "Circular chromosome conformation capture (4C) uncovers extensive networks of epigenetically regulated intra- and interchromosomal interactions", Nature Genetics, 38(11):1341-1347 (2006).
Wurtele Hugo et al., "Genome-wide scanning of HoxB1-associated loci in mouse ES cells using an open-ended Chromosome Conformation Capture methodology", Chromosome Research: An International Journal on the Molecuar, Supramolecular and Evolutionary Aspects of Chromosome Biology, 14(5):477-495 (2006).
Ohlsson Rolf et al., "The 4C technique: the 'Rosetta stone' for genome biology in 3D", Current Opinion in Cell Biology, 19(3):321-325 (2007).
De Laat Wouter, "Long-range DNA contacts: romance in the nucleus?", Current Opinion in Cell Biology, 19(3):317-320 (2007).
Dekker J. et al., "Capturing chromosome conformation", Science, 295(5558):1306-1311 (2002).
Hacia J.G., "Resequencing and mutational analysis using oligonucleotide microarrays", Nature Genetics, 21 (Suppl):42-47 (1999).
Search Report for co-pending PCT/IB2008/000625 listing relevant art cited by the International Searching Authority, Dec. 22, 2008.
Afshari, C.A. et al., Cancer Research, 1999, vol. 59, No. 19, p. 4759-4760.
Aoyama, M. et al., Cancer Research, Jun. 1, 2005, vol. 65, No. 11, p. 4587-4597.
Barany, "The Ligase Chain Reaction in a PCR World", Genome Research, 1991, vol. 1, p. 5-16.
Blanton J, Gaszner M, Schedl P., Protein: protein interactions and the pairing of boundary elements in vivo. Genes Dev., 2003,17:664-75.

(Continued)

*Primary Examiner* — Cynthia B Wilder
(74) *Attorney, Agent, or Firm* — McKee, Voorhees & Sease, P.L.C.

(57) ABSTRACT

The present invention relates in one aspect to a method for analyzing the frequency of interaction of a target nucleotide sequence with one or more nucleotide sequences of interest (eg. one or more genomic loci) comprising the steps of: (a) providing a sample of cross-linked DNA; (b) digesting the cross-linked DNA with a primary restriction enzyme; (c) ligating the cross-linked nucleotide sequences; (d) reversing the cross linking; (e) optionally digesting the nucleotide sequences with a secondary restriction enzyme; (f) optionally ligating one or more DNA sequences of known nucleotide composition to the available secondary restriction enzyme digestion site(s) that flank the one or more nucleotide sequences of interest; (g) amplifying the one or more nucleotide sequences of interest using at least two oligonucleotide primers, wherein each primer hybridises to the DNA sequences that flank the nucleotide sequences of interest; (h) hybridising the amplified sequence(s) to an array; and (i) determining the frequency of interaction between the DNA sequences.

49 Claims, 41 Drawing Sheets

(56) References Cited

OTHER PUBLICATIONS

Branco M.R. & Pombo A., PLoS Biol., 2006, vol. 4, e138.
Brown J. M. et al., Journal of Cell Biology,. 2006, vol. 172, p. 177-187.
Burnett R. C. , M. J. Thirman, J. D. Rowley, M. O. Diaz, Blood, 84, 1232-6 (Aug. 15, 1994).
Cahill P., Foster K. and Mahan D.E., Clin. Chem., 1991, vol. 37, No. 9, p. 1482-1485.
Carter D. et al., "Long-range chromatin regulatory interactions in vivo", Nature Genetic, 2002, vol. 32, No. 4, p. 623-626.
Celis J.E. et al., FEBS Letters, 2000, vol. 48, No. 1, p. 2-16.
Chubb J.R. et al., Current Biology, 2002, vol. 12, p. 439-445.
Dekker J. et al., "Capturing chromosome conformation," Science, 2002, vol. 295, No. 5558, p. 1306-1311. XP02301470.
Drissen R, Palstra RJ, Gillemans N, Splinter E, Grosveld F, Philipsen S, de Laat W., The active spatial organization of the beta-globin locus requires the transcription factor EKLF, Genes Development, 2004, vol. 18, p. 2485-2490.
Easton D. F. et al., Nature, Jun. 28, 2007 vol. 447, No. 7148, p. 1087-1093.
Eichler E.E. et al., "Completing the map of human genetic variation", Nature, May 10, 2007, vol. 447, p. 161-165.
Essers J. et al., Molecular Biology of the Cell, 2005, vol. 16, p. 769-775.
Gerlich D. et al., Cell, 2003, vol. 112, p. 751-764.
Gilbert N. et al., Cell, 2004, vol. 118, p. 555-566.
Horike S., Cai S., Miyano M., Cheng J.F., Kohwi-Shigematsu T., Loss of silent-chromatin looping and impaired imprinting mprinting of DLX5 in Rett syndrome, Nature Genetics, 2004, vol. 37, p. 31-40.
Iafrate A. J. et al., "Detection of large-scale variation in the human genome", Nature Genetics, Sep. 2004, vol. 36, No. 9, p. 949-951.
Khan J. et al., "Expression profiling in cancer using cDNA microarrays", Electrophoresis, 1999, vol. 20, No. 2, p. 223-229.
Landegren et al., "DNA Diagnostics—Molecular Techniques and Automation", Science, 1988, p. 229.
Ling J.Q. et al., Science, Apr. 14, 2006, vol. 312, p. 269-272.
Lockhart D.J. and Winzeler E.A., Nature, 2000, vol. 405, No. 6788, p. 827-826.
Lomvardas S. et al., Cell, Jul. 28, 2006, vol. 126, p. 403-413.
Mehan M. R., N. B. Freimer, R. A. Ophoff, "A genome-wide survey of segmental duplications that mediate common human genetic variation of the chromosal architecture", Human Genomics, Aug. 2004, vol. 1, No. 5, p. 335-344.
Murrell A, Heeson S, Reik W. 2004. Interaction between differentially methylated regions partitions the imprinted genes Igf2 and H19 into parent-specific chromatin loops. Nat Genet 36:889-93.
Ochman H. et al., Genetics, 1988, vol. 120, No. 3, p. 621-623.
Palstra, R.J., Tolhuis, B., Splinter, E., Nijmeijer, R., Grosveld, F., and de Laat, W., The beta-globin nuclear compartment in development and erythroid differentiation, Nature Genetics, 2003, vol. 35, No. 2, p. 190-194.
Patrinos, G.P., de Krom, M., de Boer, E., Langeveld, A., Imam, A.M.A, Strouboulis, J., de Laat, W., and Grosveld, F. G., Multiple interactions between regulatory regions are required to stabilize an active chromatin hub. Genes & Development, 2004, vol. 18, p. 1495-1509.
Rippe K. et al., Trends in Biochemical Sciences, 2001, vol. 26, No. 12, p. 733-740.
Ross et al., "Systematic variation in gene expression patterns in human cancer cell lines", Nature Genetics, Mar. 2000, vol. 24, No. 3, p. 227-235.
Shalon D. et al., Genome Research, 1996, vol. 6, No. 7, p. 639-645.
Sharp A. J. , Z. Cheng, E. E. Eichler, "Structural Variation of the Human Genome", Annual Review of Genomics and Human Genetics, 2006, vol. 7, 407-442.
Shykind B., Human Molecular Genetics, 2005, vol. 14, Spec. No. 1, R33-R39.
Soulier J. et al., Blood, Jul. 1, 2005, vol. 106, p. 274-286.
Speleman F. et al., "A new recurrent inversion, inv(7)(P15q34), leads to transcriptional activation of HOXA10 and HOXA11 in a subset of T-cell acute lympoblastic leukemias", Leukemia, Mar. 2005, vol. 19, p. 358-366.
Spilianakis C.G., Flavell R.A., Long-range intrachromosomal interactions in the T helper type 2 cytokine locus, Nature Immunology, 2004, vol. 5, No. 5, p. 1017-27.
Splinter E. et al., Methods in Enzymology, 2004, vol. 375, p. 493-507.
Tolhuis, B., Palstra, R.J., Splinter, E., Grosveld, F., and de Laat, W., Looping and interaction between hypersensitive sites in the active beta-globin locus, Molecular Cell, 2002, vol. 10, p. 1453-1465.
Tuzun E. et al., "Fine-scale structural variation of the human genome", Nature Genetics, Jul. 2005, vol. 37, p. 727-732.
Vakoc CR, Letting DL, Gheldof N, Sawado T, Bender MA, Groudine M, Weiss MJ, Dekker J, Blobel GA., Proximity among distant regulatory elements at the beta-globin locus requires GATA-1 and FOG-1, Molecular Cell, 2005, vol. 17, p. 453-462.
Vlierberghe P. van et al., Leukemia, Jul. 2006, vol. 20, p. 1245-1253.
Wang D.G. et al., Science, 1998, vol. 280, No. 5366, p. 1077-1082.
Wellcome Trust Case Control Consortium, Nature (Jun. 7, 2007) vol. 447, p. 661-678.
Winter G. and Milstein C., Nature, 1991, vol. 349, p. 293-299.

B-globin

HS2

Sequence over breakpoint:
AAGGAAACCCCATGCCCATAAGACGTCACTAATTTCTGAACTCTTGTTTTTTTTTTTTTTTTT
CAAGTAGTTCTCATCTAAGTAGTTGTTTTTTGTCATGAGAAAATCAGATATGTTGCTAAAAATTCACAA
CTATTGCAAGAAAAAATAAAAGAC Sequenced breakpoint #2:
CTCCAATGTAACTGTGGATTACACCTAAAAGAGCCAGAAAACACAGACTC
TCTGTGGAACCATGACACAACAGTGCTTGGTATTATTTTTTCCTAGTTAG NB. Adapters at each end of the PCR product can be the same or can be different

CIRCULAR CHROMOSOME CONFORMATION CAPTURE (4C)

FIELD OF INVENTION

The present invention relates to the analysis of the frequency of interaction of two or more nucleotide sequences in the nuclear space. Changes in interactions are used as a tool to detect genome rearrangements for diagnostics and prognostics.

BACKGROUND TO THE INVENTION

Studies on mammalian nuclear architecture aim to understand how 2 meters of DNA is folded into a nucleus of 10 μm across, while allowing accurate expression of the genes that specify the cell-type, and how this is faithfully propagated during each cell cycle. Progress in this field has largely come from microscopy studies, which revealed that genomes are non-randomly arranged in the nuclear space. For example, densely packed heterochromatin is separated from more open euchromatin and chromosomes occupy distinct territories in the nuclear space 2. An intricate relationship exists between nuclear positioning and transcriptional activity. Although transcription occurs throughout the nuclear interior, active genes that cluster on chromosomes preferentially locate at the edge or outside of their chromosome territory. Individual genes may migrate upon changes in their transcription status, as measured against relatively large nuclear landmarks such as chromosome territories, centromeres or the nuclear periphery. Moreover, actively transcribed genes tens of megabases apart on the chromosome can come together in the nucleus, as demonstrated recently by fluorescence in situ hybridization (FISH) for the β-globin locus and a few, selected, other genes. Besides transcription, genomic organisation is associated with the coordination of replication, recombination and the probability of loci to translocate (which can lead to malignancies) and the setting and resetting of epigenetic programs. Based on these observations it is thought that the architectural organisation of DNA in the cell nucleus is a key contributor to genomic function.

Different assays have been developed to allow an insight into the spatial organisation of genomic loci in vivo. One assay, called RNA-TRAP has been developed (Carter et al. (2002) *Nat. Genet.* 32, 623) which involves targeting of horseradish peroxidase (HRP) to nascent RNA transcripts, followed by quantitation of HRP-catalysed biotin deposition on chromatin nearby.

Another assay that has been developed is called chromosome conformation capture (3C) technology, which provides a tool to study the structural organisation of a genomic region. 3C technology involves quantitative PCR-analysis of cross-linking frequencies between two given DNA restriction fragments, which gives a measure of their proximity in the nuclear space (see FIG. 1). Originally developed to analyse the conformation of chromosomes in yeast (Dekker et al., 2002), this technology has been adapted to investigate the relationship between gene expression and chromatin folding at intricate mammalian gene clusters (see, for example, Tolhuis et al., 2002; Palstra et al., 2003; and Drissen et al., 2004). Briefly, 3C technology involves in vivo formaldehyde cross-linking of cells and nuclear digestion of chromatin with a restriction enzyme, followed by ligation of DNA fragments that were cross-linked into one complex. Ligation products are then quantified by PCR. The PCR amplification step requires the knowledge of the sequence information for each of the DNA fragments that are to be amplified. Thus, 3C technology provides a measure of interaction frequencies between selected DNA fragments.

3C technology has been developed to identify interacting elements between selected parts of the genome and both techniques require the design of primers for all restriction fragments analysed. Recently, new strategies have been developed that allow screening the entire genome in an unbiased manner for DNA segments that physically interact with a DNA fragment of choice. They are based on 3C technology and are collectively referred to as '4C technology'. 4C technology allows the screening of the entire genome in an unbiased manner for DNA segments that physically interact with a DNA fragment of choice. 4C technology depends on the selective ligation of cross-linked DNA fragments to a restriction fragment of choice (the 'bait'). In 4C technology, all the DNA fragments captured by the bait in the population of cells are simultaneously amplified via inverse PCR, using two bait-specific primers that amplify from circularized ligation products.

Essentially two strategies can be pursued to obtain these DNA circles. One strategy relies on the formation of circles during the standard 3C ligation step, i.e. while the DNA is still cross-linked (Zhao et al. (2006) *Nat Genet* 38, 1341-7). Here, circle formation requires both ends of the bait fragment to be ligated to both ends of a captured restriction fragment. If multiple restriction fragments are cross-linked together, circles may still be formed but they can contain more than one captured fragment and will therefore be larger. After de-crosslinking, captured DNA fragments are directly amplified by inverse PCR, using bait-specific primers facing outwards. Restriction enzymes recognizing four or six basepairs can be used in this set up. Four-cutters are preferred in this method though, since they produce smaller restriction fragments (average size 256 bp, versus ~4 kb for six-cutters) and linear PCR amplification of the captured DNA fragments requires that the average product size is small. Essentially, this method therefore comprises the steps of: (a) providing a sample of cross-linked DNA; (b) digesting the cross-linked DNA with a primary restriction enzyme—such as a 4 bp or a 5 bp cutter; (c) ligating the cross-linked nucleotide sequences; (d) reversing the cross linking and (e) amplifying the one or more nucleotide sequences of interest using at least two oligonucleotide primers, wherein each primer hybridises to the DNA sequences that flank the nucleotide sequences of interest. The amplified sequence(s) can be hybridised to an array in order to assist in determining the frequency of interaction between the DNA sequences.

The second strategy advantageously relies on the formation of DNA circles after the chromatin has been de-cross-linked as is described herein and in our co-pending application WO2007/004057. As described therein, 4C technology allows an unbiased genome-wide search for DNA fragments that interact with a locus of choice. Briefly, 3C analysis is performed as usual, but omitting the PCR step. The 3C template contains a target sequence or 'bait' (eg. a restriction fragment of choice that encompasses a selected gene) ligated to many different nucleotide sequences of interest (representing this gene's genomic environment). The template is cleaved by another, secondary, restriction enzyme and subsequently religated to form small DNA circles. Advantageously, the one or more nucleotide sequences of interest that are ligated to the target nucleotide sequence are amplified using at least two oligonucleotide primers, wherein at least one primer hybridises to the target sequence. The second primer preferably also hybridises to the target sequence, such that both primers flank the nucleotide of interest. Alternatively, the second primer hybridises to an adapter sequence that is ligated to the secondary restriction site, such that the two primers flank the nucleotide of interest. Typically, this yields a pattern of PCR fragments that is highly reproducible between independent amplification reactions and specific for a given tissue. HindIII and DpnII may be used as primary and secondary restriction enzymes. Next, the amplified fragments may be labeled and optionally hybridised to an array, typically against a control sample containing genomic DNA digested with the same combination of restriction enzymes. 3C technology has therefore been modified such that all nucleotide sequences of interest that interact with a target nucleotide sequence are amplified. Practically this means that instead of performing an amplification reaction with primers that are specific for the fragments that one wishes to analyse, an amplification is performed using oligonucleotide primer(s) which hybridise to a DNA sequence that flanks the nucleotide sequences of interest. Advantageously, 4C is not biased towards the design of PCR primers that are included in the PCR amplification step and can therefore be used to search the complete genome for interacting DNA elements.

There is an important need for high-throughput technology that can systematically screen the whole genome in an unbiased manner for DNA loci that contact each other in the nuclear space.

Moreover, there is a need for improvements in such technologies which permit the simultaneous analysis of multiple interactions occurring with multiple sequences in the genome, and for analysing the genome for insertions, deletions, translocations, inversions and rearrangements which take place at unknown locations and which may be associated with a disease.

The present invention seeks to provide improvements in 3C and 4C technology and techniques related thereto.

SUMMARY OF THE INVENTION 3C technology as currently applied only allows analysis of a limited number of selected DNA-DNA interactions owing to the limitations of the PCR amplification step, which requires knowledge of specific sequence information for each fragment to be analysed. Moreover, selecting restriction fragments as candidates for long-range DNA interactions requires a substantial amount of prior knowledge (e.g. the location of hypersensitive sites) of the locus of interest, which is usually not available. Given the functional relevance of many long-range DNA-DNA interactions described so far, the ability to randomly screen for DNA elements that loop to a sequence of interest—such as a gene promoter, enhancer, insulator, silencer, origin of replication or MAR/SAR—or a genomic region of interest—such as a gene-dense or gene-poor region or repetitive element—can greatly facilitate the mapping of sequences involved in a regulatory network.

The present invention relates to 4C technology (ie. capture and characterise co-localised chromatin) and improvements therein, which provides for the high-throughput analysis of the frequency of interaction of two or more nucleotide sequences in the nuclear space. 4C technology can be used to identify long-range DNA-DNA interactions (eg. study chromosome folding) but also to identify balanced and unbalanced genomic rearrangements—such as translocations, inversions, deletions, amplifications, etc—that may underlie a trait or disease in human subjects.

Routinely, 4C technology involves the use of microarrays to analyse the DNA fragments captured by a single selected target sequence ('bait') (Simonis et al., Nature Genetics 2006). Microarrays have the disadvantage that they offer a limited dynamic range since probes present on the arrays can be saturated, which makes a quantitative analysis of signal intensities more difficult. High-throughput sequencing circumvents this problem as it offers an unlimited dynamic range. It is also quantitative since it provides absolute numbers of sequences.

In addition, it is preferred to analyse DNA interactions with multiple target sequences simultaneously. This is true for all 4C-based applications and in particular for the 4C-based analysis of genomic rearrangements. 4C technology may be used as a diagnostic tool to allow the scanning of the entire genome in an unbiased manner for the presence of genomic rearrangements. A series of target sequences along each chromosome that together capture all sequences (ie. restriction fragments) may be used. Subsequently, in order to identify the genomic rearrangement, the sequence that was captured by which 'bait' is identified.

Captured fragments can be sequenced for each target sequence ('bait') separately. Preferably though, all ligation products formed with all target sequences are analysed simultaneously. For this, each read needs to be directed to the ligation junction and provide sufficient sequence information to unambiguously identify both the target sequence and the captured sequence.

SUMMARY ASPECTS OF THE PRESENT INVENTION

Aspects of the present invention are presented in the accompanying claims.

In a first aspect, there is provided a method for analysing the frequency of interaction of a target nucleotide sequence with one or more nucleotide sequences of interest (eg. one or more genomic loci) comprising the steps of: (a) providing a sample of cross-linked DNA; (b) digesting the cross-linked DNA with a primary restriction enzyme; (c) ligating the cross-linked nucleotide sequences; (d) reversing the cross linking; (e) optionally digesting the nucleotide sequences with a secondary restriction enzyme; (f) optionally ligating one or more DNA sequences of known nucleotide composition to the available secondary restriction enzyme digestion site(s) that flank the one or more nucleotide sequences of interest; (g) amplifying the one or more nucleotide sequences of interest using at least two oligonucleotide primers, wherein each primer hybridises to the DNA sequences that flank the nucleotide sequences of interest; (h) hybridising the amplified sequence(s) to an array; and (i) determining the frequency of interaction between the DNA sequences.

In a second aspect, there is provided a method for analysing the frequency of interaction of a target nucleotide sequence with one or more nucleotide sequences (eg. one or more genomic loci) comprising the steps of: (a) providing a sample of cross-linked DNA; (b) digesting the cross-linked DNA with a primary restriction enzyme; (c) ligating the cross-linked nucleotide sequences; (d) reversing the cross linking; (e) optionally digesting the nucleotide sequences with a secondary restriction enzyme; (f) circularising the nucleotide sequences; (g) amplifying the one or more nucleotide sequences that are ligated to the target nucleotide sequence; (h) optionally hybridising the amplified sequences to an array or analysing the amplified sequences by high-throughput sequencing; and (i) determining the frequency of interaction between the DNA sequences.

In a third aspect there is provided a method for identifying one or more DNA-DNA interactions that are indicative of a particular disease state comprising the step of performing steps (a)-(i) of the method according to the first aspect, wherein in step (a) a sample of cross-linked DNA is provided from a diseased and a non-diseased cell, and wherein a difference between the frequency of interaction between the DNA sequences from the diseased and non-diseased cells indicates a difference in the linear organisation of the chromosome templates (eg. a genomic rearrangement), which is indicative of a particular trait or disease state.

In a fourth aspect there is provided a method of diagnosis or prognosis of a disease or syndrome caused by or associated with a change in a DNA-DNA interaction comprising the step of performing steps (a)-(i) of the method according to the first aspect, wherein step (a) comprises providing a sample of cross-linked DNA from a subject; and wherein step (i) comprises comparing the frequency of interaction between the DNA sequences with that of an unaffected control; wherein a difference between the value obtained from the control and the value obtained from the subject is indicative that the subject is suffering from the disease or syndrome or is indicative that the subject will suffer from the disease or syndrome.

In a fifth aspect there is provided a method of diagnosis or prognosis of a disease or syndrome caused by or associated with a change in a DNA-DNA interaction comprising the step of: performing steps (a)-(i) of the method according to the first aspect, wherein step (a) comprises providing a sample of cross-linked DNA from a subject; and wherein said method comprises the additional step of: (j) identifying one or more loci that have undergone a genomic rearrangement that is associated with a disease.

In a sixth aspect there is provided an assay method for identifying one or more agents that modulate a DNA-DNA interaction comprising the steps of: (a) contacting a sample with one or more agents; and (b) performing steps (a) to (i) of the method according to the first aspect, wherein step (a) comprises providing cross-linked DNA from the sample; wherein a difference between (i) the frequency of interaction between the DNA sequences in the presence of the agent and (ii) the frequency of interaction between the DNA sequences in the absence of the agent is indicative of an agent that modulates the DNA-DNA interaction.

In a seventh aspect there is provided a method for detecting the location of a balanced and/or unbalanced rearrangement (eg. a translocation) comprising the step of: (a) performing steps (a) to (i) of the method according to the first aspect; and (b) comparing the frequency of interaction between the DNA sequences with that of a control; wherein a transition from low to high DNA-DNA interaction frequency in the sample as compared to the control is indicative of the location of a breakpoint.

In a eighth aspect there is provided a method for detecting the location of a balanced and/or unbalanced inversion comprising the steps of: (a) performing steps (a) to (i) of the method according to the first aspect; and (b) comparing the frequency of interaction between the DNA sequences with that of a control; wherein an inversed pattern of DNA-DNA interaction frequencies for the sample as compared to the control is indicative of an inversion.

In a ninth aspect there is provided a method for detecting the location of a deletion comprising the steps of: (a) performing steps (a) to (i) of the method according to the first aspect; and (b) comparing the frequency of interaction between the DNA sequences with that of a control; wherein a reduction in the DNA-DNA interaction frequency for the sample as compared to the control is indicative of deletion.

In a tenth aspect there is provided a method for detecting the location of a duplication comprising the steps of: (a) performing steps (a) to (i) of the method according to the first aspect; and (b) comparing the frequency of interaction between the DNA sequences with that of a control; wherein an increase or a decrease in DNA-DNA interaction frequency for the subject sample as compared to the control is indicative of a duplication or insertion.

In an eleventh aspect there is provided an agent obtained or obtainable by the assay method described herein.

In a twelfth aspect there is provided a method for analysing the frequency of interaction of one or more target nucleotide sequences with one or more nucleotide sequences of interest (eg. one or more genomic loci) comprising the steps of: (a) providing a sample of cross-linked DNA; (b) digesting the cross-linked DNA with a primary restriction enzyme; (c) ligating the cross-linked nucleotide sequences; (d) reversing the cross linking; and (e) sequencing the ligated nucleotide sequences.

In a thirteenth aspect there is provided a method for determining the presence of a genomic rearrangement in a sample comprising the steps of: (a) providing a sample of nucleic acid (eg. genomic DNA), wherein said nucleic acid comprises a nucleotide sequence of known sequence adjacent to the location of the suspected genomic rearrangement; (b) digesting the DNA with a primary restriction enzyme to form a plurality of restriction fragments; (c) optionally, purifying the restriction fragments; (d) ligating the restriction fragments to form circularised DNA; (e) optionally, purifying the circularised DNA; (f) digesting the circularised DNA with a secondary restriction enzyme to form a plurality of restriction fragments; (g) ligating the restriction fragments to form circularised DNA; (h) amplifying the suspected genomic rearrangement using one or more primers that hybridise to the nucleotide sequence of known sequence; and (i) sequencing the suspected genomic rearrangement.

In a fourteenth aspect there is provided a database of nucleic acid sequences of about 6-50 basepairs that directly flank, and optionally include, the primary restriction enzyme recognition site or the secondary restriction enzyme recognition site of each target sequence.

In a fifteenth aspect there is provided a database of nucleic acid sequences of about 12-50 basepairs that directly flank all relevant primary and secondary restriction enzyme recognition sites in the genome.

In a sixteenth aspect there is provided the use of the database of nucleic acid sequences for determining the genomic position of each of the captured sequences identified.

In a seventeenth aspect there is provided a method or an agent or a database or a use substantially as described herein and with reference to any of the Examples or Figures.

EMBODIMENTS OF THE INVENTION

Suitably, the ligation reaction in step (c) or (f) results in the formation of DNA circles.

Suitably, step (h) comprises the analysis of ligation products between target sequences and cross-linked sequences of interest by means of sequencing (eg. high-throughput sequencing).

Suitably, the method is for analysing the frequency of interaction of two or more target nucleotide sequences with one or more nucleotide sequences of interest, comprising the use of multiplex PCR in step (g).

Suitably, the method is for analysing the frequency of interaction of two or more target nucleotide sequences with one or more nucleotide sequences of interest, comprising the pooling of some or all of the PCR products obtained for each of the target sequences in step (g) and subsequent simultaneous analysis of their DNA interactions.

Suitably, two or more amplified sequences are differentially labelled prior to pooling and analysis by hybridisation to an array.

Suitably, two or more amplified sequences are identically labelled and analysed by hybridisation to an array when the sequences reside on different chromosomes.

Suitably, two or more amplified sequences are identically labelled when the sequences reside on the same chromosome at a distance that is far enough for minimal overlap between DNA-DNA interaction signals.

Suitably, high throughput sequencing is used to analyse the ligation junctions formed between target sequences and captured sequences of interest.

Suitably, sequencing is directed to the ligation junctions formed between target sequences and captured sequences of interest by the addition of adapter sequences required for sequencing to the ends of the amplified sequences.

Suitably, sequencing is directed to the ligation junctions formed between target sequences and captured sequences of interest by the addition of the complete, or part of the, adapter sequences required for sequencing as 5' overhangs to the oligonucleotide primers used to amplify the one or more nucleotide sequences of interest.

Suitably, sequencing is directed to the ligation junctions formed between target sequences and captured sequences of interest by the conjugation of a biotin substance or other moiety to the oligonucleotide primers used to amplify the one or more nucleotide sequences of interest, followed by streptavidin or otherwise mediated purification of the PCR amplified material.

Suitably, sequencing is directed to the ligation junctions between target sequences and captured sequences of interest by designing the oligonucleotide primers used to amplify the one or more nucleotide sequences of interest within 400, 300, 200, 150, 100, 90, 80 70, 60, 50, 40, 30, 20, 10, 9, 8, 7, 6, 5, 4, 3, 2, 1 nucleotides from the primary and/or secondary restriction enzyme recognition site(s) analysed.

Suitably, sequencing is directed to the ligation junctions between target sequences and captured sequences of interest by designing the oligonucleotide primers used to amplify the one or more nucleotide sequences of interest such that they partially or completely overlap with the primary and/or secondary restriction enzyme recognition site analysed.

Suitably, sequences are read across the ligation junction such that when multiplexed or pooled PCR samples are analysed, sufficient sequence information (eg. 12 nucleotides or more) is obtained on either side of the ligation junction to unambiguously identify each target sequence and each captured sequence of interest.

Suitably, the target nucleotide sequence is selected from the group consisting of a genomic rearrangement, promoter, an enhancer, a silencer, an insulator, a matrix attachment region, a locus control region, a transcription unit, an origin of replication, a recombination hotspot, a translocation breakpoint, a centromere, a telomere, a gene-dense region, a gene-poor region, a repetitive element and a (viral) integration site.

Suitably, the target nucleotide sequence is a nucleotide sequence that is associated with or causes a disease, or is located up to or greater than 15 Mb on a linear DNA template from a locus that is associated with or causes a disease.

Suitably, the target nucleotide sequence is selected from the group consisting of: AML1, MLL, MYC, BCL, BCR, ABL1, IGH, LYL1, TAL1, TAL2, LMO2, TCRα/δ, TCRβ and HOX or other loci associated with disease as described in "Catalogue of Unbalanced Chromosome Aberrations in Man" 2nd edition. Albert Schinzel. Berlin: Walter de Gruyter, 2001. ISBN 3-11-011607-3.

Suitably, the target sequences are distributed along the linear genome template such that the interacting sequences cover an entire chromosome or the genome.

Suitably, the primary restriction enzyme is a restriction enzyme that recognises a 6-8 bp recognition site.

Suitably, the primary restriction enzyme is selected from the group consisting of Bg/II, HindIII, EcoRI, BamHI, SpeI, PstI and NdeI.

Suitably, the primary restriction enzyme is selected based on its absence from, or under representation in repetitive sequences.

Suitably, the secondary restriction enzyme is a restriction enzyme that recognises a 4 or 5 bp nucleotide sequence recognition site.

Suitably, the secondary restriction enzyme recognition site is located at greater than about 350 bp from the primary restriction site in the target nucleotide sequence.

Suitably, a transition from low to high interaction frequencies is indicative of the location of a balanced and/or unbalanced genetic rearrangement.

Suitably, an inversed pattern of DNA-DNA interaction frequencies for the subject sample as compared to the control is indicative of an balanced and/or unbalanced inversion.

Suitably, a reduction in the DNA-DNA interaction frequency for the subject sample as compared to the control, in combination with an increase in DNA-DNA interaction frequency for more distant regions, is indicative of a balanced and/or unbalanced deletion.

Suitably, an increase or a decrease in DNA-DNA interaction frequency for the subject sample as compared to the control is indicative of a balanced and/or unbalanced duplication or insertion.

Suitably, spectral karyotyping and/or FISH is used prior to performing said method.

Suitably, the disease is a genetic disease.

Suitably, the disease is cancer.

Suitably, nucleotide sequences interacting with two or more target sequences are amplified.

Suitably, the target sequences are positioned at or near genomic loci known to be associated with a diseased state.

Suitably, the target sequences are selected without prior knowledge on the location of a rearrangement and are spaced such that the interacting sequences cover an entire chromosome or the genome, and wherein the identified interacting sequences allow reconstructing linear chromosome maps and genomic rearrangements that occurred within and between chromosomes.

Suitably, the amplified sequences are labelled.

Suitably, the amplified sequences are differentially labelled according to their position in the genome.

Suitably, the method is for the detection of a balanced and/or unbalanced rearrangement, translocation, inversion, deletion, duplication or insertion.

Suitably, the array hybridisation step is replaced with a sequencing step.

Suitably, both the target nucleotide sequence and the nucleotide sequence of interest are identified by sequencing.

Suitably, adapter sequences are ligated to the PCR products.

Suitably, sequences interacting with two or more target sequences are amplified each in separate PCR reactions.

Suitably, sequences interacting with two or more target sequences are amplified each in separate PCR reactions and subsequently pooled for simultaneous analysis.

Suitably, sequences interacting with two or more target sequences are amplified by multiplex PCR.

Advantages

The present invention has a number of advantages. These advantages will be apparent in the following description.

By way of example, 4C technology can be multiplexed, such that interactions with two or more target sequences can be analysed in a single experiment, for example on a single array.

By way of further example, multiplexed 4C technology can be used to screen for rearrangements in genomic DNA throughout the genome, at unknown positions.

By way of further example, high-throughput sequencing can be used in place of microarrays to analyse the captured DNA fragments. The multiplexing and sequencing improvements may even be combined.

By way of further example, instead of multiplexing, sequences of interest captured by different target sequences can be amplified for each target sequence separately and then subsequently pooled to be analyzed simultaneously on a microarray.

By way of further example, instead of multiplexing, sequences of interest captured by different target sequences can be amplified separately for each target sequence and subsequently pooled to be analyzed simultaneously by high throughput sequencing.

By way of example, the present invention is advantageous since it provides inter alia commercially useful nucleotides sequences, processes, probes and arrays.

By way of further example, the present invention is advantageous since it provides for the high throughput analysis of the frequency of interaction of two or more nucleotide sequences in the nuclear space.

By way of further example, the present invention is advantageous since using conventional 3C technology, each single DNA-DNA interaction must be analysed by a unique PCR reaction containing a unique pair of primers. High-throughput analysis is therefore only possible if PCR is automated, but the costs of so many primers will be too high. Accordingly, high-throughput (genome-wide) analysis of DNA-DNA interactions is not viable with conventional 3C technology. In contrast, the present invention now allows the simultaneous screening of thousands of DNA-DNA interactions. High-throughput analysis of DNA-DNA interactions according to the present invention will greatly increase the scale and resolution of analysis.

By way of further example, the present invention is advantageous since using conventional 3C technology, the screen is biased towards those DNA sequences for which oligonucleotide primers were designed, ordered and included in the analysis.

The choice of such oligonucleotide primers is typically based on knowledge concerning the position of, for example, (distant) enhancers and/or other regulatory elements/hypersensitive sites that it is believed will cross-link with the nucleotide sequence that is being investigated. Thus, conventional 3C is biased towards the design of PCR primers that are included in the PCR amplification step, whereas 4C is unbiased and can be used to search the complete genome for interacting DNA elements. This is because amplification of cross-linked sequences in 4C is not based on the predicted knowledge of sequences that cross-link with the nucleotide sequence being investigated. Rather, in one embodiment of 4C, sequences that cross link to the first (target) nucleotide sequence can be amplified using PCR primers that hybridise to that nucleotide sequence. Thus, the present invention allows an unbiased genome-wide screen for DNA-DNA interactions.

By way of further example, the present invention is advantageous because using conventional 3C technology only allows the selective amplification of a single DNA-DNA interaction. This is not informative when hybridised to an array. The technology has been improved such that all fragments that interact with a first (target) nucleotide sequence are now amplified eg. selectively amplified.

By way of further example, the present invention is advantageous because 4C technology can be used to detect balanced or unbalanced genetic aberrations—such as all types of translocations, deletions, inversions, duplications and other genomic rearrangements—in nucleic acid, for example, chromosomes. 4C technology (which measures proximity of DNA fragments) can even determine a subject's predisposition to acquire certain translocations, deletions, inversions, duplications and other genomic rearrangements (eg. balanced or unbalanced translocations, deletions, inversions, duplications and other genomic rearrangements). An advantage over current strategies is that it is not required to know the exact position of the change because the resolution of 4C technology is such that it can be used to detect rearrangements even when the '4C-bait' (as defined by the primary and secondary restriction enzyme recognition sites that are analysed) is located away (eg. up to one megabase or even more) from the change. Another advantage over current strategies is that it allows for a simultaneous, unbiased genome-wide search for both balanced and unbalanced genomic rearrangements. Another advantage is that 4C technology allows the accurate mapping of changes since it can be used to define the two (primary) restriction sites between which changes occurred. Another advantage is that cells need not to be cultured before fixation. Thus, for example solid tumours can also be analysed for genomic rearrangements.

By way of further example, the present invention is advantageous because the 4C technology can also detect changes (eg. rearrangements) in a pre-malignant state, i.e. before all the cells contain these changes. Thus, the technology can be used not only in the diagnosis of disease but also in the prognosis of disease.

By way of further example, the array design according to the present invention is particularly advantageous as compared to existing genomic tiling arrays—such as Nimblegen genomic tiling arrays—since the design allows representation of a much larger part of the genome per single array. By way of example, for a restriction enzyme recognising a hexanucleotide sequence about 3 arrays with about 385,000 probes each will be sufficient to cover, for example, the complete human or mouse genome. For a restriction enzyme recognising more than 6 bp, a single array of about 385,000 probes can be used to cover, for example, the complete human or mouse genome. The advantages of the array design are that: (1) each probe is informative since each analyses an independent ligation event, greatly facilitating the interpretation of the results; and (2) a large representation of the genome can be spotted on a single array which is cost-effective.

4C technology can advantageously be used for the fine-mapping of poorly characterised rearrangements originally detected by cytogenetic approaches (light microscopy, FISH, SKY, etc).

4C technology can advantageously be used for the simultaneous screening on a single array for combinations of rearrangements that have occurred near multiple loci.

The principle of 3C technology

FIG. 2

Figure 1:
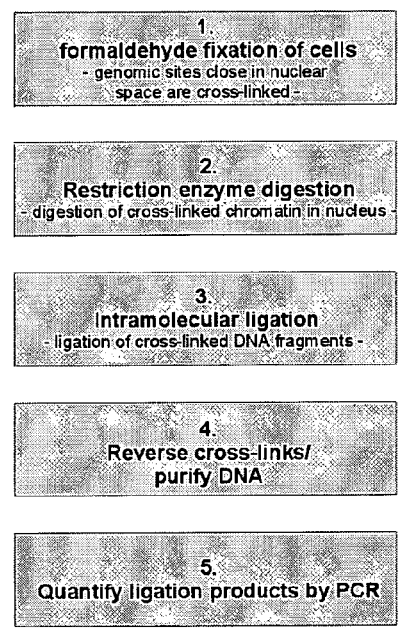
FIG. 1

(a) The principle of one embodiment of 4C technology. 3C analysis is performed as usual, with e.g. HindIII (H) as restriction enzyme. After reversal of cross-links, DNA mix will contain a first (target) nucleotide sequence ligated to many different fragments. These fragments will be amplified and labelled by using amplification methods—such as inverse PCR—on eg., DpnII circles, using first (target) nucleotide sequence-specific primers. Labelled amplification products may be hybridised to the arrays as described herein. HindIII and DpnII are given as examples, but other combinations of restriction enzymes—such as 6 or 8- and 4 or 5-cutters—can also be used. (b) PCR results separated by gel electrophoresis from two independent fetal liver (L1, L2) and brain (B1, B2) samples. (c) Schematic representation of the location of the microarray probes. Probes were designed within 100 bp of HindIII sites. Thus, each probe analyzes one possible ligation partner.

FIG. 3

4C technology detects the genomic environment of Rad23A (chromosome 8). Shown are unprocessed ratios (4C signals for Rad23A divided by signal obtained for control sample) for probes located in ~15 Mb or more genomic regions on mouse chromosome 10, 11, 12, 14, 15, 7 and 8 (top to bottom; regions shown are at identical distance from each corresponding centromere). Note the large cluster of strong signals around the (Rad23A) bait on chromosome 8 (row 7), which demonstrates that 4C technology detects genomic fragments close on the linear chromosome template (in agreement with the fact that interaction frequencies are inversely proportional to the genomic site separation). Note that the region linked in cis around the bait that shows high signal intensities is large (>5 Mb), implying for example that translocations can be detected even with baits more than 1 MB away from the breakpoint.

FIG. 4

4C interactions of β-globin on chromosome 7 (~135 Mb) for a transcribing tissue (fetal liver) and a non-transcribing tissue (fetal brain) (analysed by a running mean approach). Note that long-range interactions with β-globin differ between tissues (likely dependent on the transcription status of the gene). Independent of the tissue strong 4C signals demarcate a large region (>5 Mb) around the bait.

FIG. 5

Uros and Eraf interact with β-globin in fetal liver cells. The 4C approach reveals that two genes, Eraf and Uros, interact over >30 Mb with the β-globin locus located ~30

Mb away. These two interactions were previously found by a different technology (Fluorescence In Situ Hybridisation) as described in Osborne et al., Nature Genetics 36, 1065 (2004). This example shows that long-range interactions detected by 4C technology can be verified by FISH and truly reflect nuclear proximity.

FIG. 6

4C technology accurately identifies transitions between unrelated genomic regions that are linked in cis. For these experiments transgenic mice were used that contain a human β-globin Locus Control Region (LCR) cassette (~20 kb) inserted (via homologous recombination) into the Rad23A locus on mouse chromosome 8. 4C technology was performed on E14.5 fetal livers of transgenic mice that were homozygous for this insertion. A HindIII fragment within the integration cassette (HS2) was used as '4C-bait'. The data show that 4C technology accurately defines both ends of the transgenic cassette (bottom row: only probes in the human LCR (~20 kb) give 4C-signals and not probes in the remainder of ~380 kb human β-globin sequence) and clearly reveals the position of integration on mouse chromosome 8 (upper panel: compare signals on chromosome 8 (for position of integration, see arrow) with signals on 6 other mouse chromosomes) (complete chromosomes are depicted). This example shows that 4C technology can be used to detect the genomic position of ectopically integrated DNA fragments (virus, transgene, etc.). It shows that transitions between unrelated genomic regions that are linked in cis can be identified accurately, which can be used to identify genomic breakpoints and translocation partners.

FIG. 7

4C technology produces reproducible data since the profile for HS2 and β-globin are very similar. Four biologically independent 4C experiments were performed on E14.5 fetal livers, using either the β-globin gene β-major (upper 2 rows) or β-globin HS2 (bottom two rows) as the bait. These baits are ~40 kb apart on the linear chromosome template but were previously shown to be close in the nuclear space (Tolhuis et al, Molecular Cell 10, 1453 (2002)) Depicted is a ~5 Mb region on mouse chromosome 7 that is 20-20 Mb away from the β-globin locus. The data show high reproducibility between independent experiments and demonstrate that two fragments close in the nuclear space share interacting partners located elsewhere in the genome.

FIG. 8

4C technology is applied to measure DNA-DNA interaction frequencies with sequence X (on chromosome A) in cells from a healthy person (top) and a patient with translocation (A;B) (bottom). Signal intensities representing DNA-DNA interaction frequencies (Y-axis) are plotted for probes ordered on linear chromosome templates (X-axis). In normal cells, frequent DNA-DNA interactions are detected on chromosome A around sequence X. In patient cells, a 50% reduction in interaction frequencies is observed for probes on chromosome A located on the other side of the breakpoint (BP) (compare grey curve (patient) with black line (healthy person). Moreover, the translocation brings part of chromosome B in close physical proximity to sequence X, and frequent DNA-DNA interactions are now observed for this region on chromosome B. The abrupt transition from low to high interaction frequencies on this chromosome marks the location of its breakpoint.

FIG. 9

(Balanced) inversion(s) can be detected by 4C technology. Inversed patterns of DNA-DNA interaction frequencies (measured by 4C technology as hybridization signal intensities) are observed in diseased (solid curve) as compared to non-diseased (stippled curve) subject, which reveals the presence and size of the inversion.

FIG. 10

Heterozygous deletion(s) detection by 4C technology. Probes with reduced DNA-DNA interaction frequencies (measured by 4C technology as hybridization signal intensities) in diseased (grey curve) as compared to non-diseased (black curve) subjects, reveal the position and size of the deleted region. Residual hybridization signals in the deleted region of the diseased subject come from intact allele (heterozygous deletion). Deletion is typically accompanied by an increase in signal intensities for probes located directly beyond the deleted region (note that the grey curve is above the black curve at right hand of the deletion), since these regions come in closer physical proximity to the 4C sequence (bait).

FIG. 11

Duplication detected by 4C technology. Probes with increased hybridization signals in a patient (solid curve) as compared to a normal subject (stippled curve) indicate the position and size of duplication. Duplication as detected by 4C technology is typically accompanied by decreased hybridization signals in diseased versus non-diseased subjects for probes beyond the duplicated region (duplication increases their genomic site separation from the 4C sequence).

FIG. 12

Long-range interactions with β-globin revealed by 4C technology. a, Unprocessed ratios of 4C over control hybridization signals, revealing interactions of β-globin HS2 with chromosome 7 and two unrelated chromosomes (8 and 14). b-c, Unprocessed data for two independent fetal liver (top, in red) and fetal brain samples (bottom, in blue) plotted along two different 1-2 Mb regions on chromosome 7. Highly reproducible clusters of interactions are observed either in the two fetal liver samples (b) or the two brain samples (c). d-e, Running mean data for the same regions. False discovery rate was set at 5% (stippled line). f, Schematic representation of regions of interaction with active (fetal liver, top) and inactive (fetal brain, bottom) β-globin on chromosome 7.

FIG. 13

Active and inactive β-globin interact with active and inactive chromosomal regions, respectively. a, Comparison between β-globin long-range interactions in fetal liver (4C running mean, top), microarray expression analysis in fetal liver (log scale, middle) and the location of genes (bottom) plotted along a 4 Mb region that contains the gene Uros (~30 Mb away from β-globin), showing that active β-globin preferentially interacts with other actively transcribed genes. b, The same comparison in fetal brain around a OR gene cluster located ~38 Mb away from globin, showing that inactive β-globin preferentially interacts with inactive regions. c, Characterization of regions interacting with β-globin in fetal liver (left) and brain (right) in terms of gene content and activity.

FIG. 14

Ubiquitously expressed Rad23A interacts with very similar, active, regions in fetal liver and brain. a, Schematic representation of regions on chromosome 8 interacting with active Rad23A in fetal liver (top, red) and brain (bottom, blue). b, Comparison between Rad23A long-range interactions (4C running mean) and microarray expression analysis (log scale) in fetal liver (top two panels), Rad23A long-range interactions (4C running mean) and microarray expression analysis (log scale) in fetal brain (panel 3 and 4) and the location of genes (bottom panel) plotted along a 3 Mb region of chromosome 8. c, Characterization of regions interacting with Rad23A in fetal liver (left) and brain (right) in terms of gene content and activity.

FIG. 15

Cryo-FISH confirms that 4C technology truly identifies interacting regions. a, example of part of a (200 nm) cryo-section showing more than 10 nuclei, some of which containing the β-globin locus (green) and/or Uros (red). Due to sectioning, many nuclei do not contain signals for these two loci. b-d, examples of completely (b) and partially (c) overlapping signals and contacting signals (d), which were all scored as positive for interaction. e-g, examples of nuclei containing non-contacting alleles (e-f) and a nucleus containing only β-globin (g), which were all scored as negative for interaction. h-i, Schematic representation of cryo-FISH results. Percentages of interaction with β-globin (h) and Rad23A (i) are indicated above the chromosomes for regions positively identified (red arrowhead) and negatively identified (blue arrowhead) by 4C technology. The same BACs were used for the two tissues. Interaction frequencies measured by cryo-FISH between two distant OR gene clusters in fetal liver and brain are indicated below the chromosomes.

FIG. 16

4C analysis of HS2 and β-major give highly similar results. (a (Unprocessed 4C data of four independent E14.5 liver samples show a very similar pattern of interaction with HS2 (top) and β-major (bottom). (b) A large overlap exists between probes scored positive for interaction in the HS-2 experiment and probes that scored positive for interaction in the β-major experiment.

FIG. 17

Regions that interact with β-globin also frequently contact each other. Two regions (almost 60 Mb apart), containing actively transcribed genes and identified by 4C technology to interact with β-globin in fetal liver, showed co-localization frequencies by cryo-FISH of 5.5%, which was significantly more than background co-localization frequencies.

FIG. 18

Example of a heterozygous deletion revealed by multiplex 4C using a single dye for the labelling of DNA fragments interacting with multiple target sequences. The ratio of interaction frequencies observed in a patient (sample) over healthy person (control) is depicted on the right.

FIG. 19

The presence of a deletion present in a leukaemia patient as revealed by 4C using a target nucleotide sequence that is either at 2 Mb (A) or at 1.3 Mb (B) upstream ('to the left') from the first breakpoint. Note that deletions cause a reduction of DNA interaction signals at the deleted region, but also cause an increase in DNA:DNA interaction frequencies for sequences directly downstream ('at the right') of the last breakpoint. This is particularly obvious when interactions with target nucleotide sequence B are closely examined (see bottom two graphs). Based on 4C data primers were designed on each side of the deleted region and breakpoint was identified by sequencing: (SEQ ID NO:25) plain text is sequence upstream of deletion, in bold indicated is an inserted nucleotide, underlined is the sequence downstream of the deletion.

FIG. 20

A heterozygous inversion revealed by multiplex 4C using a single dye for the labelling of DNA fragments interacting with multiple target sequences. The ratio of interaction frequencies observed in patient (sample) over healthy person (control) is depicted on the right. Note that ratios near breakpoints may be different when the position of the breakpoints relative to the target nucleotide sequences is different.

FIG. 21

Colours alternate between neighbouring target nucleotide sequences, which allows for the detection (in red) of a deletion close to a target nucleotide sequence (in blue) that fails to detect the deletion due to saturated hybridisation signals. In case the amount of probe on the array is not saturating the blue signal would also be decreased at the deletion.

FIG. 22

Colours alternate between neighbouring target nucleotide sequences, which allows for the detection (in red) of an inversion. The ratio of interaction frequencies observed in the patient (sample) over healthy person (control) is depicted on the right. Note that compared to a single dye experiment (see FIG. 2) the use of alternating dyes facilitated the detection of rearrangements such as inversions. Also note that ratios near breakpoints may be different when the position of the breakpoints relative to the target nucleotide sequences is different.

FIG. 23

Figure 4:
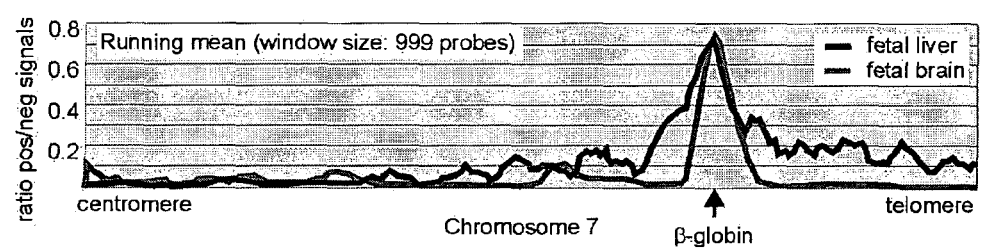

Example of a heterozygous inversion revealed by multiplex 4C using a different dyes for the labelling of DNA fragments interacting with different target sequences. Breakpoints of the inversion are indicated by the position of red and green signals in the patient that are absent in the control sample. Note that introduction of more colours facilitates the detection of rearrangements (compare for example FIGS. 4 and 5).

FIG. 24

Detection of balanced translocations. Each chromosome is labelled with two unique dyes that are used such that the dyes alternate between target sequences that neighbour on the linear chromosome template. If translocations are balanced, each of the two chromosome-specific dyes should give strong hybridisation signals on a mutually exclusive set of probes directly neighbouring each other on the linear template of the unrelated chromosome. The breakpoint on this unrelated chromosome is located in between the two sets of probes showing positive hybridisation signals. The parent chromosome signals at and past the breakpoint would be half the intensity of the control (not shown in the figure)

FIG. 25

Proof of principle for the detection of balanced translocations. Detection of t(1;7) translocation as described in (R. Burnett et al., Blood, Vol 84, No 4 (August 15), 1994: pp 1232-1236). Target nucleotide sequences flank the TCRβ locus on chromosome 7, with the red signals representing DNA:DNA interactions with the target sequence that is located upstream of the TCRβ locus, and the blue signals representing DNA:DNA interactions with the target sequence that is located downstream of the TCRβ locus. Depicted are the interacting DNA signals found on chromosome 1. Top panel shows the theoretical signal distribution. The middle and lower panel show the actual signal distribution. The bottom panel shows signals at a resolution of individual probes juxtaposed on the chromosome template. Note that in case of a balanced translocation target nucleotide sequences flanking the breakpoint will show a mutually exclusive set of interchromosomal DNA interaction signals that directly border each other on the linear chromosome template of the translocating partner chromosome. Position of sequenced breakpoint (described in Burnett et al., 1994) is indicated by an arrow at the bottom panel.

FIG. 26

Theoretical example for the detection of unbalanced translocations. Each chromosome is labelled with two unique dyes that are used such that the dyes alternate between target sequences that neighbour on the linear chromosome template. If translocations occurred with loss of DNA at the breakpoints (i.e. unbalanced translocations), each of the two chromosome-specific dyes will give strong hybridisation signals on a mutually exclusive set of probes on the unrelated chromosome that do not directly neighbour each other on the linear template of the unrelated chromosome. The deleted region is indicated.

FIG. 27

Detection of unbalanced translocations. Detection of t(4;7) translocation as described in (R J Galjaard et al., Am J Med Genet A. 2003 Aug. 30; 121(2):168-73). Target nucleotide sequences locate to chromosome 7; the depicted interacting DNA signals are located on chromosome 4. Two target sequences were used located upstream (5') and downstream (3') of the breakpoint on chromosome 7. Interacting DNA signals located on chromosome 4 are indicated (for both target sequences in blue). The region in between the clusters of interacting DNA fragments on chromosome 4 has been deleted in this patient. Top: signals for the complete chromosome 4. Bottom panel 4C data: signals at a 11.5 MB region around the breakpoints on chromsome 4. Based on these 4C data, the HindIII restriction fragment on chromosome 4 containing the translocation breakpoint was identified and used to map the breakpoint by sequencing. The sequence is provided at the bottom of the figure (SEQ ID NO:26), where underlined sequence is from chromosome 4, bold is found both on 7 and 4 and plain sequence is from chromosome 7.

FIG. 28

Chromosome-specific labelling of DNA interactions. Blue signal appearing on chromosome 3 and orange signals appearing on chromosome 1 reveal the translocation partner chromosomes and the approximate position of the breakpoints.

FIG. 29

Sequencing of PCR amplified nucleotide sequences of interest (blue: travel address) ligated to target nucleotide sequence (red: home address). Amplification was done using primers (red), at least one which being complementary to target nucleotide sequence. Optionally, adapters (green) can be introduced in various ways at the end of the PCR products, as indicated.

FIG. 30

4C accurately detects a balanced translocation and inversion (A-B) 4C technology detects a balanced translocation t(1;7). (A) In a healthy control sample, target fragments a (red) and b (blue) that are located at opposite sides of the TCRB locus on chromosome 7 do not capture regions on chromosome 1. (B) In the HSB-2 cell line containing a balanced translocation t(1;7)(p35;q35), each TCRB target fragment captures a region on chromosome 1. The regions captured are several megabases in size (zoom 1), directly neighbor each other (zoom 2) and flank the previously cloned breakpoint (arrow). See FIG. S1 for results other chromosomes. (C-D) 4C detects a balanced inversion. (C) In a healthy control sample, target fragments a (red) and b (blue) that are located at opposite sides of the TCRB locus on chromosome 7 do not capture large regions elsewhere on chromosome 7. (D) In a T-ALL patient sample, each TCRB target fragment captures an additional region at the other end of chromosome 7. The most 5' target fragment (a; red) captures a region 5' of the HOXA cluster, the most 3' target fragment (b: blue) captures a region 3' of the HOXA cluster, demonstrating an inversion. The regions captured are several megabases in size (zoom 1) and directly neighbor each other (zoom 2), showing that the inversion is balanced. Both target fragments identify the breakpoint (arrow) near HOXA9 within a 6 kb region. Running mean data were plotted, using a window size of ~60 kb. Zooms show unprocessed signal intensities.

FIG. 31

4C accurately detects unbalanced rearrangements. (A) 4C accurately detects a translocation t(4;7)(p15.2;q35) in combination with a microdeletion (i.e. unbalanced rearrangement) in an cell line from an unborn child with congenital malformation. Target fragments a (red) and b (blue) that were located on opposite sides of the breakpoints on chromosome 7 both capture fragments spanning several megabases on chromosome 4 (for signals on other chromosomes, see FIG. 35). The two captured regions with high signals do not directly neighbor each other, showing that the translocation is accompanied by a deletion on chromosome 4. (B) (SEQ ID NO:27) Sequence of one of the breakpoints (arrow), with chromosome 7 and 4 sequences in small and capital letters, respectively. (C) 4C accurately identifies a homozygous deletion in a T-ALL patient sample. A target fragment located on chromosome 9 at 19.3 Mb identifies a region (between arrows) lacking high signals in the patient sample (bottom) compared to control sample (top), showing a ~2 Mb deletion on 9p21. Signals 3' of the deletion are higher in patient versus control, as this region is in closer proximity to the target fragment due to the deletion. (D) (SEQ ID NO:28) Sequence across the breakpoints indicated by the arrows in (C), confirming the deletion. Plotted in this figure are unprocessed signal intensities. Rare high signals in deleted regions indicate that these probes show non-specific hybridization.

FIG. 32

4C screen identifies LMO3 as a novel translocation partner of TCRB. Five uncharacterized T-ALL patient samples were screened with 4C, using a target fragment near the TCRB locus on chromosome 7. (A) In one patient sample high signals appeared specifically on chromosome 12, revealing a translocation, t(7;12)(q35;p12.3). For signals on all other chromosomes, see FIG. S4. A deletion is present several megabases from the translocation site (arrow) on chromosome 12 (zoom 1). The translocation site is present in a 6 kb region close to the LMO3 gene (zoom 2). (B) Sequences of both breakpoints of t(7;12)(q35;p12.3) (SEQ ID NO:29. SEQ ID NO:30); nucleotides in upper case are from 12, in lower case from 7 and in italics are from unknown origin. (C) Schematic representation of the translocation site of t(7;12)(q35;p12.3). The enhancer of TCRB is positioned 70 kb downstream of the LMO3 gene. Running mean data were plotted, using a window size of ~60 kb. Zooms show unprocessed signal intensities.

FIG. 33

4C signals across all chromosomes in a healthy control and a sample carrying t(1;7)(p35;q35). The black arrowheads indicate position of target sequences. The red arrowhead indicates the position of the translocation site. Running mean data were plotted, using a window size of ~60 kb. Scale on Y-axis (arbitrary units) is identical for all chromosomes.

FIG. 34

Figure 30:
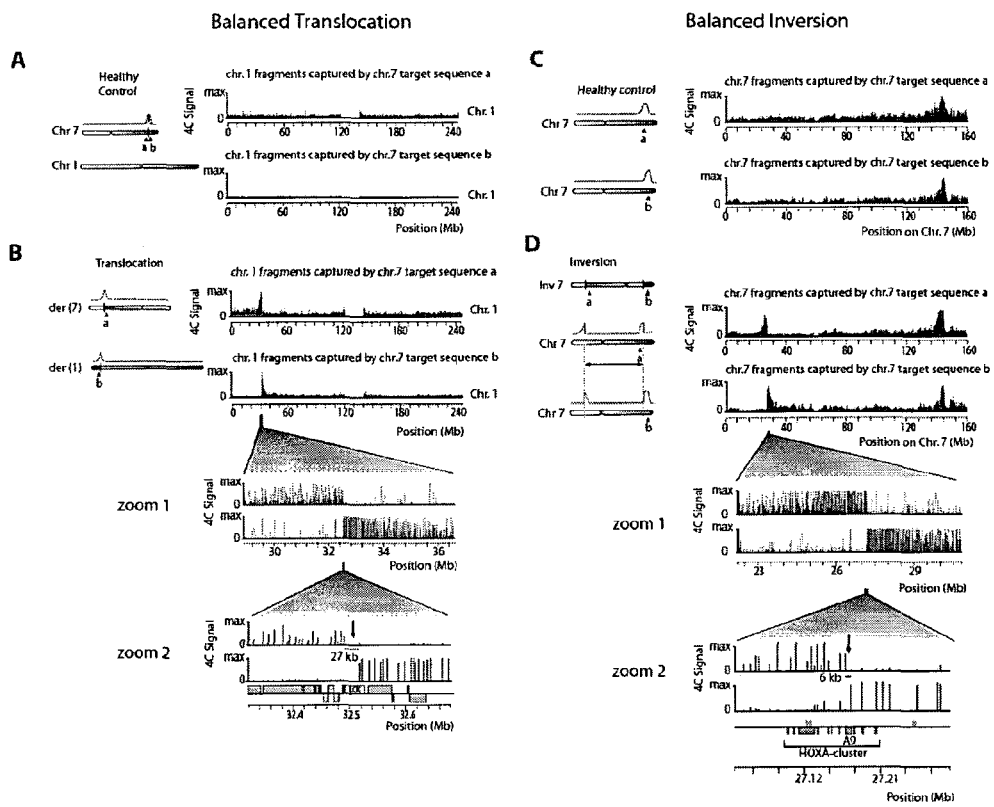

Restriction-fragment-paired-end-sequencing (A) Schematic representation of restriction-fragment-paired-end-sequencing. (B) Breakpoint sequences (SEQ ID NO:31) of an inversion between TCRB and HOXA on chromosome 7 (see FIG. 30). The black sequence is located at the position in HOXA found with 4C technology, in between the probes that mark the transition from captured to non-captured fragments. The red sequence was found with restriction-fragment-paired-end-sequencing from the black sequence and is located in the TCRB-locus.

FIG. 35

4C signals across all chromosomes obtained with two different chromosome 7 target fragments in a sample carrying t(4;7)(p15.2;q35). The black arrowheads indicate position of target sequences. The red arrowheads indicate the position of the translocation sites. Running mean data were plotted, using a window size of ~60 kb. Scale on Y-axis (arbitrary units) is identical for all chromosomes.

FIG. 36

4C signals across all chromosomes obtained with a target sequence near the TCRB locus on chromosome 7 in two T-ALL patient samples, one of which carrying a t(7;12) translocation. The black arrowheads indicate position of target sequences. The red arrowhead indicates the position of the translocation site. Running mean data were plotted, using a window size of ~60 kb. Scale on Y-axis (arbitrary units) is identical for all chromosomes.

FIG. 37

LMO3 expression in T-ALL patient samples. Gene expression was measured on affymetrix gene expression arrays. LMO3 is expressed in the patient carrying t(7;12)(q35;p12.3), but not in the other patients.

FIG. 38

4C PCR primers and product to be analysed by Solexa sequencing. Sequences produced by Solexa (arrows) first read the 'DpnII primer' (18 nucleotides, including GATC (i.e. DpnII recognition site)), followed by the captured sequence.

FIG. 39

PCR results using primers with 5' overhangs containing Solexa adapter sequences. For comparison, results obtained with standard primers (lanes 1, 5, 9 from left to right; no overhangs) are also shown.

FIG. 40

Results from 4C-sequencing.

FIG. 41

Primerset 3 (139 Mb) captures chromosome 1 sequences across the breakpoint in the HSB-2 T-ALL cell line (on chromosome 7 at ~142 Mb, i.e. 3 Mb away from the bait). For comparison, microarray results are shown. Note that the target sequence (bait) used for the microarray experiment was closer (<1 Mb) to the breakpoint, explaining why it maps the breakpoint on chromosome 1 better.

DETAILED DESCRIPTION OF THE INVENTION

3C Technology

The 3C method has been described in detail in Dekker et al. (2002), Tolhuis et al. (2002), Palstra et al. (2003), Splinter et al. (2004) and Drissen et al. (2004). Briefly, 3C is performed by digesting cross-linked DNA with a primary restriction enzyme followed by ligation at very low DNA concentrations. Under these conditions, ligation of cross-linked fragments, which is intramolecular, is strongly favoured over ligation of random fragments, which is intermolecular. Cross-linking is then reversed and individual ligation products are detected and quantified by the polymerase chain reaction (PCR) using locus-specific primers. The cross linking frequency (X) of two specific loci is determined by quantitative PCR reactions using control and cross-linked templates, and X is expressed as the ratio of the amount of the product obtained with the cross-linked template and with the control template.

In accordance with the present invention, a 3C template is prepared using the methods described by Splinter et al., (2004) *Methods Enzymol.* 375, 493-507. (i.e. formaldehyde fixation, (primary) restriction enzyme digestion, re-ligation of cross-linked DNA fragments and DNA purification). Briefly, a sample—such as cells, tissues or nuclei—is fixed using a cross-linking agent—such as formaldehyde. The primary restriction enzyme digestion is then performed such that the DNA is digested in the context of the cross-linked nucleus. Intramolecular ligation is then performed at low DNA concentrations (for example, about 3.7 ng/µl), which favours ligation between cross-linked DNA fragments (ie. intramolecular ligation) over ligation between non-cross-linked DNA fragments (ie. intermolecular or random ligation). Next, the cross links are reversed and the DNA can be purified. The 3C template that is yielded contains restriction fragments that are ligated because they were originally close in the nuclear space.

Since a primary restriction enzyme is used to digest the DNA prior to the intramolecular ligation step, an enzyme recognition site for the primary restriction enzyme will separate the first (target) nucleotide sequence and the nucleotide sequence that has been ligated. Accordingly, the primary recognition site is located between the first (target) nucleotide sequence and the ligated nucleotide sequence (ie. the ligated second sequence).

Nucleotide Sequence

The present invention involves the use of nucleotide sequences (eg. 3C templates, 4C templates, DNA templates, amplification templates, DNA fragments and genomic DNA), which may be available in databases.

The nucleotide sequence may be DNA or RNA of genomic, synthetic or recombinant origin e.g. cDNA. For example, recombinant nucleotide sequences may be prepared using a PCR cloning techniques. This will involve making a pair of primers flanking a region of the sequence which it is desired to clone, bringing the primers into contact with mRNA or cDNA obtained from, for example, a mammalian (eg. animal or human cell) or non-mammalian cell, performing a polymerase chain reaction (PCR) under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

The nucleotide sequence may be double-stranded or single-stranded whether representing the sense or antisense strand or combinations thereof.

For some aspects, it is preferred that the nucleotide sequence is single-stranded DNA—such as single stranded primers and probes.

For some aspects, it is preferred that the nucleotide sequence is double-stranded DNA—such as double stranded 3C and 4C templates.

For some aspects, it is preferred that the nucleotide sequence is genomic DNA—such as one or more genomic loci.

For some aspects, it is preferred that the nucleotide sequence is chromosomal DNA.

The nucleotide sequence may comprise a first (target) nucleotide sequence and/or a second nucleotide sequence.

The primary and secondary restriction enzyme recognition sites will be different to each other and will typically occur only once in the nucleotide sequence.

In one aspect, there is provided a circularised nucleotide sequence comprising a first nucleotide sequence and (eg. ligated to) a second nucleotide sequence separated (eg. divided or parted) by a primary and a secondary restriction enzyme recognition site, wherein said first nucleotide sequence is a target nucleotide sequence and said second nucleotide sequence is obtainable by cross-linking genomic DNA (eg. in vivo or in vitro). The primary and secondary restriction enzyme recognition sites will be different to each other and will typically occur only once in the nucleotide sequence.

In a further aspect, there is provided a circularised nucleotide sequence comprising a first nucleotide sequence and (eg. ligated to) a second nucleotide sequence separated (eg. divided or parted) by a primary and a secondary restriction enzyme recognition site, wherein said first nucleotide sequence is a target nucleotide sequence and wherein said first and second nucleotide sequences are obtainable by a process comprising the steps of: (a) cross-linking genomic DNA (eg. in vivo or in vitro); (b) digesting the cross-linked DNA with a primary restriction enzyme; (c) ligating the cross-linked nucleotide sequences; (d) reversing the cross linking; and (e) digesting the nucleotide sequences with a secondary restriction enzyme to circularise the nucleotide sequences.

Preferably, the second nucleotide sequence intersects (eg. bisects) the first (target) nucleotide sequence. Accordingly, the nucleotide sequence comprises the second nucleotide sequence, which separates the first (target) nucleotide sequence into two portions or fragments—such as approximately two equally sized portions or fragments. Typically, the portions or fragments will be at least about 16 nucleotides in length.

In a further aspect, there is provided a database of sequences of 6-50 basepairs that directly flank, and optionally include, the primary restriction enzyme recognition site of each target sequence included, and that can be used in the methods described herein to identify each target sequence.

In another aspect, there is provided a database of sequences of 12-50 basepairs that directly flank all primary restriction enzyme recognition sites in the genome and that can be used in the methods described herein to determine the genomic position of each of the captured sequences identified.

In another aspect, there is provided a database of sequences of 6-50 basepairs that directly flank, and optionally include, the relevant secondary restriction enzyme recognition site of each of the target sequences included, and that can be used in the methods described herein to identify each target sequence.

In another aspect, there is provided a database of sequences of 12-50 basepairs that directly flank all relevant secondary restriction enzyme recognition sites in the genome and that can be used in the methods described herein to determine the genomic position of each of the captured sequences identified.

First Nucleotide Sequence

The first nucleotide sequence is a target nucleotide sequence.

As used herein, the term "target nucleotide sequence" refers to the sequence that is used as a bait sequence in order to identify the one or more sequences to which it cross-links (eg. one or more nucleotide sequences of interest or one or more sequences of unknown nucleotide sequence composition).

The target nucleotide sequence is of known sequence.

Cross-linking is indicative that the target nucleotide sequence and sequence cross-linked thereto were originally close in the nuclear space. By determining the frequency by which sequences are close to each other, it is possible to understand, for example, the conformation of chromosomes and chromosomal regions in the spatial context of the nucleus (eg. in vivo or in vitro). Moreover, it is possible to understand the intricate structural organisations within the genome, for example, when enhancers or other transcriptional regulatory elements communicate with distant promoters located in cis or even in trans. Furthermore, it is even possible to understand the positioning of a given genomic region relative to nucleotide sequences present on the same chromosome (in cis) as well as to nucleotide sequences on other chromosomes (in trans). Thus, it is possible to map nucleotide sequences on different chromosomes that frequently share sites in the nuclear space. Furthermore, it is even possible to detect balanced and/or unbalanced genetic aberrations—such as balanced and/or unbalanced translocations, deletions, inversions, duplications and other genomic rearrangements (eg. deletions or translocations in one or more chromosomes). In this regard, genetic aberrations result in changes in the DNA-DNA interactions at the position that the change has occurred, which can be detected.

The first (target) nucleotide sequence in accordance with the present invention can be any sequence in which it is desired to determine the frequency of interaction in the nuclear space with one or more other sequences.

In one embodiment, the first (target) nucleotide sequence will be greater than about 350 bp in length since a secondary restriction enzyme is chosen that cuts the first (target) nucleotide sequence at about 350 bp or more from the primary restriction site. This may minimise a bias in circle formation due to topological constraints (Rippe et al. (2001) *Trends in Biochem. Sciences* 26, 733-40).

Suitably, the first (target) nucleotide sequence following amplification comprises at least about 32 bp by virtue of the fact that the minimum length of the at least two amplification primers used to amplify the second nucleotide sequence are about 16 bases each.

In a preferred embodiment, the first (target) nucleotide sequence may comprise completely or partially (eg. a fragment), or be close to (eg. in the proximity of), a promoter, an enhancer, a silencer, an insulator, a matrix attachment region, a locus control region, a transcription unit, an origin of replication, a recombination hotspot, a translocation breakpoint, a centromere, a telomere, a gene-dense region, a gene-poor region, a repetitive element, a (viral) integration site, a nucleotide sequence in which deletions and/or mutations are related to an effect (e.g. disease, physiological, functional or structural effect—such as an SNP (single nucleotide polymorphism), or nucleotide sequence(s) containing such deletions and/or mutations, or any sequence in which it is desired to determine the frequency of interaction in the nuclear space with other sequences.

As mentioned above, the first (target) nucleotide sequence may comprise completely or partially (eg. a fragment), or be close to (eg. in the proximity of) a nucleotide sequence in which genetic aberrations—such as deletions and/or mutations—are related to an effect (e.g. a disease). According to this embodiment of the invention the first (target nucleotide sequence) may therefore be a nucleotide sequence (eg. a gene or a locus), adjacent to (on the physical DNA template), or in the genomic region in which changes have been associated with or correlated to a disease—such as a genetic or congenital disease. In other words, the first (target) nucleotide sequence may be or may be chosen based on its association with a clinical phenotype. In a preferred embodiment, the changes are changes in one or more chromosomes and the disease may be as a consequence of, for example, one or more deletions, one or more translocations, one or more duplications, and/or one or more inversions etc therein. Non-limiting examples of such genes/loci are AML1, MLL, MYC, BCL, BCR, ABL1, immunoglobulin loci, LYL1, TAL1, TAL2, LMO2, TCRα/δ, TCRβ, HOX and other loci in various lymphoblastic leukemias.

Other examples are described in electronic databases—such as:
www.ncbi.nlm.nih.gov/entrez/
query.fcgi?db=cancerchromosomes
cgap.nci.nih.gov/Chromosomes/Mitelman
www.progenetix.net/progenetix/P14603437/ideogram.html
www.changbioscience.com/cytogenetics/
cyto1.p1?query=47,xy
www.possum.net.au/
www.1mdatabases.com/
www.wiley.com/legacy/products/subject/life/borgaonkar/index.html
www.ncbi.nlm.nih.gov/entrez/query.fcgi?db=OMIM
www.sanger.ac.uk/PostGenomics/decipher/
agserver01.azn.n1:8080/ecaruca/ecaruca.jsp.

Other examples are described in "Catalogue of Unbalanced Chromosome Aberrations in Man" 2nd edition. Albert Schinzel. Berlin: Walter de Gruyter, 2001. ISBN 3-11-011607-3.

In one embodiment, the term "adjacent" means "directly adjacent" such that there are no intervening nucleotides between two adjacent sequences.

In another embodiment, the term "adjacent" in the context of the nucleic acid sequence and the primary restriction enzyme recognition site means "directly adjacent" such that there are no intervening nucleotides between the nucleic acid sequence and the primary restriction enzyme recognition site.

Second Nucleotide Sequence

The second nucleotide sequence is obtainable, obtained, identified, or identifiable by cross-linking genomic DNA (eg. in vivo or in vitro).

The second nucleotide sequence (eg. nucleotide sequence of interest) becomes ligated to the first (target) nucleotide sequence after treating a sample with a cross-linking agent and digesting/ligating the cross-linked DNA fragments. Such sequences are cross-linked to the first (target) nucleotide sequence because they were originally close in the nuclear space and ligated to the first (target) nucleotide sequence because ligation conditions favour ligation between cross-linked DNA fragments (intramolecular) over random ligation events.

Diseases based on alterations—such as translocations, deletions, inversions, duplications and other genomic rearrangements—are generally caused by aberrant DNA-DNA interactions. 4C technology measures DNA-DNA interaction frequencies, which primarily are a function of the genomic site separation, ie. DNA-DNA interaction frequencies are inversely proportional to the linear distance (in kilobases) between two DNA loci present on the same physical DNA template (Dekker et al., 2002). Thus, alteration(s) which create new and/or physically different DNA templates, is accompanied by altered DNA-DNA interactions and this can be measured by 4C technology.

Suitably, the second nucleotide sequence is at least 40 base pairs.

Cross-linking agents—such as formaldehyde—can be used to cross link proteins to other neighbouring proteins and nucleic acid. Thus, two or more nucleotide sequences can be cross-linked only via proteins bound to (one of) these nucleotide sequences. Cross-linking agents other than formaldehyde can also be used in accordance with the present invention, including those cross-linking agents that directly cross link nucleotide sequences. Examples of agents that cross-link DNA include, but are not limited to, UV light, mitomycin C, nitrogen mustard, melphalan, 1,3-butadiene diepoxide, cis diaminedichloroplatinum(II) and cyclophosphamide.

Suitably, the cross-linking agent will form cross-links that bridge relatively short distances—such as about 2 Å—thereby selecting intimate interactions that can be reversed.

Cross-linking may be performed by, for example, incubating the cells in 2% formaldehyde at room temperature—such as by incubating $1\times10^7$ cells in 10 ml of DMEM-10% FCS supplemented with 2% formaldehyde for 10 min at room temperature.

Primary Restriction Enzyme

As used herein, the term "primary restriction enzyme" refers to a first restriction enzyme that is used to digest the cross-linked DNA.

The primary restriction enzyme will be chosen depending on the type of target sequence (eg. locus) to be analysed. It is desirable that preliminary experiments are performed to optimise the digestion conditions.

The primary restriction enzyme may be selected from restriction enzymes recognising at least 8 bp sequences or more of DNA. The primary restriction enzyme may be selected from restriction enzymes recognising at least 7 bp sequences or more of DNA. The primary restriction enzyme may be selected from restriction enzymes recognising at least 6 bp sequences or more of DNA. For some embodiments, the primary restriction enzyme may be selected from restriction enzymes recognising a 4 bp and/or 5 bp sequence of DNA.

Using less frequent cutters will increase the genomic distance captured (covered) by each bait.

Restriction enzymes that recognise 6 bp sequences of DNA include, but are not limited to, AcII, HindIII, SspI, BspLU11I, AgeI, MluI, SpeI, BglII, Eco47III, StuI, ScaI, ClaI, AvaIII, VspI, MfeI, PmaCI, PvuII, NdeI, NcoI, SmaI, SacII, AvrII, PvuI, XmaIII, SplI, XhoI, PstI, AflII, EcoRI, AatII, SacI, EcoRV, SphI, NaeI, BsePI, NheI, BamHI, NarI, ApaI, KpnI, SnaI, SaltApaLI, HpaI, SnaBI, BspHI, BspMII, NruI, XbaI, BclI, MstI, BalI, Bsp1407I, PsiI, AsuII and AhaIII.

Restriction enzymes that recognise more than a 6 bp sequence of DNA include, but are not limited to BbvC I, AscI, AsiS I, Fse I, Not I, Pac I, Pme I, Sbf I, SgrA I, Swa I, Sap I, Cci NI, FspA I, Mss I, Sgf I, Smi I, Srf I and Sse8387 I.

For some aspects of the present invention, in the case of restriction enzymes recognizing 6 bp sequences, BglII, HindIII or EcoRI are preferred.

Restriction enzymes that recognise 4 or 5 bp sequences of DNA include, but are not limited to, TspEI, MaeII, AluI, NlaIII, HpaII, FnuDII, MaeI, DpnI, MboI, HhaI, HaeIII, RsaI, TaqI, CviRI, MseI, Sth132I, AciI, DpnII, Sau3AI and MnlI. In one embodiment, the secondary restriction enzyme is NlaIII and/or DpnII.

The term "primary restriction enzyme recognition site" refers to the site in a nucleotide sequence that is recognised and cleaved by the primary restriction enzyme.

For some embodiments, the restriction enzyme does not digest repetitive DNA or DNA that is relatively under-represented in repetitive DNA. This may increase the number of interpretable reads.

Secondary Restriction Enzyme

As used herein, the term "secondary restriction enzyme" refers to a second restriction enzyme that is optionally used after primary restriction enzyme digestion, ligation of cross-linked DNA, de-cross-linking and (optional) DNA purification. In one embodiment, the secondary restriction enzyme is used to provide defined DNA ends to the nucleotide sequences of interest, which allows for the ligation of sequences of known nucleotide composition to the secondary restriction enzyme recognition sites that flank the nucleotide sequences of interest.

In one embodiment, ligation of sequences of known nucleotide composition to the secondary restriction enzyme recognition sites that flank (eg. are at each side or end of) the nucleotide sequences of interest involves ligation under diluted conditions to favour the intra-molecular ligation between the secondary restriction enzyme recognition sites that flank target nucleotide sequences and the linked nucleotide sequences of interest. This effectively results in the formation of DNA circles in which known target nucleotide sequences flank unknown sequences of interest.

In another embodiment, ligation of sequences of known nucleotide composition to the secondary restriction enzyme recognition sites that flank (eg. are at each side or end of) the nucleotide sequences of interest involves the addition of unique DNA sequences of known nucleotide composition, followed by ligation under conditions that favour inter-molecular ligation between the secondary restriction enzyme recognition sites that flank the nucleotide sequences of interest and introduced unique DNA sequences of known nucleotide composition.

In one embodiment, the secondary restriction enzyme is chosen such that no secondary restriction enzyme sites are within about 350 bp (eg. 350-400 bp) of the primary restriction site.

In another embodiment, the secondary restriction enzyme is chosen such that the same secondary restriction enzyme site is likely to be located in the ligated nucleotide sequence (ie. the ligated cross-linked sequence). Since the ends of the first (target) nucleotide sequence and the ligated nucleotide sequence may be compatible cohesive (or blunt) ends, the sequences may even be ligated in order to circularise the DNA. Accordingly, the digestion step is followed by ligation under diluted conditions that favour intra-molecular interactions and optional circularisation of the DNA via the compatible ends.

Preferably, the secondary restriction enzyme recognition site is a 4 or 5 bp nucleotide sequence recognition site. Enzymes that recognise 4 or 5 bp sequences of DNA include, but are not limited to, TspEI, MaeII, AluI, NlaIII, HpaII, FnuDII, MaeI, DpnI, MboI, HhaI, HaeIII, RsaI, TaqI, CviRI, MseI, Sth132I, AciI, DpnII, Sau3AI and MnlI.

In a preferred embodiment, the secondary restriction enzyme is NlaIII and/or DpnII.

The term "secondary restriction enzyme recognition site" refers to the site in the nucleotide sequence that is recognised and cleaved by the secondary restriction enzyme.

Following the digestion with the secondary restriction enzyme, a further ligation reaction is performed. In one embodiment, this ligation reaction links DNA sequences of known nucleotide sequence composition to the secondary restriction enzyme digestion site of the one or more sequences that are ligated to the target nucleotide sequence.

For some embodiments, the method excludes the step of digesting the nucleotide sequences with a secondary restriction enzyme.

For some embodiments, the method excludes ligating one or more DNA sequences of known nucleotide composition to the available secondary restriction enzyme digestion site(s) that flank the one or more nucleotide sequences of interest.

Tertiary Restriction Enzyme

As used herein, the term "tertiary restriction enzyme" refers to a third restriction enzyme that can be optionally used after the secondary restriction enzyme step in order to linearise circularised DNA prior to amplification.

Preferably, the tertiary restriction enzyme is an enzyme that recognises a 6 bp or more nucleotide recognition site.

Preferably, the tertiary restriction enzyme digests the first (target) nucleotide sequence between the primary and secondary restriction enzyme recognition sites. As will be understood by a skilled person, it is desirable that the tertiary restriction enzyme does not digest the first (target) nucleotide sequence too close to the primary and secondary restriction enzyme recognition sites such that the amplification primers can no longer hybridise. Accordingly, it is preferred that the tertiary restriction enzyme recognition site is located at least the same distance away from the primary and secondary restriction enzyme recognition sites as the length of the primer to be used such that the amplification primer(s) can still hybridise.

In a preferred embodiment, the tertiary restriction enzyme is one that recognises a 6-bp sequence of DNA.

The term "tertiary restriction enzyme recognition site" refers to the site in the nucleotide sequence that is recognised and cleaved by the tertiary restriction enzyme.

Recognition Site

Restriction endonucleases are enzymes that cleave the sugar-phosphate backbone of DNA. In most practical settings, a given restriction enzyme cuts both strands of duplex DNA within a stretch of just a few bases. The substrates for restriction enzymes are sequences of double-stranded DNA called recognition sites/sequences.

The length of restriction recognition sites varies, depending on the restriction enzyme that is used. The length of the recognition sequence dictates how frequently the enzyme will cut in a sequence of DNA.

By way of example, a number of restriction enzymes recognise a 4 bp sequence of DNA. The sequences and the enzyme that recognise the 4 bp sequence of DNA include, but are not limited to, AATT (TspEI), ACGT (MaeII), AGCT (AluI), CATG (NlaIII), CCGG (HpaII), CGCG (FnuDII), CTAG (MaeI), GATC (DpnI, DpnII, Sau3AI & MboI), GCGC (HhaI), GGCC (HaeIII), GTAC (RsaI), TCGA (TaqI), TGCA (CviRI), TTAA (MseI), CCCG (Sth132I), CCGC (AciI) and CCTC (MnlI)

By way of further example, a number of restriction enzymes recognise a 6 bp sequence of DNA. The sequences and the enzyme that recognise the 6 base-pair by sequence of DNA include, but are not limited to, AACGTT (AclI), AAGCTT (HindIII), AATATT (SspI), ACATGT (BspLU11I), ACCGGT (AgeI), ACGCGT (MluI), ACTAGT (SpeI), AGATCT (BglII), AGCGCT (Eco47III), AGGCCT (StuI), AGTACT (ScaI), ATCGAT (ClaI) ATGCAT (AvaIII), ATTAAT (VspI), CAATTG (MfeI), CACGTG (PmaCI), CAGCTG (PvuII), CATATG (NdeI), CCATGG (NcoI), CCCGGG (SmaI), CCGCGG (SacII), CCTAGG (AvrII), CGATCG (PvuI), CGGCCG (XmaIII), CGTACG (SplI), CTCGAG (XhoI), CTGCAG (PstI), CTTAAG (AflII), GAATTC (EcoRI), GACGTC (AatII), GAGCTC (SacI), GATATC (EcoRV), GCATGC (SphI), GCCGGC (NaeI), GCGCGC (BsePI), GCTAGC (NheI), GGATCC (BamHI), GGCGCC (NarI), GGGCCC (ApaI), GGTACC (KpnI), GTATAC (SnaI), GTCGAC (SalI), GTGCAC (ApaLI), GTTAAC (HpaI), TACGTA (SnaBI), TCATGA (BspHI), TCCGGA (BspMII), TCGCGA (NruI), TCTAGA (XbaI), TGATCA (BclI), TGCGCA (MstI), TGGCCA (BalI), TGTACA (Bsp1407I), TTATAA (PsiI), TTCGAA (AsuII) and TTTAAA (AhaIII).

By way of further example, a number of restriction enzymes recognise a 7 bp sequence of DNA. The sequences and the enzyme that recognise the 7 bp sequence of DNA include, but are not limited to CCTNAGG (SauI), GCTNAGC (EspI), GGTNACC BstEII and TCCNGGA PfoI.

By way of further example, a number of restriction enzymes recognise an 8 bp sequence of DNA. The sequences and the enzyme that recognise the 8 bp sequence of DNA include, but are not limited to ATTTAAAT (SwaI), CCTGCAGG (Sse8387I), CGCCGGCG (Sse232I), CGTCGACG (SgrDI), GCCCGGGC (SrfI), GCGATCGC (SgfI), GCGGCCGC (NotI), GGCCGGCC (FseI), GGCGCGCC (AscI), GTTAAAC (PmeI) and TTAATTAA (PacI).

A number of these enzymes contain the sequence CG that may be methylated in vivo. A number of restriction enzymes are sensitive to this methylation and will not cleave the methylated sequence, e.g. HpaII will not cleave the sequence $CC^mGG$ whereas its isoschizomer MspI is insensitive to this modification and will cleave the methylated sequence. Accordingly, in some instances the eukaryotic methylation sensitive enzymes are not used.

In one embodiment, a recognition site is a digestion site.

In one embodiment, a restriction enzyme recognition site is a restriction enzyme digestion site.

Circularising

In accordance with one embodiment of the present invention, the material for 4C is prepared by creating DNA circles by digesting the 3C template with a secondary restriction enzyme, followed by ligation.

Preferably, a secondary restriction enzyme is chosen that cuts the first (target) nucleotide sequence at greater than about 350 bp (eg. 350-400 bp) from the primary restriction site. Advantageously, this minimises a bias in circle formation due to topological constraints (Rippe et al. (2001) *Trends in Biochem. Sciences* 26, 733-40).

Preferably, the secondary restriction enzyme is a frequent cutter recognising a 4 or a 5 bp restriction enzyme recognition site. Thus it is possible to obtain the smallest restriction fragments for equal amplification efficiencies of all ligated fragments during amplification.

Prior to the secondary restriction enzyme digest and ligation, the DNA template will comprise one secondary enzyme recognition site in the first (target) nucleotide sequence located at greater than about 350-400 bp from the primary restriction site and another secondary enzyme recognition site located in the nucleotide sequence that has been ligated (ie in the second nucleotide sequence).

Preferably, the secondary restriction enzyme digestion step is performed for more than 1 hour to overnight and followed by heat-inactivation of the enzyme.

Preferably, the DNA in this reaction mixture is purified using conventional methods/kits that are known in the art.

Following the secondary restriction enzyme digestion step, a secondary restriction enzyme site will be located at greater than 350-400 bp from the primary restriction site in the first (target) nucleotide sequence and another secondary restriction enzyme site will be located in the ligated nucleotide sequence (ie. the second nucleotide sequence). Since the ends of the first (target) nucleotide sequence and the ligated nucleotide sequence have compatible ends, the sequences can be ligated in order to circularise the DNA.

The digestion step is then followed by ligation under diluted conditions that favour intra-molecular interactions and circularisation of the DNA via the compatible ends.

Preferably, the ligation reaction is performed at a DNA concentration of about 1-5 ng/µl.

Preferably, the ligation reaction is performed for more than 1 hr (eg. 2, 3, 4 or more hrs) at about 16-25° C.

Accordingly, following the ligation reaction, circularised DNA may be prepared. The circularised DNA will comprise the recognition sites for at least the secondary restriction enzyme or the primary and the secondary restriction enzymes. In circularised DNA containing the first (target) nucleotide sequence, the primary restriction enzyme recognition site and the secondary restriction enzyme recognition sites will define the ends of the first (target) nucleotide sequence and the ligated nucleotide sequence (ie. the second nucleotide sequence). Accordingly the first (target) nucleotide sequence and the ligated nucleotide sequence are separated (eg. divided) by the primary restriction enzyme recognition site and the secondary restriction enzyme recognition site.

Amplification

One or more amplification reactions may be performed in order to amplify the 4C DNA templates.

DNA amplification may be performed using a number of different methods that are known in the art. For example, DNA can be amplified using the polymerase chain reaction (Saiki et al., 1988); ligation mediated PCR, Qb replicase amplification (Cahill, Foster and Mahan, 1991; Chetverin and Spirin, 1995; Katanaev, Kurnasov and Spirin, 1995); the ligase chain reaction (LCR) (Landegren et al., 1988; Barany, 1991); the self-sustained sequence replication system (Fahy, Kwoh and Gingeras, 1991) and strand displacement amplification (Walker et al., 1992).

Suitably, DNA is amplified using PCR. "PCR" refers to the method of K. B. Mullis U.S. Pat. Nos. 4,683,195, 4,683,202, and 4,965,188 that describe a method for increasing the concentration of a segment of a nucleotide sequence in a mixture of genomic DNA without cloning or purification.

In one embodiment, inverse PCR is used. Inverse PCR (IPCR) (described by Ochman et al (1988) *Genetics* 120(3), 621-3) is a method for the rapid in vitro amplification of DNA sequences that flank a region of known sequence. The method uses the polymerase chain reaction (PCR), but it has the primers oriented in the reverse direction of the usual orientation. The template for the reverse primers is a restriction fragment that has been ligated upon itself to form a circle. Inverse PCR has many applications in molecular genetics, for example, the amplification and identification of sequences flanking transposable elements. To increase the efficiency and reproducibility of the amplification it is preferred that the DNA circles are linearised before amplification using a tertiary restriction enzyme. Preferably, a tertiary restriction enzyme that is a 6 bp or more cutter is used. Preferably, the tertiary restriction enzyme cuts the first (target) nucleotide sequence between the primary and secondary restriction enzyme sites.

Digestion of the 3C template with the secondary restriction enzyme, optional circularisation, ligation (eg. ligation under diluted conditions) and optional linearisation of first (target) nucleotide sequence-containing circles yields a DNA template for amplification ("4C DNA template").

For the amplification step, at least two oligonucleotide primers are used in which each primer hybridises to a DNA sequence that flanks the nucleotide sequences of interest. In a preferred embodiment, at least two oligonucleotide primers are used in which each primer hybridises to the target sequence flanking the nucleotide sequences of interest.

In one embodiment, the term "flank" in the context of primer hybridisation means that at least one primer hybridises to a DNA sequence adjacent one end (eg. the 5' end) of the nucleotide sequence of interest and at least one primer hybridises to a DNA sequence at the other end (eg. the 3' end) of the nucleotide sequence of interest. Preferably, at least one forward primer hybridises to a DNA sequence adjacent one end (eg. the 5' end) of the nucleotide sequence of interest and at least one reverse primer hybridises to a DNA sequence at the other end (eg. the 3' end) of the nucleotide sequence of interest.

In a preferred embodiment, the term "flank" in the context of primer hybridisation means that at least one primer hybridises to a target sequence adjacent one end (eg. the 5' end) of the nucleotide sequence of interest and at least one primer hybridises to a target sequence at the other end (eg. the 3' end) of the nucleotide sequence of interest. Preferably, at least one forward primer hybridises to a target sequence adjacent one end (eg. the 5' end) of the nucleotide sequence of interest and at least one reverse primer hybridises to a target sequence at the other end (eg. the 3' end) of the nucleotide sequence of interest.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

Suitably, the primers will be at least 15, preferably at least 16, 17, 18, 19 or 20, for example at least 25, 30 or 40 nucleotides in length. Preferably, the amplification primers are from 16 to 30 nucleotides in length.

Preferably, the primers are designed to be as close as possible to the primary and secondary restriction enzyme recognition sites that separate the first (target) nucleotide sequence and the second (captured) nucleotide sequence. The primers may be designed such that they are within about 100 nucleotides—such as about 90, 80, 70, 60, 50, 40, 30, 20, 10, 9, 8, 7, 6, 5, 4, 3, 2 or 1 nucleotide(s) away from the primary and secondary restriction enzyme recognition sites.

Suitably, the primers may be designed such that they partially or completely overlap the primary and secondary restriction enzyme recognition sites.

Suitably, the amplification primers are designed such that their 3' ends face outwards towards the second nucleotide sequence.

In one embodiment, the amplification may be combined with the addition of additional sequences to the ends of the amplified products. Preferably, these additional sequences are adapter sequences required for high-throughput sequencing. Suitably, primers contain an overhang (eg. a 5' overhang). Suitably the overhang adds part of, or the complete adapter sequence required for high-throughput sequencing. Suitably, primers contain an overhang (eg. a 5' overhang) that adds part of, or the complete sequence used to prime the sequencing reaction in high-throughput sequencing. Accordingly, in one embodiment, the primers overlap partially or completely with the primary and/or secondary restriction enzyme recognition sites with the adapter and sequence-priming sequences added as 5' overhangs to the primer. In addition or in the alternative, the primers contain a conjugated moiety (eg. biotin) that allows subsequent separation of PCR products from the genomic 4C template.

If the amplification method that is used is inverse PCR, then it is preferred that the amplification reactions are carried out on about 100-400 ng of DNA of 4C template (per about 50 μl PCR reaction mix) or other amounts of DNA for which replicate PCR reactions give reproducible results (see FIG. 1) and include a maximum number of ligation events per PCR reaction.

Preferably, the inverse PCR amplification reaction is performed using the Expand Long Template PCR System (Roche), using Buffer 1 according to the manufacturer's instructions.

Sample

The term "sample" as used herein, has its natural meaning. A sample may be any physical entity comprising DNA that is or is capable of being cross-linked. The sample may be or may be derived from biological material.

The sample may be or may be derived from one of more entities—such as one or more cells, one or more nuclei, or one or more tissue samples. The entities may be or may be derivable from any entities in which DNA—such as chromatin—is present. The sample may be or may be derived from one or more isolated cells or one or more isolated tissue samples, or one or more isolated nuclei.

The sample may be or may be derived from living cells and/or dead cells and/or nuclear lysates and/or isolated chromatin.

The sample may be or may be derived from diseased and/or non-diseased subjects.

The sample may be or may be derived from a subject that is suspected to be suffering from a disease.

The sample may be or may be derived from a subject that is to be tested for the likelihood that they will suffer from a disease in the future.

The sample may be or may be derived from viable or non-viable patient material.

The fixation of cells and tissues for use in preparing the 3C template is described in detail in Splinter et al., (2004) *Methods Enzymol.* 375, 493-507.

Label

Preferably, the nucleotide sequences (eg. amplified 4C DNA templates, primers or probes etc.) are labelled in order to assist in their downstream applications—such as array hybridisation. By way of example, the 4C DNA templates may be labelled using random priming or nick translation.

A wide variety of labels (eg. reporters) may be used to label the nucleotide sequences described herein, particularly during the amplification step. Suitable labels include radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Additional labels include but are not limited to β-galactosidase, invertase, green fluorescent protein, luciferase, chloramphenicol, acetyltransferase, β-glucuronidase, exoglucanase and glucoamylase. Fluorescent labels may also be used, as well as fluorescent reagents specifically synthesised with particular chemical properties. A wide variety of ways to measure fluorescence are available. For example, some fluorescent labels exhibit a change in excitation or emission spectra, some exhibit resonance energy transfer where one fluorescent reporter looses fluorescence, while a second gains in fluorescence, some exhibit a loss (quenching) or appearance of fluorescence, while some report rotational movements.

In order to obtain sufficient material for labelling, multiple amplifications may be pooled, instead of increasing the number of amplification cycles per reaction. Alternatively, labelled nucleotides can be incorporated in to the last cycles of the amplification reaction (e.g. 30 cycles of PCR (no label)+10 cycles of PCR (plus label)).

Array

In a particularly advantageous embodiment, the 4C DNA templates that are prepared in accordance with the methods described herein can be hybridised to an array. Accordingly, array (eg. micro-array) technology can be used to identify nucleotide sequences—such as genomic fragments—that frequently share a nuclear site with a first (target) nucleotide sequence.

Existing arrays—such as expression and genomic arrays—can be used in accordance with the present invention. However, the present invention also seeks to provide novel arrays (eg. DNA arrays) as described herein.

An "array" is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" includes those libraries of nucleic acids which can be prepared by spotting nucleic acids of essentially any length (e.g., from 1 to about 1000 nucleotide monomers in length) onto a substrate.

Array technology and the various techniques and applications associated with it is described generally in numerous textbooks and documents. These include Lemieux et al., 1998, *Molecular Breeding* 4, 277-289, Schena and Davis. *Parallel Analysis with Biological Chips.* in PCR Methods Manual (eds. M. Innis, D. Gelfand, J. Sninsky), Schena and Davis, 1999, *Genes, Genomes and Chips.* In *DNA Microarrays: A Practical Approach* (ed. M. Schena), Oxford University Press, Oxford, UK, 1999), *The Chipping Forecast (Nature Genetics* special issue; January 1999 Supplement), Mark Schena (Ed.), *Microarray Biochip Technology*, (Eaton Publishing Company), Cortes, 2000, *The Scientist* 14[17]:25, Gwynne and Page, *Microarray analysis: the next revolution in molecular biology, Science,* 1999 August 6; and Eakins and Chu, 1999, *Trends in Biotechnology,* 17, 217-218.

Array technology overcomes the disadvantages with traditional methods in molecular biology, which generally work on a "one gene in one experiment" basis, resulting in low throughput and the inability to appreciate the "whole picture" of gene function. Currently, the major applications for array technology include the identification of sequence (gene/gene mutation) and the determination of expression level (abundance) of genes. Gene expression profiling may make use of array technology, optionally in combination with proteomics techniques (Celis et al, 2000, *FEBS Lett,* 480(1):2-16; Lockhart and Winzeler, 2000, Nature 405(6788):827-836; Khan et al., 1999, 20(2):223-9). Other applications of array technology are also known in the art; for example, gene discovery, cancer research (Marx, 2000, Science 289: 1670-1672; Scherf, et al, 2000, Nat Genet; 24(3):236-44; Ross et al, 2000, Nat Genet. 2000 March; 24(3):227-35), SNP analysis (Wang et al, 1998, Science, 280(5366):1077-82), drug discovery, pharmacogenomics, disease diagnosis (for example, utilising microfluidics devices: Chemical & Engineering News, Feb. 22, 1999, 77(8):27-36), toxicology (Rockett and Dix (2000), *Xenobiotica,* 30(2):155-77; Afshari et al., 1999, Cancer Res1; 59(19):4759-60) and toxicogenomics (a hybrid of functional genomics and molecular toxicology).

In general, any library may be arranged in an orderly manner into an array, by spatially separating the members of the library. Examples of suitable libraries for arraying include nucleic acid libraries (including DNA, cDNA, oligonucleotide, etc libraries), peptide, polypeptide and protein libraries, as well as libraries comprising any molecules, such as ligand libraries, among others.

The samples (e.g., members of a library) are generally fixed or immobilised onto a solid phase, preferably a solid substrate, to limit diffusion and admixing of the samples. In a preferred embodiment, libraries of DNA binding ligands may be prepared. In particular, the libraries may be immobilised to a substantially planar solid phase, including membranes and non-porous substrates such as plastic and glass. Furthermore, the samples are preferably arranged in such a way that indexing (i.e., reference or access to a particular sample) is facilitated. Typically the samples are applied as spots in a grid formation. Common assay systems may be adapted for this purpose. For example, an array may be immobilised on the surface of a microplate, either with multiple samples in a well, or with a single sample in each well. Furthermore, the solid substrate may be a membrane, such as a nitrocellulose or nylon membrane (for example, membranes used in blotting experiments). Alternative substrates include glass, or silica based substrates. Thus, the samples are immobilised by any suitable method known in the art, for example, by charge interactions, or by chemical coupling to the walls or bottom of the wells, or the surface of the membrane. Other means of arranging and fixing may be used, for example, pipetting, drop-touch, piezoelectric means, ink-jet and bubblejet technology, electrostatic application, etc. In the case of silicon-based chips, photolithography may be utilised to arrange and fix the samples on the chip.

The samples may be arranged by being "spotted" onto the solid substrate; this may be done by hand or by making use of robotics to deposit the sample. In general, arrays may be described as macroarrays or microarrays, the difference being the size of the sample spots. Macroarrays typically contain sample spot sizes of about 300 microns or larger and may be easily imaged by existing gel and blot scanners. The sample spot sizes in microarrays are typically less than 200 microns in diameter and these arrays usually contain thousands of spots. Thus, microarrays may require specialized robotics and imaging equipment, which may need to be custom made. Instrumentation is described generally in a review by Cortese, 2000, *The Scientist* 14[11]:26.

Techniques for producing immobilised libraries of DNA molecules have been described in the art. Generally, most prior art methods described how to synthesise single-stranded nucleic acid molecule libraries, using for example masking techniques to build up various permutations of sequences at the various discrete positions on the solid substrate. U.S. Pat. No. 5,837,832 describes an improved method for producing DNA arrays immobilised to silicon substrates based on very large scale integration technology. In particular, U.S. Pat. No. 5,837,832 describes a strategy called "tiling" to synthesise specific sets of probes at spatially-defined locations on a substrate which may be used to produced the immobilised DNA libraries of the present invention. U.S. Pat. No. 5,837,832 also provides references for earlier techniques that may also be used.

Arrays may also be built using photo deposition chemistry.

Arrays of peptides (or peptidomimetics) may also be synthesised on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a target or probe) and reactive library members occur is determined, thereby identifying the sequences of the reactive library members on the basis of spatial location. These methods are described in U.S. Pat. No. 5,143,854; WO90/15070 and WO92/10092; Fodor et al. (1991) *Science*, 251: 767; Dower and Fodor (1991) *Ann. Rep. Med. Chem.*, 26: 271.

To aid detection, labels are typically used (as discussed above)—such as any readily detectable reporter, for example, a fluorescent, bioluminescent, phosphorescent, radioactive, etc reporter. Such reporters, their detection, coupling to targets/probes, etc are discussed elsewhere in this document. Labelling of probes and targets is also disclosed in Shalon et al., 1996, *Genome Res* 6(7):639-45.

Specific examples of DNA arrays are as follow:

Format I: probe cDNA (500-5,000 bases long) is immobilized to a solid surface such as glass using robot spotting and exposed to a set of targets either separately or in a mixture. This method is widely considered as having been developed at Stanford University (Ekins and Chu, 1999, *Trends in Biotechnology*, 1999, 17, 217-218).

Format II: an array of oligonucleotides (20-25-mer oligos, preferably, 40-60 mer oligos) or peptide nucleic acid (PNA) probes are synthesised either in situ (on-chip) or by conventional synthesis followed by on-chip immobilization. The array is exposed to labelled sample DNA, hybridised, and the identity/abundance of complementary sequences are determined. Such a DNA chip is sold by Affymetrix, Inc., under the GeneChip® trademark. Agilent and Nimblegen also provide suitable arrays (eg. genomic tiling arrays).

Examples of some commercially available microarray formats are set out in Table 1 below (see also Marshall and Hodgson, 1998, *Nature Biotechnology*, 16(1), 27-31).

TABLE 1

Examples of currently available hybridization microarray formats

| Company | Product name | Arraying method | Hybridization step | Readout |
|---|---|---|---|---|
| Affymetrix, Inc., Santa Clara, California | GeneChip ® | In situ (on-chip) photolithographic synthesis of ~20-25-mer oligos onto silicon wafers, which are diced into 1.25 cm² or 5.25 cm² chips | 10,000-260,000 oligo features probed with labeled 30-40 nucleotide fragments of sample cDNA or antisense RNA | Fluorescence |
| Brax, Cambridge, UK | | Short synthetic oligo synthesized off-chip | 1000 oligos on a "universal chip" probed with tagged nucleic acid | Mass spectrometry |
| Gene Logic, Inc., Columbia, Maryland | READS ™ | | | |
| Genometrix Inc., The | Universal Arrays ™ | | | |

TABLE 1-continued

Examples of currently available hybridization microarray formats

| Company | Product name | Arraying method | Hybridization step | Readout |
|---|---|---|---|---|
| Woodlands, Texas GENSET, Paris, France | | | | |
| Hyseq Inc., Sunnyvale, California | HyChip ™ | 500-2000 nt DNA samples printed onto 0.6 cm$^2$ (HyGnostics) or ~18 cm$^2$ (Gene Discovery) membranes | 64 sample cDNA spots probed with 8,000 7-mer oligos (HyGnostics) or <=55,000 sample cDNA spots probed with 300 7-mer oligo (Gene Discovery) | Radioisotope |
| | | Fabricated 5-mer oligos printed as 1.15 cm$^2$ arrays onto glass (HyChip) | Universal 1024 oligo spots probed 10 kb sample cDNAs, labeled 5-mer oligo, and ligase | Fluorescence |
| Incyte Pharmaceuticals, Inc., Palo Alto, California | GEM | Piezoelectric printing for spotting PCR fragments and on-chip synthesis of oligos | <=1000 (eventually 10,000) oligo/PCR fragment spots probed with labeled RNA | Fluorescence and radioisotope |
| Molecular Dynamics, Inc., Sunnyvale, California | Storm ® FluorImager ® | 500-5000 nt cDNAs printed by pen onto ~10 cm$^2$ on glass slide | ~10,000 cDNA spots probed with 200-400 nt labeled sample cDNAs | Fluorescence |
| Nanogen, San Diego, California | Semiconductor Microchip | Prefabricated ~20-mer oligos, captured onto electroactive spots on silicon wafers, which are diced into <=1 cm$^2$ chips | 25, 64, 400 (and eventually 10,000) oligo spots polarized to enhance hybridization to 200-400 nt labeled sample cDNAs | Fluorescence |
| Protogene Laboratories, Palo Alto, California | | On-chip synthesis of 40-50-mer oligos onto 9 cm$^2$ glass chip via printing to a surface-tension array | <=8,000 oligo spots probed with 200-400 nt labeled sample nucleic acids | Fluorescence |
| Sequenom, Hamburg, Germany, and San Diego, California | MassArray SpectroChip | Off-set printing of array; around 20-25-mer oligos | 250 locations per SpectroChip interrogated by laser desorbtion and mass spectrometry | Mass spectrometry |
| Synteni, Inc., Fremont, California | UniGEM ™ | 500-5,000 nt cDNAs printed by tip onto ~4 cm$^2$ glass chip | <=10,000 cDNA spots probed with 200-400 nt labeled sample cDNAs | Fluorescence |
| Nimblegen Systems Inc., Madison | *Homo sapiens* Whole-Genome 60 mer Microarray | 38,000 transcripts with 5 probes per gene 17.4 mm × 13 mm | | 5-micron scanning platform |
| The German Cancer Institute, Heidelberg, Germany | | Prototypic PNA macrochip with on-chip synthesis of probes using f-moc or t-moc chemistry | Around 1,000 spots on a 8 × 12 cm chip | Fluorescence/mass spectrometry |

In order to generate data from array-based assays a signal is detected that signifies the presence of or absence of hybridisation between a probe and a nucleotide sequence. The present invention further contemplates direct and indirect labelling techniques. For example, direct labelling incorporates fluorescent dyes directly into the nucleotide sequences that hybridise to the array associated probes (e.g., dyes are incorporated into nucleotide sequence by enzymatic synthesis in the presence of labelled nucleotides or PCR primers). Direct labelling schemes yield strong hybridisation signals, typically using families of fluorescent dyes with similar chemical structures and characteristics, and are simple to implement. In preferred embodiments comprising direct labelling of nucleic acids, cyanine or alexa analogs are utilised in multiple-fluor comparative array analyses. In other embodiments, indirect labelling schemes can be utilised to incorporate epitopes into the nucleic acids either prior to or after hybridisation to the microarray probes. One or more staining procedures and reagents are used to label the hybridised complex (eg., a fluorescent molecule that binds to the epitopes, thereby providing a fluorescent signal by virtue of the conjugation of dye molecule to the epitope of the hybridised species).

Data analysis is also an important part of an experiment involving arrays. The raw data from an array experiment typically are images, which need to be transformed into matrices—tables where rows represent for example genes, columns represent for example various samples such as tissues or experimental conditions, and numbers in each cell for example characterise the expression of a particular sequence (preferably, a second sequence that has ligated to the first (target) nucleotide sequence) in the particular sample. These matrices have to be analysed further, if any knowledge about the underlying biological processes is to be extracted. Methods of data analysis (including supervised and unsupervised data analysis as well as bioinformatics approaches) are disclosed in Brazma and Vilo J (2000) FEBS Lett 480(1):17-24.

As described herein the one or more nucleotide sequences (eg. the DNA template) that are labelled and subsequently hybridised to an array comprises a nucleotide sequence that is enriched for small stretches of sequences with a distinct signature ie. spanning the nucleotide sequence between the primary restriction enzyme recognition site that was ligated during the 3C procedure to the first (target) nucleotide sequence, and their respective neighbouring secondary restriction enzyme recognition sites.

A single array may comprise multiple (eg. two or more) bait sequences.

Chromsome Map

There is further described herein a method involving the characterization of DNA fragments cross-linked as a consequence of their spatial or physical proximity, for the purpose of the (re)construction of chromosome maps (eg. linear chromosome maps) and the diagnostic identification of changes in these chromosome maps.

Advantageously, such techniques can be applied for diagnostic purposes—such as to reconstruct physical chromosome maps and to identify changes in these maps as a consequence of genomic rearrangements.

The methodology can also be used to identify (natural) genomic variation that is not necessarily associated with disease but may predispose a subject to a certain trait (eg. a mental or behavioural trait).

In one aspect, there is provided a method for constructing at least one linear chromosome map of an individual comprising the steps of: (a) providing a nucleic acid sample from said individual; (b) cross-linking the nucleic acid in said sample; (c) digesting the nucleic aid with a primary restriction enzyme; (d) ligating the cross linked nucleotide sequences; (e) reversing the cross linking; (f) analyzing the ligation products; (g) constructing at least one linear chromosome map; and (h) identifying one or more genomic rearrangements in the linear chromosome map of said individual.

In a further aspect, there is provided a method for diagnosing a disease or identifying a trait caused by one or more genomic rearrangements in a chromosome comprising the steps of: (a) digesting a sample of cross-linked DNA with a primary restriction enzyme; (b) ligating the cross linked nucleotide sequences; (c) reversing the cross linking; (d) analysing the ligation products; (e) constructing at least one linear chromosome map; (f) identifying one or more genomic rearrangements in the linear chromosome map; and (g) correlating the one or more genomic rearrangements with a disease or a trait.

Probes

As used herein, the term "probe" refers to a molecule (e.g., an oligonucleotide, whether occurring naturally as in a purified restriction digest or produced synthetically, recombinantly or by PCR amplification), that is capable of hybridising to another molecule of interest (e.g., another oligonucleotide). When probes are oligonucleotides they may be single-stranded or double-stranded. Probes are useful in the detection, identification and isolation of particular targets (e.g., gene sequences). As described herein, it is contemplated that probes used in the present invention may be labelled with a label so that is detectable in any detection system, including, but not limited to enzyme (e.g., ELISA, as well as enzyme-based histochemical assays), fluorescent, radioactive, and luminescent systems.

With respect to arrays and microarrays, the term "probe" is used to refer to any hybridisable material that is affixed to the array for the purpose of detecting a nucleotide sequence that has hybridised to said probe. Preferably, these probes are 25-60 mers or longer.

Strategies for probe design are described in WO95/11995, EP 717,113 and WO97/29212.

Since 4C allows an unbiased genome-wide search for interactions, it is advantageous to prepare an array with probes interrogating every possible (eg. unique/non-repetitive) primary restriction enzyme recognition site in the genome. Thus, array design only depends on the choice of primary restriction enzyme and not on the actual first or secondary nucleotide sequences.

Whilst existing arrays can be used in accordance with the present invention, it is preferred to use alternative configurations.

In one configuration, one or more probes on the array are designed such that they can hybridise close to the sites that are digested by the primary restriction enzyme. More preferably, the probe(s) are within about 20 bp of the primary restriction enzyme recognition site. More preferably, the probe(s) are within about 50 bp of the primary restriction enzyme recognition site.

Suitably, the probe(s) are within about 100 bp (eg. about 0-100 bp, about 20-100 bp) of the primary restriction enzyme recognition site.

In a preferred configuration, a single, unique, probe is designed within 100 bp at each side of the sites that are digested by the primary restriction enzyme.

In another preferred configuration, the positions of sites digested by the secondary restriction enzyme relative to the positions of sites digested by the primary restriction sites are taken into account. In this configuration, a single, unique, probe is designed only at each side of the sites digested by the primary restriction enzyme that have the nearest secondary restriction enzyme recognition site at a distance large enough for a probe of a given length to be designed in between the primary and secondary restriction enzyme recognition site. In this configuration, for example, no probe is designed at the side of a particular primary restriction enzyme recognition site that has a secondary restriction enzyme recognition site within 10 bp, at that same side.

In another configuration, the probes on the array are designed such that they can hybridise at either side of the sites that are digested by the primary restriction enzyme.

Suitably, a single probe at each side of the primary restriction enzyme recognition site can be used.

In yet another configuration, two or more probes (eg. 3, 4, 5, 6, 7 or 8 or more) can be designed at each side of the primary restriction enzyme recognition site, which can then be used to investigate the same ligation event. For the number and position of probes relative to each primary restriction enzyme recognition site, the exact genomic location of its neighbouring secondary restriction enzyme recognition site can be taken into account.

In yet another configuration, two or more probes (eg. 3, 4, 5, 6, 7 or 8 or more) can be designed near each primary restriction enzyme recognition site irrespective of the nearest secondary restriction enzyme recognition site. In this configuration, all probes should still be close to the primary restriction enzyme recognition sites (preferably within 300 bp of the restriction site).

Advantageously, the latter design and also the design that uses 1 probe per (side of a) primary restriction enzyme recognition site, allows the use of different secondary restriction enzymes in combination with a given primary restriction enzyme.

Advantageously, the use of multiple (eg. 2, 3, 4, 5, 6, 7 or 8 or more) probes per primary restriction enzyme recognition site can minimise the problem of obtaining false negative results due to poor performance of individual probes. Moreover, it can also increase the reliability of data obtained with a single chip experiment and reduce the number of arrays required to draw statistically sound conclusions.

The probes for use in the array may be greater than 40 nucleotides in length and may be iso-thermal.

Preferably, probes containing repetitive DNA sequences are excluded.

Probes diagnostic for the restriction sites that directly flank or are near to the first nucleotide sequence are expected to give very strong hybridisation signals and may also be excluded from the probe design.

The array may cover any genome including mammalian (eg. human, mouse (eg. chromosome 7)), vertebrate (e.g. zebrafish)), or non-vertebrate (eg. bacterial, yeast, fungal or insect (eg. Drosophila)) genomes.

In a further preferred embodiment, the array contains 2-6 probes around every unique primary restriction site and as close as possible to the site of restriction enzyme digestion.

Preferably, the maximum distance from the site of restriction enzyme digestion is about 300 bp.

In a further preferred embodiment of the present invention, arrays for restriction enzymes—such as HindIII, EcoRI, BglII and NodI—that cover the mammalian or non-mammalian genomes are provided. Advantageously, the design of the arrays described herein circumvent the need to re-design arrays for every target sequence, provided analysis is performed in the same species.

Sets of Probes

As used herein, the term "set of probes" refers to a suite or a collection of probes that hybridise to each one of the primary restriction enzyme recognition sites for a primary restriction enzyme in a genome.

Accordingly, there is provided in a further aspect, a set of probes complementary in sequence to the nucleic acid sequence adjacent to each one of the primary restriction enzyme recognition sites for a primary restriction enzyme in genomic DNA.

Suitably, the set of probes are complementary in sequence to the first 25-60 (eg. 35-60, 45-60, or 50-60) or more nucleotides that are adjacent to each one of the primary restriction enzyme recognition sites in genomic DNA. The set of probes may be complementary in sequence to one (eg. either) side or both sides of the primary restriction enzyme recognition site. Accordingly, the probes may be complementary in sequence to the nucleic acid sequence adjacent each side of each one of the primary restriction enzyme recognition sites in the genomic DNA.

It is also possible to define a window (eg. 300 bp or less—such as 250 bp, 200 bp, 150 bp or 100 bp—from the primary restriction enzyme recognition site) in which one or more probes for the set can be designed. Such factors that are important in defining the window within which to design the probes are, for example, GC-content, absence of palindromic sequences that can form hairpin structures, maximum size to stretches of a single type of nucleotide. Accordingly, the set of probes can be complementary in sequence to the nucleic acid sequence that is less than 300 bp from each one of the primary restriction enzyme recognition sites in genomic DNA.

It is also possible to define a window of about 100 bp from the primary restriction enzyme recognition site in order to identify optimal probes near each restriction site.

In further embodiments of the present invention, the set of probes are complementary to the sequence that is less then 300 bp from each one of the primary restriction enzyme recognition sites in genomic DNA, complementary to the sequence that is between 200 and 300 bp from each one of the primary restriction enzyme recognition sites in genomic DNA and/or complementary to the sequence that is between 100 and 200 bp from each one of the primary restriction enzyme recognition sites in genomic DNA.

In further embodiments of the present invention, the set of probes are complementary to the sequence that is from 0 to 300 bp from each one of the primary restriction enzyme recognition sites in genomic DNA, complementary to the sequence that is between 0 to 200 bp from each one of the primary restriction enzyme recognition sites in genomic DNA and/or complementary to the sequence that is between 0 to 100 bp from each one of the primary restriction enzyme recognition sites in genomic DNA (eg. about 10, 20, 30, 40, 50, 60, 70, 80 or 90 bp from each one of the primary restriction enzyme recognition sites in genomic DNA).

Two or more probes may even be designed that are capable of hybridising to the sequence adjacent each primary restriction enzyme recognition site in the genomic DNA.

The probes may overlap or partially overlap. If the probes overlap then the overlap is preferably, less than 10 nucleotides.

PCR fragments representing the first 1-300 nucleotides (eg. 1-20, 1-40, 1-60, 1-80, 1-100, 1-120, 1-140, 1-160, 1-180, 1-200, 1-220, 1-240, 1-260 or 1-280 nucleotides) that flank each primary restriction enzyme recognition site can also be used.

PCR fragments may also be used as probes that exactly correspond to each genomic site that is flanked by the primary restriction enzyme recognition site and the first neighboring second restriction enzyme recognition site. Accordingly, the probe sequence may correspond to all or part of the sequence between each one of the primary restriction enzyme recognition sites and each one of the first neighbouring secondary restriction enzyme recognition sites.

Typically, the probes, array of probes or set of probes will be immobilised on a support. Supports (eg. solid supports) can be made of a variety of materials—such as glass, silica, plastic, nylon or nitrocellulose. Supports are preferably rigid and have a planar surface. Supports typically have from about 1-10,000,000 discrete spatially addressable regions, or cells. Supports having about 10-1,000,000 or about 100-100,000 or about 1000-100,000 cells are common. The density of cells is typically at least about 1000, 10,000, 100,000 or 1,000,000 cells within a square centimeter. In some supports, all cells are occupied by pooled mixtures of probes or a set of probes. In other supports, some cells are occupied by pooled mixtures of probes or a set of probes, and other cells are occupied, at least to the degree of purity obtainable by synthesis methods, by a single type of oligonucleotide.

Preferably, the array described herein comprises more than one probe per primary restriction enzyme recognition site, which in the case of a 6 bp cutting restriction enzyme occurs, for example, approximately 750,000 times per human or mouse genome.

For a restriction enzyme recognising a >6 bp recognition sequence, a single array of about 2×750,000 probes can be used to cover, for example, the complete human or mouse genome, with 1 probe at each side of each restriction site.

In a preferred array design, the total number of probe molecules of a given nucleotide sequence present on the array is in large excess to homologous fragments, present in the 4C sample to be hybridized to such array. Given the nature of 4C technology, fragments representing genomic regions close to the analyzed nucleotide sequence on the linear chromatin template will be in large excess in the 4C hybridization sample (as described in FIG. 2). To obtain quantitative information about hybridization efficiencies of such abundant fragments, it may be necessary to reduce the amount of sample to be hybridized and/or increase the number of molecules of a given oligonucleotide sequence probe on the array.

Thus, for the detection of regulatory DNA elements that frequently contact, for example, a gene promoter element it may be necessary to use an array with probes that represent only the selected genomic region (eg. about 0.5-10 Mb), but with each unique probe present at multiple (eg. about 100, 200, 1000) positions on the array. Such designs may also be preferred for diagnostic purposes to detect local (eg. within about 10 Mb) genomic rearrangements—such as deletions, inversions, duplications, etc.—around a site (e.g. gene of interest).

The array may comprise about 3×750,000 probes, 4×750,000 probes, 5×750,000 probes, or preferably, 6×750,000 probes. More preferably, the array comprises 6×750,000 probes with 2, 3, 4, 5, 6, 7 or 8 or more probes at each side of each restriction site. Most preferably, the array comprises 6×750,000 probes with 3 probes at each side of each restriction site.

Arrays of probes or sets of probes may be synthesised in a step-by-step manner on a support or can be attached in presynthesized form. One method of synthesis is VLSIPS™ (as described in U.S. Pat. No. 5,143,854 and EP 476,014), which entails the use of light to direct the synthesis of oligonucleotide probes in high-density, miniaturised arrays. Algorithms for design of masks to reduce the number of synthesis cycles are described in U.S. Pat. No. 5,571,639 and U.S. Pat. No. 5,593,839. Arrays can also be synthesised in a combinatorial fashion by delivering monomers to cells of a support by mechanically constrained flowpaths, as described in EP 624,059. Arrays can also be synthesised by spotting reagents on to a support using an ink jet printer (see, for example, EP 728,520).

In the context of the present invention, the terms "substantially a set of probes" "substantially the array of probes" means that the set or the array of probes comprises at least about 50, 60, 70, 80, 90, 95, 96, 97, 98 or 99% of the full or complete set or array of probes. Preferably, the set or the array of probes is a full or complete set of probes (ie. 100%).

In a preferred embodiment, the array comprises a single unique probe per side of each primary restriction enzyme recognition site that is present in a given genome. If this number of probes exceeds the number of probes that can be contained by a single array, the array may preferably still contain a representation of the complete genome of a given species, but at lower resolution, with for example one out of every 2, 3, 4, 5, 6, 7, 8, 9, 10, $10^2$, $10^3$, $10^4$ etc. probes as ordered on the linear chromosome template present on the array. Such arrays that cover the complete human, or other, genome at sub-optimal resolution may be preferred over high-resolution arrays that cover part of the same genome, for example in cases where translocation partners are to be found.

Preferably, the representation of the complete genome of a given species at lower resolution is obtained by probes on the array that each represent a single restriction fragment as obtained after digestion with a primary restriction enzyme. Preferably, this is obtained by ignoring every second, third, fourth, fifth, sixth, seventh, eighth, ninth, tenth, twentieth, thirtieth, fortieth, fiftieth, sixtieth, seventieth, eightieth, ninetieth, or one hundredth eg. second to one hundredth) etc. probe that hybridises to the same restriction fragment.

Preferably, the representation of the complete genome of a given species at lower resolution comprises probes that are distributed equally along the linear chromosome templates. Preferably, this is obtained by ignoring one or more probes in those genomic regions that show highest probe density.

Hybridisation

The term "hybridisation" as used herein shall include "the process by which a strand of nucleic acid joins with a complementary strand through base pairing" as well as the process of amplification as carried out in, for example, polymerase chain reaction (PCR) technologies.

Nucleotide sequences capable of selective hybridisation will be generally be at least 75%, preferably at least 85 or 90% and more preferably at least 95% or 98% homologous to the corresponding complementary nucleotide sequence over a region of at least 20, preferably at least 25 or 30, for instance at least 40, 60 or 100 or more contiguous nucleotides.

"Specific hybridisation" refers to the binding, duplexing, or hybridising of a molecule only to a particular nucleotide sequence under stringent conditions (e.g. 65° C. and 0.1×SSC {1×SSC=0.15 M NaCl, 0.015 M Na-citrate pH 7.0}). Stringent conditions are conditions under which a probe will hybridise to its target sequence, but to no other sequences. Stringent conditions are sequence-dependent and are different in different circumstances. Longer sequences hybridise specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to a target sequence hybridise to the target sequence at equilibrium. (As the target sequences are generally present in excess, at Tm, 50% of the probes are occupied at equilibrium). Typically, stringent conditions include a salt concentration of at least about 0.01 to 1.0 M Na ion concentration (or other salts) at pH 7.0 to 8.3 and the temperature is at least about 30° C. for short probes. Stringent conditions can also be achieved with the addition of destabilising agents—such as formamide or tetraalkyl ammonium salts.

As will be understood by those of skill in the art, a maximum stringency hybridization can be used to identify or detect identical nucleotide sequences while an intermediate (or low) stringency hybridization can be used to identify or detect similar or related polynucleotide sequences.

Methods are also described for the hybridisation of arrays of probes to labelled or unlabeled nucleotide sequences. The particular hybridisation reaction conditions can be controlled to alter hybridisation (e.g., increase or decrease probe/target binding stringency). For example, reaction temperature, concentrations of anions and cations, addition of detergents, and the like, can all alter the hybridisation characteristics of array probes and target molecules.

Frequency of Interaction

Quantifying ligation frequencies of restriction fragments gives a measure of their cross-linking frequencies. Suitably, this can be achieved using PCR as used in conventional 3C technology as described by Splinter et al. (2004) (supra). Briefly, the formation of PCR products can be measured by scanning the signal intensities after separation on ethidium bromide stained agarose gels, using a Typhoon 9200 imager (Molecular Dynamics, Sunnyvale, Calif.). Suitably, several controls are used for the correct interpretation of data as also described in Splinter et al. (2004) (supra).

Since the 4C technology described herein provides for the high-throughput analysis of the frequency of interaction of two or more nucleotide sequences in the nuclear space, it is preferred that the ligation frequencies of restriction fragments are quantified using the arrays described herein.

For quantitation, signals obtained for a 4C sample can be normalised to signals obtained for a control sample. 4C sample and control sample(s) will be labelled with different and discernable labels (eg. dyes) and will be simultaneously hybridised to the array. Control sample(s) will typically contain all DNA fragments (i.e. all potential second nucleotide sequences that have ligated to the first (target) nucleotide sequence) in equimolar amounts and, to exclude a bias in hybridisation efficiency, they should be similar in size to the second nucleotide sequence(s). Thus, control template will typically contain genomic DNA (of the same genetic background as that used to obtain the 4C template), digested with both the primary and the secondary restriction enzyme and labelled by the same method (e.g. random priming) as the 4C template. Such control template makes it possible to correct for probe-to-probe differences in hybridisation efficiency. Normalising 4C array signals to control array signals makes it possible to express results in terms of enrichment over random events.

Labeled 4C template may even be hybridized to an array with or without a differentially labeled control sample and with or without one or more differentially labeled other 4C templates. Other 4C templates can be unrelated to this 4C template, for example it may be obtained from different tissue and/or obtained with a different set of inverse PCR primers. For example, the first 4C template may be patient material and the second 4C template may be obtained from a healthy subject or a control sample.

Given the striking hybridisation patterns that are to be expected for genetic rearrangements it will not always be necessary to compare diseased subjects with healthy subjects. Accordingly, multiple (eg. two or more) 4C templates, each interrogating a different locus from the same patient or subject may be hybridized to one (eg. one or more) array.

The 4C templates may be differentially labeled (eg. with two or multi-color hybridization) and/or may be identically labeled in case such loci normally reside on different chromosomes or on the same chromosome at a distance far enough for minimal overlap between DNA-DNA interaction signals. As an example, material from a subject with T-cell leukemia may be processed to obtain 4C templates for TCRα/δ (labeled in one color, in order to detect translocations), and MLL, TAL1, HOX11 and LMO2 (each labeled in the same second color, in order to detect other genetic rearrangements). These five 4C templates may be hybridized to one array, which will allow the simultaneous analysis at multiple loci for a genomic rearrangement associated with the disease.

For quantification of interaction frequencies, absolute signal intensities or ratios over control sample may also be considered. In addition, signals of probes adjacent on the linear chromosome template may be used to identify interacting chromosomal regions. Such positional information is preferably analyzed by ordering the probes on the linear chromosome template and analysing the absolute signal intensities, or ratios over control template signals, by sliding window approaches, using for example running mean or running median approaches.

The frequency of interaction of one or more target nucleotide sequence with one or more nucleotide sequences of interest (eg. one or more genomic loci) obtained according to the methods described herein may be used to reconstruct parts of, or entire, linear chromosome maps and identify balanced and unbalanced genomic rearrangements that occurred within and between chromosomes, wherein such rearrangements are indicative of a trait or disease.

Assay Method

In a further aspect of the present invention, there is a provided an assay method for identifying one or more agents that modulate a DNA-DNA interaction.

As used herein, the term "modulate" refers to preventing, decreasing, suppressing, restorating, elevating, increasing or otherwise affecting the DNA-DNA interaction.

In some cases, it may be desirable to evaluate two or more agents together for use in modulating the DNA-DNA interaction. In these cases, assays may be readily modified by adding such additional agent(s) either simultaneously with, or subsequently to, the first agent.

The method of the present invention may also be a screen, whereby a number of agents are tested for modulating the activity of the DNA-DNA interaction.

It is expected that the assay methods of the present invention will be suitable for both small and large-scale screening of agents as well as in quantitative assays.

Medical uses of such therapeutic agents are within the scope of the present invention as are the drug development programs themselves and pharmaceutical compositions comprising such agents. A drug development program may, for example, involve taking an agent identified or identifiable by the methods described herein, optionally modifying it (e.g. modifying its structure and/or providing a novel composition comprising said moiety) and performing further studies (e.g. toxicity studies and/or studies on activity, structure or function). Trials may be performed on non-human animals and may eventually be performed on humans. Such trials will generally include determining the effect(s) of different dosage levels. Drug development programs may utilise computers to analyse moieties identified by screening (e.g. to predict structure and/or function, to identify possible agonists or antagonists, to search for other moieties that may have similar structures or functions, etc.).

Diagnostic Testing

Currently, various genomic rearrangements remain difficult to detect by available molecular-cytogenetic techniques. Although the array comparative genomic hybridization technique (array-CGH) is a newly developed technique for the detection of chromosomal amplification and/or deletions with a resolution of 35-300 Kb, this technique is not suitable to detect balanced translocations and chromosomal inversions. On the other hand, spectral karyotyping (SKY) or conventional karyotyping is often performed on patient material for the detection of chromosomal translocations as well as numerical changes, but the resolution to define translocation breakpoints is low, usually 10-50 Mb and 5-10 Mb, respectively. Consequently, results obtained by both methods and especially SKY will lead to time-consuming and labor-intensive validations experiments like fluorescence in situ hybridization (FISH) and molecular breakpoint cloning strategies.

4C technology involves a procedure that can detect any chromosomal rearrangements on the basis of changed interaction frequencies between physically linked DNA sequences. 4C technology is therefore useful for the identification of (recurrent) chromosomal rearrangements for most human malignancies/multiple congenital malformations or mental retardation. An important advantage of 4C technology is that it allows for the very accurate mapping of the breakpoint to a region of only several thousands of basepairs.

Another advantage of 4C technology is that no prior knowledge is required on the exact position of the breakpoint, since breakpoints will be detectable even when the 4C-bait sequence is located 1-5 Mb away from the breakpoint. This has also the advantage that the same bait sequence can be used for the detection of specific chromosomal rearrangements covering large breakpoint areas. The accurate mapping of genomic rearrangements by 4C technology will greatly facilitate the identification of aberrantly expressed gene(s) underlying diseases or genetic disorders, which will importantly contribute to a better understanding of the genotype-phenotype correlations, assist in treatment decision-making and add important prognostic information.

In one embodiment of the present invention, in order to provide a basis for the diagnosis or prognosis of disease, normal or standard values from a subject are established. This may be accomplished by testing samples taken from normal subjects—such as animals or humans. The frequency of the DNA-DNA interaction may be quantified by comparing it to a dilution series of positive controls. Then, standard values obtained from normal samples may be compared with values obtained from samples from subjects affected or potentially affected by a disease or a disorder. Deviation between standard and subject values establishes the presence of the disease state.

Such diagnostic assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for the DNA-DNA interaction may be established. Standard values obtained from normal samples may be compared with values obtained from samples from subjects potentially affected by a disorder or disease. Deviation between standard and subject values establishes the presence of the disease state. If disease is established, an existing therapeutic agent may be administered, and treatment profile or values may be generated. Finally, the method may be repeated on a regular basis to evaluate whether the values progress toward or return to the normal or standard pattern. Successive treatment profiles may be used to show the efficacy of treatment over a period of several days or several months.

Figure 2:
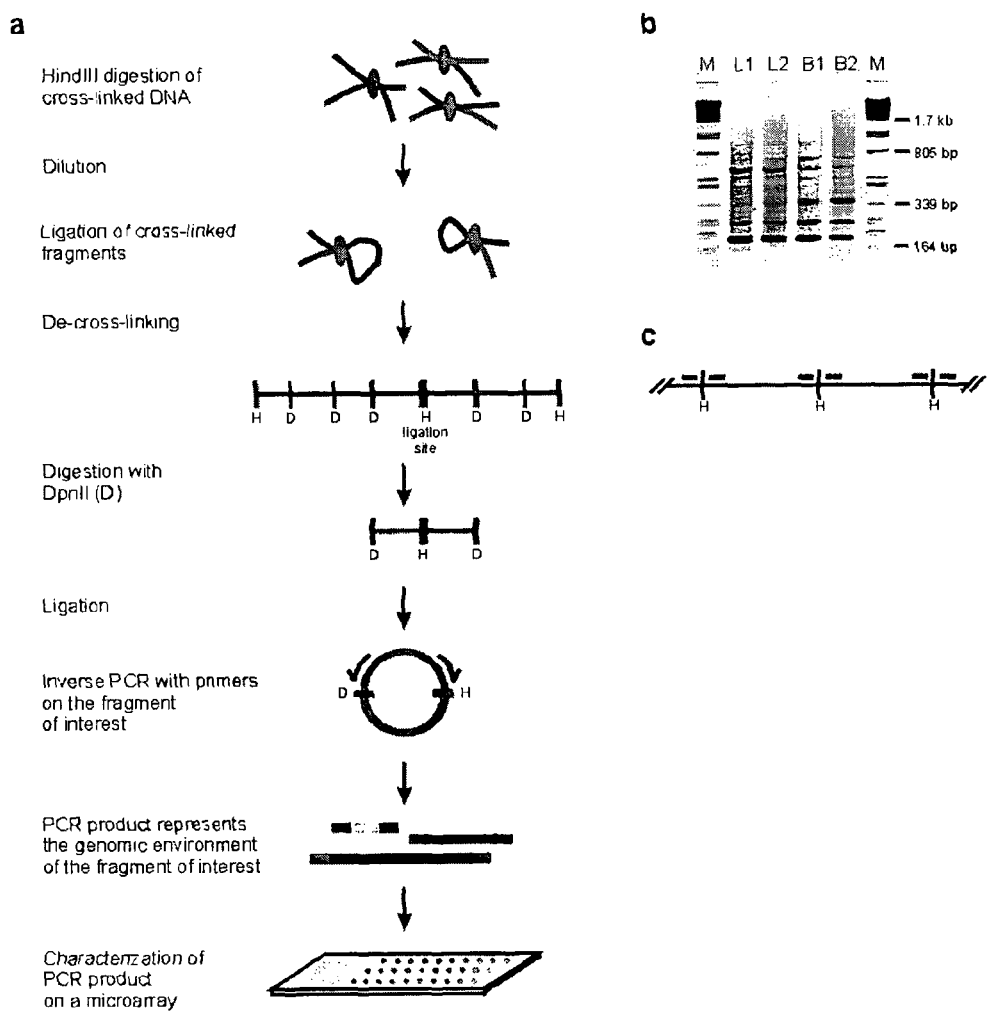
Figure 3:
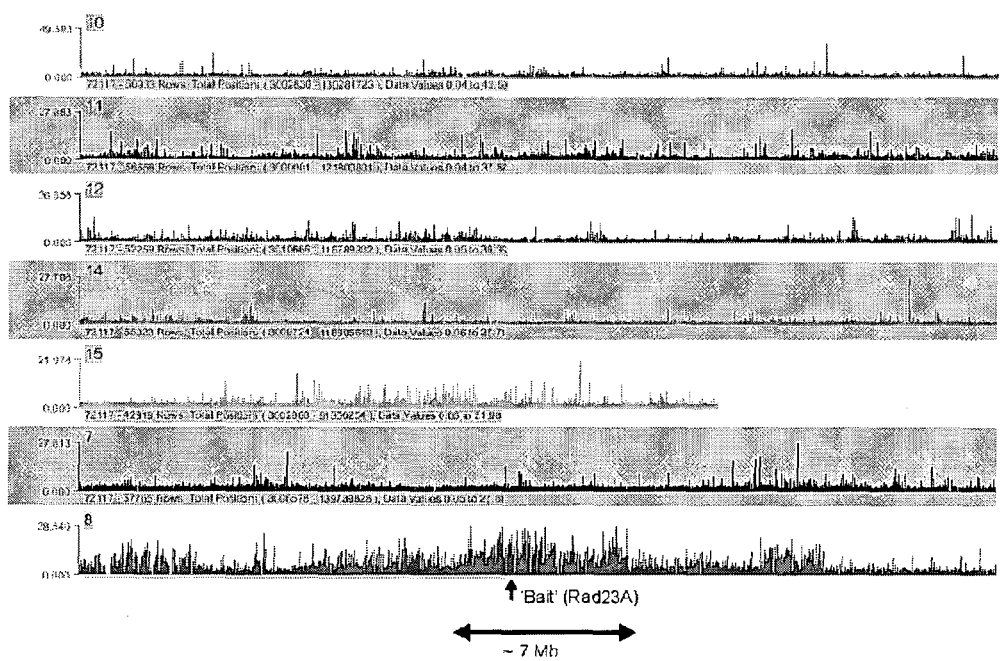
Figure 5:
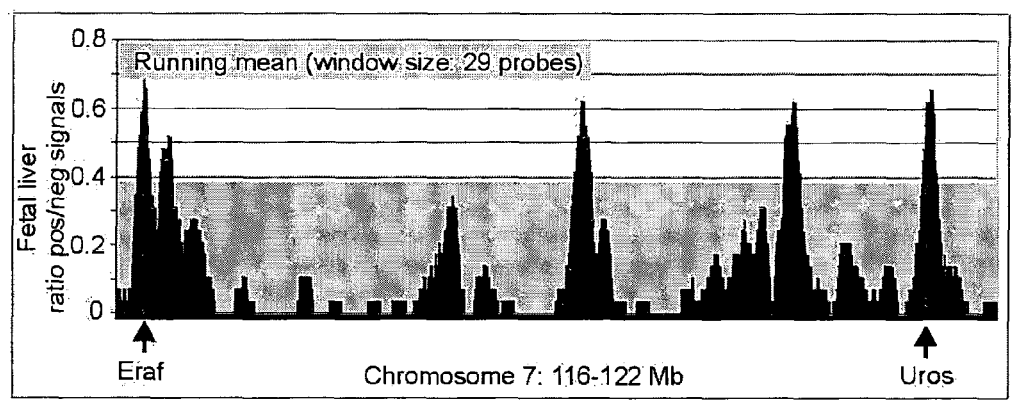
Figure 6:
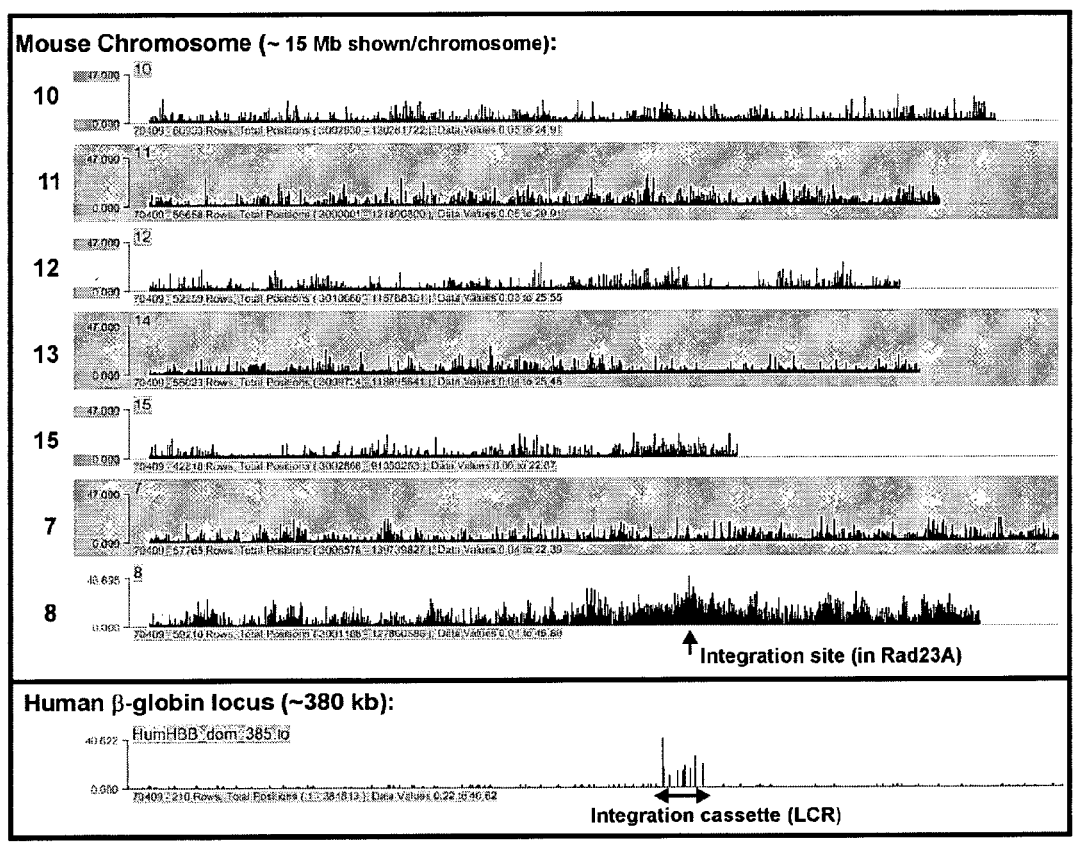
Figure 7:
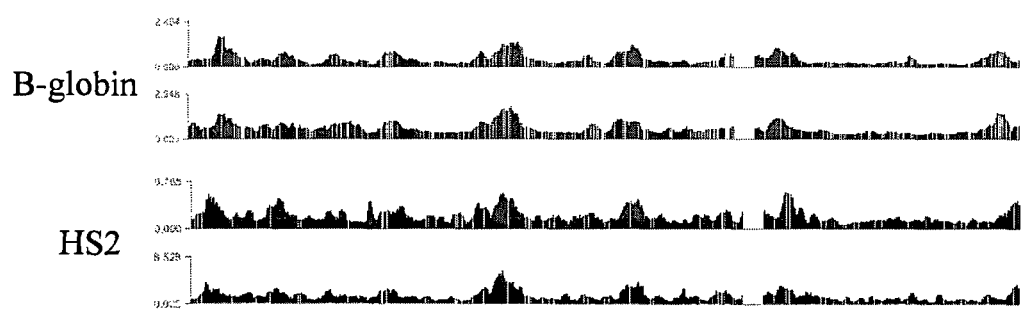

4C technology accurately detects at least 5 Mb of genomic DNA linked in cis to the nucleotide sequence that is analysed (see FIGS. 2-3 and 5). Advantageously, 4C technology may be used to detect any genomic aberration that is accompanied by a change in genomic site separation between rearranged sequences and a 4C sequence (bait) of choice. Such change may be, for example, an increase or decrease in genomic site separation or may be an under-representation (as in deletions) or over-representation (as in duplications) of sequences proximal (eg. up to or greater than 15 Mb) to the 4C sequence (bait). Typically, such genomic aberrations or rearrangements are a cause of or are associated with diseases—such as cancer (eg. leukaemia) and other genetic or congenital diseases as described herein.

Genetic aberrations (eg. genomic or chromosomal aberrations—such as balanced and/or or unbalanced genomic or chromosomal aberrations) include, but are not limited to rearrangements, translocations, inversions, insertions, deletions and other mutations of nucleic acid (eg. chromosomes) and also losses or gains of part or whole chromosomes. They are a leading cause of genetic disorders or diseases, including congenital disorders and acquired diseases—such as malignancies. In many rearrangements, two different chromosomes are involved. In this way, genes (or fragments of genes) are removed from the normal physiological context of a particular chromosome and are located to a recipient chromosome, adjacent to non-related genes or fragments of genes (often oncogenes or proto-oncogenes).

Malignancies can include acute leukemias, malignant lymphomas and solid tumours. Non-limiting examples of alterations are t(14;18) which occurs frequently in NHL; t(12;21) which is frequently found in childhood precursor-B-ALL; and the presence of 11q23 (MLL (myeloid-lymphoid leukaemia or mixed-lineage leukaemia) gene) aberrations in acute leukemias.

The MLL gene in chromosome region 11q23 is involved in several translocations in both ALL and acute myeloid leukemias (AML). To date, at least ten partner genes have been identified. Some of these translocations,—such as t(4;11) (q21;q23), t(11;19) (q23;p13) and t(1;11) (p32;q23), predominantly occur in ALL, where as others, like t(1;11) (q21; q23), t(2;11) (p21;q23), t(6;11) (q27;q23) and t(9;11) (p22; q23) are more often observed in AML. Rearrangements involving the 11q23 region occur very frequently in infant acute leukemias (around 60-70%), and to a much lesser extent in childhood and adult leukemias (each around 5%).

Rearrangements in lymphoid malignancies often involve Ig or TCR genes. Examples include the three types of translocations (t(8;14), t(2;8), and t(8;22)) that are found in Burkitt's lymphomas, in which the MYC gene is coupled to Ig heavy chain (IGH), Ig kappa (IGK), or Ig lambda (IGL) gene segments, respectively. Another common type of translocation in this category is t(14;18) (q32;q21) which is observed in about 90% of follicular lymphomas, one of the major NHL types. In this translocation the BCL2 gene is rearranged to regions within the IGH locus within or adjacent to the JH gene segments. The result of this chromosome aberration is the overexpression of the BCL2 protein, which plays a role as a survival factor in growth control by inhibiting programmed cell death.

The BCL2 gene consists of three exons, but these are scattered over a large area. Of these the last exon encodes a large 3' untranslated region (3' UTR). This 3' UTR is one of the two regions in which many t(14;18) breakpoints are clustered and is called the "major breakpoint region"; the other breakpoint region involved in t(14;18) translocations, is located 20-30 kb downstream of the BCL2 locus and is called the "minor cluster region". A third BCL2 breakpoint area, the VCR (variant cluster region), is located at the 5' side of the BCL2 locus and is amongst others involved in variant translocations, i.e., t(2;18) and t(18;22), in which IGK and IGL gene segments are the partner genes.

Thus, by way of example, 4C technology can be applied to the screening of patient material for genetic aberrations near or in loci that were chosen based on their frequent association with a given clinical phenotype. Further non-limiting examples of such loci are AML1, MLL, MYC, BCL, BCR, ABL1, immunoglobulin loci, LYL1, TAL1, TAL2, LMO2, TCRα/δ, TCRβ, HOX and other loci in various lymphoblastic leukemias.

Advantageously, if a genetic aberration is suspected, 4C technology can be applied as the first and only screen to verify and map the presence of the aberration as explained herein.

Detection of Genomic Rearrangements

In a particularly preferred embodiment of the present invention, the methods described herein can be used for the detection of genomic rearrangements.

Currently, genomic rearrangements—such as translocation breakpoints—are very difficult to detect. For example, comparative genomic hybridization (CGH) micro-arrays can detect several types of rearrangements but fail to detect translocations. If translocation is suspected in a patient but chromosome partners are unknown, spectral karyotyping (SKY) may be performed to find translocation partners and obtain an approximate estimate of breakpoint locations. However, the resolution is very poor (usually not better than ~50 Mb) and additional fine-mapping (which is both time consuming and expensive) is usually required. This is normally done using Fluorescence In Situ Hybridization (FISH), which again provides limited resolution. Using FISH, breakpoints can be located to ±50 kb region at maximum resolution.

DNA-DNA interaction frequencies primarily are a function of the genomic site separation, i.e. DNA-DNA interaction frequencies are inversely proportional to the linear distance (in kilobases) between two DNA loci present on the same physical DNA template (Dekker et al., 2002). Thus, a translocation, which creates one or more new physical DNA templates, is accompanied by altered DNA-DNA interactions near the breakpoints, and this can be measured by 4C technology. Diseases based on translocations are typically caused by aberrant DNA-DNA interactions, as translocation is the result of the physical linkage (interaction) of broken chromosome (DNA) arms.

Accordingly, for the detection of translocations, 4C technology may be used to identify those DNA-DNA interactions that are different between diseased and non-diseased subjects.

By way of example, 4C technology can be applied to the screening of patient material for translocations near loci that were chosen based on their frequent association with a given clinical phenotype as described herein.

If translocation is suspected in a patient but chromosome partners are unknown, an initial mapping may be performed using currently available methods like spectral karyotyping (SKY). This may identify the translocation partners and provide a very rough estimate of breakpoint locations (usually not better than ~50 Mb resolution). 4C technology can then be applied, using 'bait'-sequences in this region located for example at every 2 Mb, 5 Mb, 10 Mb, 20 Mb (or other intervals as described herein) to fine map the breakpoint and identify for example the gene(s) that are mis-expressed as a consequence of the translocation.

Typically a translocation will be identified by way of an abrupt transition from low to high interaction frequencies on a chromosome other than the one containing the 4C-bait sequence, or elsewhere on that same chromosome.

In a preferred embodiment, the sample from the subject is in a pre-malignant state.

In a preferred embodiment, the sample from the subject consists of cultured or uncultured amniocytes obtained by amniocentesis for prenatal diagnosis.

In a preferred array design, probes present on a single array represent the complete genome of a given species at maximum resolution. Thus, arrays to detect translocations and the like by 4C technology contain probes as described herein complementary to every side of every primary restriction enzyme recognition site in the genome of a given species (e.g. human).

In another preferred design, probes present on a single array represent the complete genome of a given species, but not at maximum resolution. Thus, arrays to detect translocations and the like by 4C technology contain probes as described herein that are complementary to only one side of every primary restriction enzyme recognition site in the genome of a given species (e.g. human).

In another preferred design, probes present on a single array represent the complete genome of a given species, but not at maximum resolution. Thus, arrays to detect translocations, deletions, inversions, duplications and other genomic rearrangements by 4C technology contain probes as described herein that are complementary to one side of every other primary restriction enzyme recognition site as ordered along the linear template of the genome of a given species (e.g. human).

Thus, arrays to detect translocations, deletions, inversions, duplications and other genomic rearrangements by 4C technology contain probes as described herein that each represent a single restriction fragment as obtained after digestion with a primary restriction enzyme. Preferably, this is obtained by ignoring every second, third, fourth, fifth, sixth, seventh, eight, ninth, tenth, twentieth, thirtieth, fortieth, fiftieth, sixtieth, seventieth, eightieth, ninetieth, or one hundredth etc probe that hybridizes to the same restriction fragment. Arrays to detect translocations, deletions, inversions, duplications and other genomic rearrangements by 4C technology may contain probes as described herein that are distributed equally along the linear chromosome templates. Preferably, this is obtained by ignoring one or more probes in those genomic regions that show highest probe density.

In another preferred design, probes present on a single array represent the complete genome of a given species, but not at maximum resolution. Thus, arrays to detect translocations, deletions, inversions, duplications and other genomic rearrangements by 4C technology contain probes as described herein complementary to one side of every third, fourth, fifth, sixth, seventh, eight, ninth, tenth, twentieth, thirtieth, fortieth, fiftieth, sixtieth, seventieth, eightieth, ninetieth, or one hundredth etc primary restriction enzyme recognition site as ordered along the linear template of the genome of a given species (e.g. human). Arrays to detect translocations, deletions, inversions, duplications and other genomic rearrangements by 4C technology may contain probes as described herein, which represent the complete genome, but with a single probe every 100 kilobases. Arrays to detect translocations, deletions, inversions, duplications and other genomic rearrangements by 4C technology may contain probes as described herein which represent every single primary restriction enzyme recognition site in the genome that can be represented by a unique probe sequence.

In another preferred array design, probes as described herein on a single array represent genomic regions of a given size—such as about 50 kb, 100 kb, 200 kb, 300 kb, 400 kb, 500 kb, 1 Mb, 2 Mb, 3 Mb, 4 Mb, 5 Mb, 6 Mb, 7 Mb, 8 Mb, 9 Mb or 10 Mb—(eg. from about 50 kb-10 Mb) around all loci known to be involved in translocations, deletions, inversions, duplications and other genomic rearrangements.

In another preferred array design, probes as described herein on a single array represent genomic regions of a given size—such as about 50 kb, 100 kb, 200 kb, 300 kb, 400 kb, 500 kb, 1 Mb, 2 Mb, 3 Mb, 4 Mb, 5 Mb, 6 Mb, 7 Mb, 8 Mb, 9 Mb or 10 Mb—(eg. from about 50 kb-10 Mb) around a selection of loci known to be involved in translocations, deletions, inversions, duplications and other genomic rearrangements. Selections can be made on educated criteria, for example they can represent only the loci that are implicated in a given type of disease.

In another preferred array design, probes as described herein on a single array represent a genomic region of interest of, for example, 100 kb, 200 kb, 300 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, 10 Mb, 20 Mb, 30 Mb, 40 Mb, 50 Mb, 60 Mb, 70 Mb, 80 Mb, 90 Mb, or 100 Mb (eg. 100 kb-10 Mb) (part of) a chromosome or multiple chromosomes, with each probe being represented multiple (eg. 10, 100, 1000) times to allow quantitative measurements of hybridisation signal intensities at each probe sequence.

In a preferred experimental design, the 4C sequence (bait) is within about 0 kb, 10 kb, 20 kb, 30 kb, 40 kb, 50 kb, 100 kb, 200 kb, 300 kb, 400 kb, 500 kb, 1 Mb, 2 Mb, 3 Mb, 4 Mb, 5 Mb, 6 Mb, 7 Mb, 8 Mb, 9 Mb 10 Mb, 11 Mb, 12 Mb, 13 Mb, 14 Mb or 15 Mb (eg. from about 0-15 Mb) or more from the actual rearranged sequence (i.e. breakpoint in case of a translocation).

In a preferred hybridization, two differentially labeled 4C templates obtained with one sequence (4C bait) from a diseased and non-diseased subject are hybridized simultaneously to the same array. Differences in DNA-DNA interactions allow the detection of the breakpoint in cis (on the same chromosome as the 4C-bait) and in trans (on the translocation partner).

In a preferred hybridization, multiple differentially labeled 4C templates obtained with one sequence (4C bait) from diseased and non-diseased subjects are hybridized simultaneously to the same array. Differences in DNA-DNA interactions allow the detection of the breakpoint in cis (on the same chromosome as the 4C-bait) and in trans (on the translocation partner).

Advantageously, multi-color, instead of dual color analysis on micro-arrays may be utilised allowing the simultaneous hybridization of more than two samples to a single array. Accordingly, multi-color hybridization can be used in 4C technology.

In a preferred hybridisation, multiple differentially labeled 4C templates obtained with one sequence (4C bait) from diseased subjects and one differentially labeled 4C template from a non-diseased, subject are hybridised simultaneously to the same array. Differences in DNA-DNA interactions allow the detection of the breakpoint in cis (on the same chromosome as the 4C-bait) and in trans (on the translocation partner).

In another preferred hybridisation, two differentially labeled 4C templates from the same non-diseased subject, obtained with two different sequences (4C-baits) that each represent another possible translocation partner, are hybridised simultaneously to the same array. Clusters of strong hybridisation signals observed on the linear template of chromosomes unrelated to the chromosome carrying the sequence of interest (4C-bait) will identify the translocation partner chromosome and the breakpoint on the translocation partner.

In another preferred hybridisation, multiple differentially labeled 4C templates from the same non-diseased subject, obtained with multiple different sequences (4C-baits) that each represent another possible translocation partner, are hybridised simultaneously to the same array. Clusters of strong hybridisation signals observed on the linear template of chromosomes unrelated to the chromosome carrying the sequence of interest (4C-bait) will identify the translocation partner chromosome and its breakpoint for the sequence of interest.

Material used for the detection of translocations, deletions, inversions, duplications and other genomic rearrangements by 4C technology can be obtained by cross-linking (and further processing, as described) of living cells and/or dead cells and/or nuclear lysates and/or isolated chromatin etc. (as described herein) from diseased and/or non-diseased subjects.

Detection of Inversions

Inversions (eg. balanced inversions) cannot be detected by methods—such as Comparative Genomic Hybridization techniques—but can be detected by 4C technology particularly when the (balanced) inversion is close (eg. up to about 1-15 Mb or more) to the 4C sequence (bait).

Detection of (balanced) inversions is based on identifying those DNA-DNA interactions that were different between diseased and non-diseased subjects. Inversions will change the relative position (in kilobases) on the physical DNA template of all (but the most centrally located) sequences of the rearranged region as measured against a sequence nearby on the same chromosome that is taken as 4C sequence (bait). Since DNA-DNA interaction frequencies are inversely related to genomic site separation, diseased subjects will give inversed patterns of hybridization intensities for all probes located in the rearranged genomic region, as compared to a non-diseased subject. Thus, 4C technology allows the identification of position and size of (balanced) inversions.

According to this aspect of the present invention, a preferred dedicated array design comprises probes on a single array representing genomic regions of a given size—such as about 50 kb, 100 kb, 200 kb, 300 kb, 400 kb, 500 kb, 1 Mb, 2 Mb, 3 Mb, 4 Mb, 5 MB, 6 Mb, 6 Mb, 7 Mb, 8 Mb, 9 Mb or 10 Mb) (eg. 50 kb-10 Mb) around the locus at which the inversion or other rearrangement is suspected.

In another preferred dedicated array design, probes on a single array represent genomic regions of a given size (50 kb, 100 kb, 200 kb, 300 kb, 400 kb, 500 kb, 1 Mb, 2 Mb etc) around the locus at which the inversion or other rearrangement is suspected. For reliable quantitative analysis of signal intensities the amount of probe present on the array is typically in large excess to the amount of cognate fragments that are hybridized to the array. Therefore, it may be necessary to have each probe present multiple times (eg 10, 20, 50, 100, 1000 times etc) on the array. In addition, it may be necessary to titrate the amount of template that is to be hybridized to the array.

Detection of Deletions

Detection of deletions is based on identifying those DNA-DNA interactions that were different between diseased and non-diseased subjects. Deletions will result in the absence of DNA interactions with a 4C sequence (bait) located near (eg. about 1, 2, 3, 4, 5, 6, 7, 8, 9, 10, 11, 12, 13, 14 or 15 Mb or more) the deleted region. This may result in the complete absence of hybridization signals for all probes located in the rearranged region if the deletion is present on both alleles (homozygous), or a reduction for diseased versus non-diseased subjects of signal intensities if the deletion is present on only one allele (heterozygous). Deletion brings more distal sequences into closer proximity on the physical DNA template to the 4C sequence analyzed (bait), which will result in stronger hybridization signals for probes located directly beyond the deleted region.

Detection of Duplication(s)

Detection of duplication is typically based on identifying those DNA-DNA interactions that are different between diseased and non-diseased subjects. Probes in the duplicated region will show increased hybridization signals with a 4C sequence (bait) located near (eg. about 1, 2, 3, 4, 5, 6, 7, 8, 9, 10, 11, 12, 13, 14 or 15 Mb or more) the rearranged region, as compared to signals from a control non-diseased subject. Probes beyond the duplicated region are further apart from the 4C sequence and consequently will show decreased hybridization signals as compared to signals from a control non-diseased subject.

Preferably, an increase or a decrease DNA-DNA interaction frequency for the subject sample as compared to the control is indicative of a duplication or insertion.

Preferably, an increase in DNA-DNA interaction frequency for the subject sample as compared to the control and/or a reduction in DNA-DNA interaction frequency for more distant regions is indicative of a duplication or insertion.

Prenatal Diagnosis

Advantageously, 4C technology can also be used in prenatal diagnosis.

Nucleic acid can be obtained from a fetus using various methods that are known in the art. By way of example, amniocentesis can be used to obtain amniotic fluid from which fetal cells in suspension are extracted and cultured for several days (Mercier & Bresson (1995) *Ann. Gnt.*, 38, 151-157). Nucleic acid from the cells can be then extracted. The collection of chorial villi may make it possible to dispense with the culturing step and avoids the collection of amniotic fluid. These techniques may be applied earlier (up to 7 weeks of gestation for the collection of chorial villi and 13-14 weeks for amniocentesis), but with a slightly increased risk of abortion.

A direct collection of fetal blood at the level of the umbilical cord can also be used to obtain nucleic acid, but typically requires a team of clinicians specialised in this technique (Donner et al. (1996) *Fetal Diagn. Ther.*, 10, 192-199).

Advantageously, genetic aberrations (eg. genomic or chromosomal aberrations)—such as rearrangements, translocations, inversions, insertions, deletions and other mutations in chromosomes and nucleic acid—may be detected at this stage.

Preferably, genetic aberrations (eg. genomic or chromosomal aberrations)—such as rearrangements, translocations, inversions, insertions, deletions and other mutations in chromosomes 21, 18, 13, X or Y and also losses or gains of part or whole chromosomes 21, 18, 13, X or Y may be detected since these are the chromosomes in which the majority of aberrations occur in the foetus.

Determination of Genomic Integration Sites 4C technology also allows the determination of genomic integration sites of viruses and transgenes, etc, also when multiple copies are inserted at different positions in the genome (as described in FIG. 3).

Determining Predisposition to Acquiring Certain Translocations

Advantageously, 4C technology can also be applied to non-diseased subjects to measure the genomic environment of loci frequently involved in genetic aberrations. In this way, it is possible to determine the predisposition of the subject to acquire certain genetic aberrations.

Thus, in addition to the medical uses described herein, the present invention can be used in diagnosis.

Multiplex 4C

The present invention allows the simultaneous analysis of the frequency of interactions of multiple target nucleotide sequences with one or more nucleotide sequences of interest. Amplification may be achieved using multiplex PCR. Such methods allow for an unbiased screen for balanced and unbalanced genomic rearrangements i.e. translocations, inversions, deletions and duplications that may have occurred anywhere in the genome. The methods can be used to identify breakpoints of rearrangements at very high resolution, typically within twenty kilobases (on average 5 kb). The method can be used in diagnostic applications as set forth above, for example prenatal diagnosis, postnatal diagnosis and for the analysis of tumor and other diseased samples to identify genomic rearrangements underlying diseases or predisposing subjects to disease. Amplified nucleotide sequences of interest can be analyzed on tailored 4C microarrays (as described above), or on genomic tiling micro-arrays, or by sequencing as described further herein.

The Simultaneous Screening of Rearrangements at Multiple Loci Known to be Associated with a Disease.

For many diseases, syndromes or phenotypes, multiple possible causative DNA alterations are known and subjects need to be screened to identify the exact rearrangement underlying the disease/syndrome/phenotype. For example, in the case of lymphoblastic leukemias rearrangements involving AML1, MLL, MYC, BCL, BCR, ABL, immunoglobulin loci, LYL1, TAL1, TAL2, TCRα/δ, TCRβ, HOX and possibly other loci frequently underlie the disease; 4C technology can be applied to identify which locus and rearrangement is involved in a patient with the given disease.

In this embodiment, 4C technology is directed to each of the loci of interest. Each locus can be analysed separately, but multiple loci can also be analysed simultaneously on a single array. Thus, a 4C screen can involve the (inverse) PCR amplification of DNA elements interacting with one or more target nucleotide sequences near each of the loci that needs to be analysed for rearrangements. Target sequences at or near these loci are chosen based on the criteria mentioned herein.

Amplification of nucleotide sequences of interest can be performed separately for each target nucleotide sequence, or can be performed simultaneously in one reaction volume by multiplex (inverse) PCR. The latter is to be preferred in cases when nucleotide sequences of interest interacting with different target nucleotide sequences can be identically labelled without compromising the analysis. This may be the case for example when loci are located on different chromosomes or when loci are located on the same chromosome at a distance far enough for minimal overlap between DNA-DNA interaction signals, or in cases when overlap between DNA-DNA interactions amplified from different target nucleotide sequences does not interfere with the detection of genomic rearrangements.

Amplification of nucleotide sequences of interest interacting with different target nucleotide sequences is preferably performed separately when each set of DNA-DNA interactions needs to be labelled differently or when inverse PCR primer sets interfere with each other's amplification efficiency.

Differentially or identically labelled sequences of interest interacting with the various target nucleotide sequences are hybridised to a single or multiple micro-arrays containing probes representing the complete genome (e.g high density arrays or tiling arrays) or a selected part of the genome, as described above. Hybridisation signals will be compared to those obtained with a control sample, where an increase or decrease in DNA-DNA interaction frequencies measured in the test versus control sample is indicative for a DNA rearrangement in the test sample.

An Unbiased Genome Wide Screening for Rearrangements at Unknown Positions in the Genome.

In a second embodiment, 4C technology is applied for an unbiased genome-wide screen to identify rearrangements in a sample from a diseased (or non-diseased) subject, where the rearrangements are previously unknown and/or occur at unknown locations. In this embodiment, the target sequences cannot be chosen to be close to the rearrangement. The target sequences are thus not known or suspected to be associated with the disease. Instead, they are chosen to be distributed throughout the chosen genome or section of genome, so as to provide sufficient coverage of the chromatin to be investigated. Preferably, the entire genome is covered.

For instance, target sequences are chosen such that their interacting sequences of interest, being mostly the sequences directly surrounding the target sequence, i.e within 5, 10, 15, 20, 25, 30, 35, 40, or 45 to 50 Mb from the target sequence) cover the complete or a substantial part of the genome or a chromosome or a part of a chromosome. This will allow reconstructing physical chromosome maps present in any subject or cell type.

For two target sequences adjacent on the linear chromosome template to have overlapping interacting DNA sequences (i.e overlapping genomic environments) they need to be, for example, 5, 10, 15, 20, 25, 30, 35, 40, 45, or 50 to 100 Mb away from each other. Thus, to cover the complete genome (2-3×10⁹ bp) with target sequences separated ~10 Mb, 200-300 target sequences are required. To cover the complete genome with target sequences separated ~50 Mb, 40-60 target sequences are required. In an ultimate embodiment, only one target sequence per chromosome is required to cover the complete genome.

All nucleotide sequences of interest that interact with the target sequences are amplified as in 4C, either together in a single reaction mix (or a limited number of reaction mixes) by multiplex (inverse) PCR, or in separate (inverse) PCR reactions that may be pooled later. Multiplex PCR is to be preferred in cases when nucleotide sequences of interest interacting with different target nucleotide sequences can be identically labelled without compromising the analysis. Amplification will be done separately for each target nucleotide sequence when each set of DNA-DNA interactions belonging to a given target sequence needs to be labelled differently and/or when inverse PCR primer sets interfere with each other's amplification efficiency.

Identification of Intrachromosomal Rearrangements Such as Deletions, Insertions and Duplications and (Balanced and Unbalanced) Inversions.

In one preferred embodiment, all amplified DNA sequences interacting with the set of target sequences from a test sample (e.g. a patient sample) are identically labelled and genome-wide interaction frequencies are compared with these of a control sample (e.g. from healthy subject). Control and test samples can be hybridised to the same array in different colours, or they can be hybridised to different arrays and compared. An increase or a decrease in DNA-DNA interaction frequency for the test sample compared to the control sample is indicative for a duplication/insertion or a deletion in the test sample. It can also be indicative for an inversion.

Figure 18:
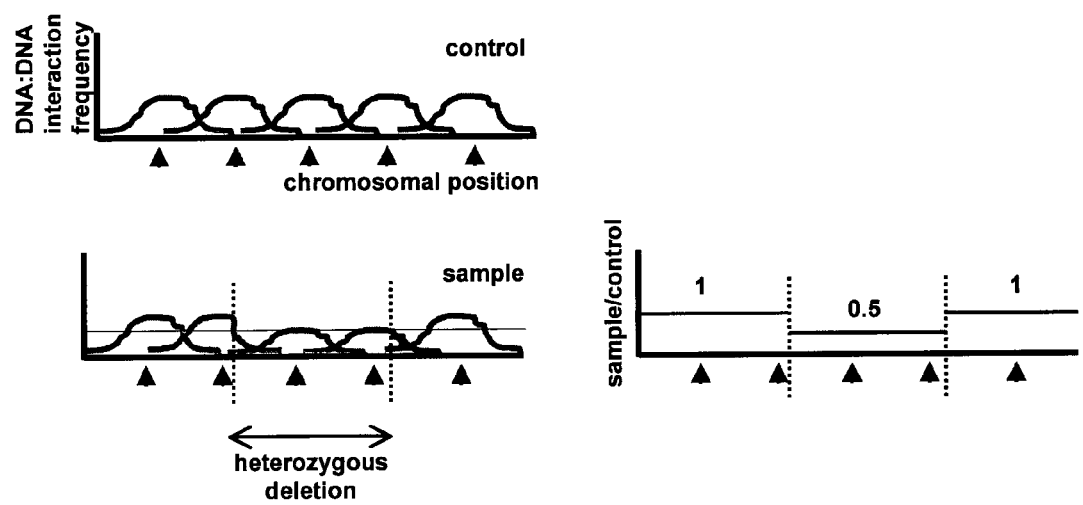
Figure 19:
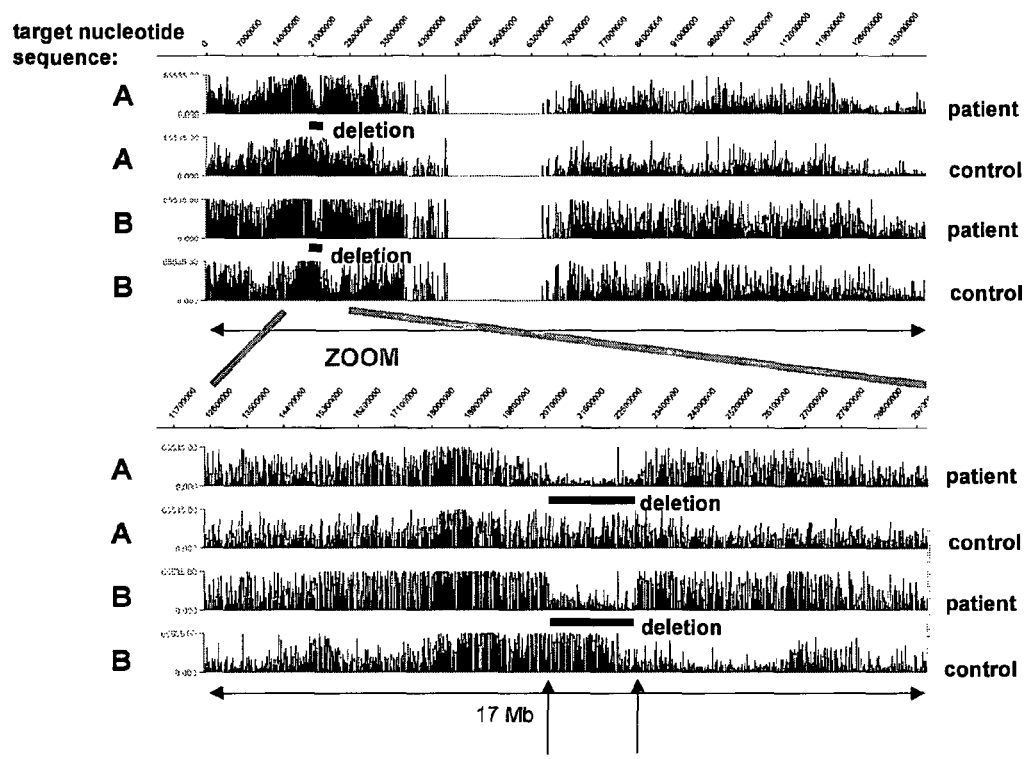

FIGS. 18 and 19 show a deletion identified by 4C in this manner.

In another preferred embodiment, amplified DNA sequences interacting with the set of target sequences from a test sample (e.g. patient sample) are labelled in two colours, with colours alternating for target sequences that neighbour on the linear chromosome template. Neighbouring target sequences are close enough on the linear chromosome template for their interacting sequences to be overlapping. Thus, neighbouring target sequences may be, for example, 5, 10, 15, 20, 25, 30, 35, 40, 45 to 50 Mb away from each other. Such an experimental design prevents that rearrangements are missed due to saturated hybridisation signals close to a given target sequence. Genome-wide interaction frequencies are compared with these of a control sample (e.g. from healthy subject). Control and test samples can be differentially labelled and hybridised to the same array, or they can be hybridised to different arrays and compared. An increase or a decrease in DNA-DNA interaction frequency for the test sample compared to the control sample is indicative for a duplication/insertion or a deletion in the test sample. It can also be indicative for an inversion.

Figure 20:
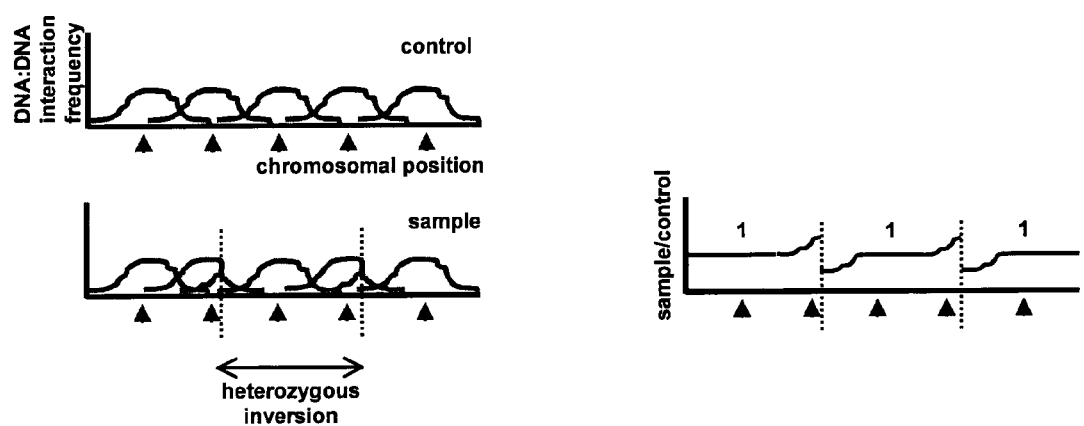

A subsequent 4C analysis directed to target sequences flanking or inside the rearranged part of the genome can be performed to identify inversions. An inversed pattern of hybridisation signals as compared to a control sample identifies the inversion in the test sample. This is depicted in FIG. 20.

Figure 21:
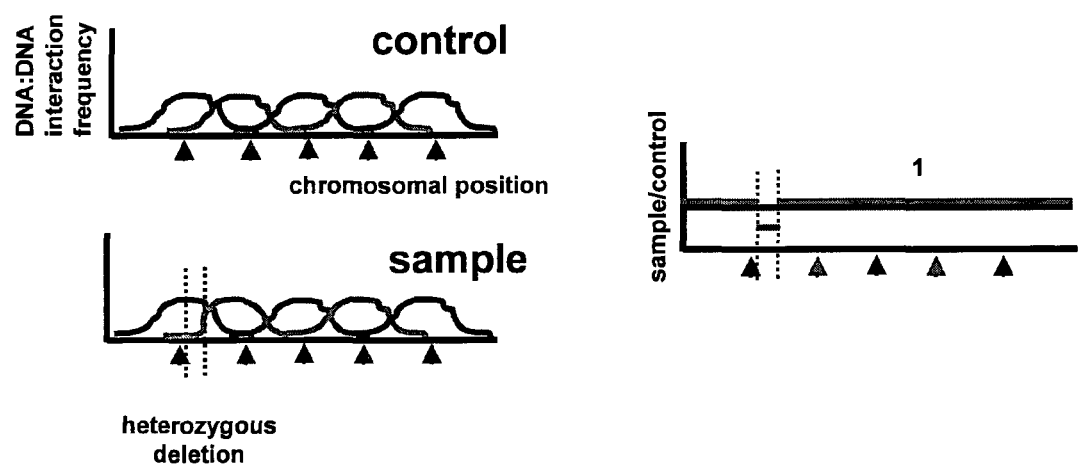
Figure 22:
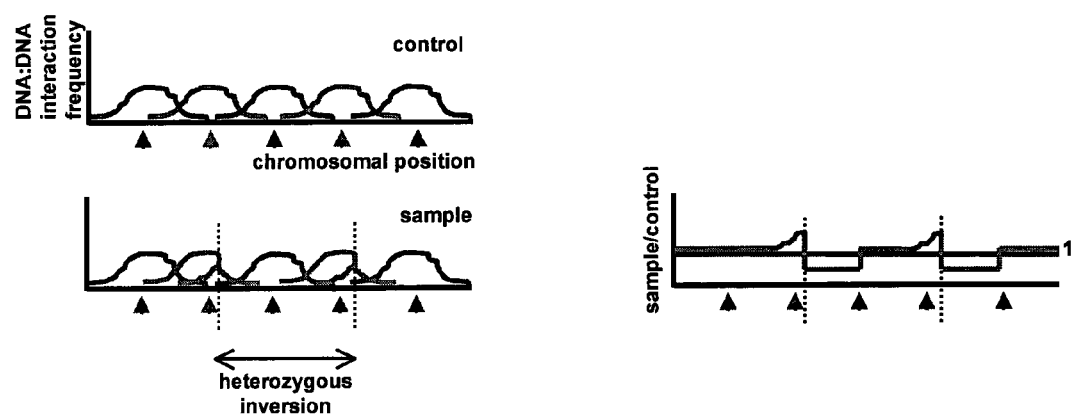
Figure 23:
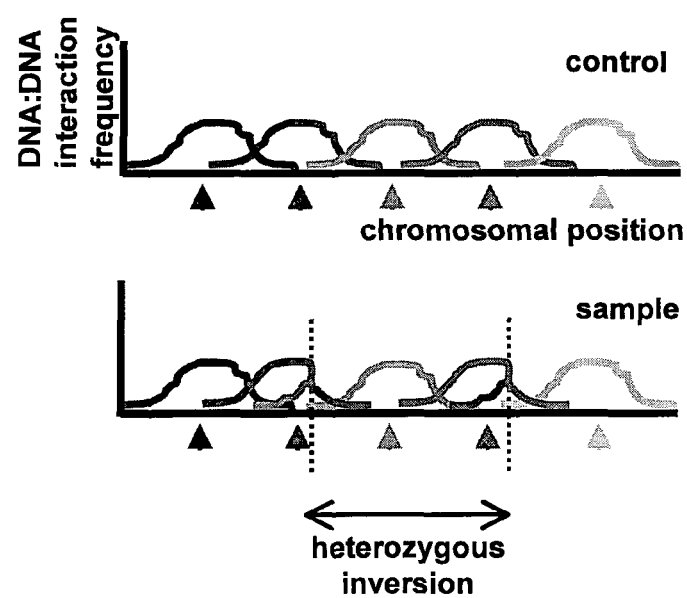

In a further preferred embodiment, nucleotide sequences of interest interacting with different target sequences juxtaposed on the chromosome template are labelled with different dyes. Rearrangements are detected by the appearance or disappearance of interacting DNA signals in the patient sample compared to the control sample. This is depicted in FIGS. 21 to 23.

Identification of Balanced and Unbalanced Translocations.

In a further preferred embodiment, multiple dyes are available (e.g. 48 dyes) and each chromosome is labelled with two unique dyes that are used such that the dyes alternate between target sequences that neighbour on the linear chromosome template. All DNA fragments can be hybridised together to an array containing probes representing the complete genome. The identification of DNA-DNA interactions between chromosomes that occur in test samples but not control samples are indicative for a translocation and identify the two rearranged chromosomes. The transition from low to high signals on an unrelated chromosome identifies the primary restriction enzyme recognition site near the DNA breakpoint.

Figure 24:
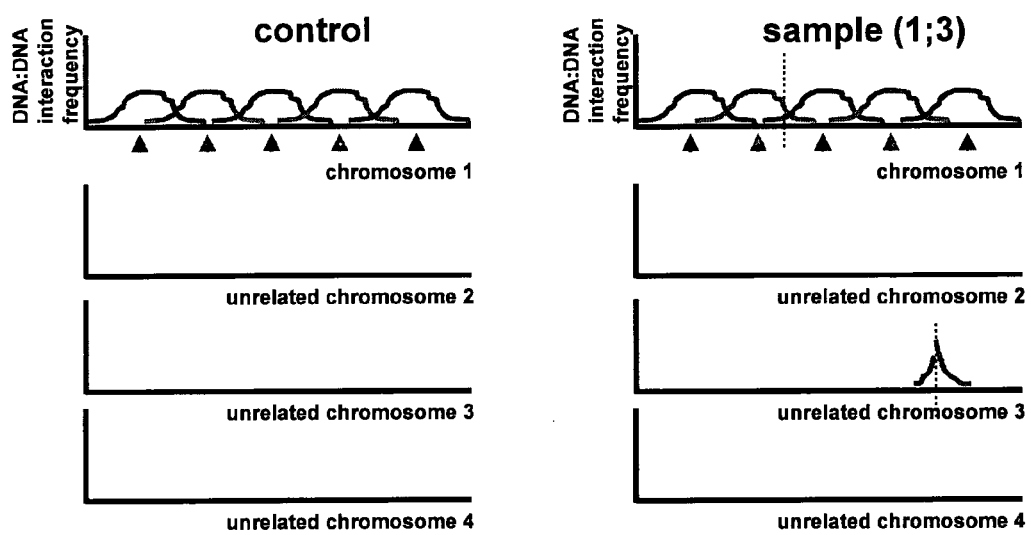

If translocations are balanced, each of the two chromosome-specific dyes should give strong hybridisation signals on a mutually exclusive set of probes directly neighbouring each other on the linear template of the unrelated chromosome. The breakpoint on this unrelated chromosome is located in between the two sets of probes showing positive hybridisation signals. See FIG. 24.

Figure 25:
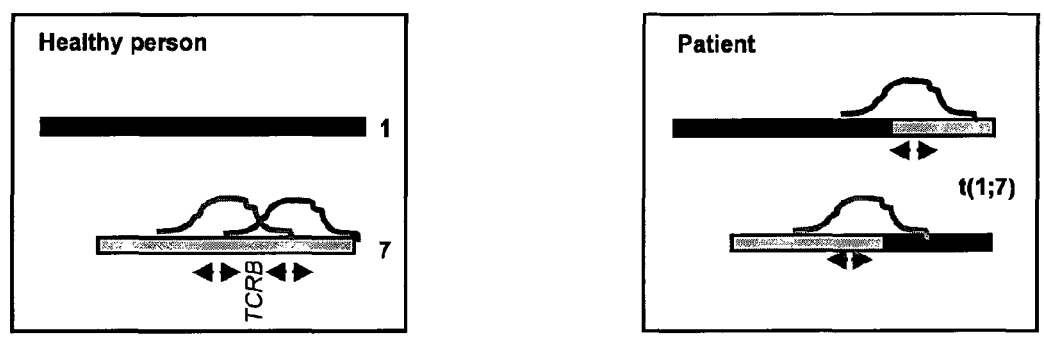
Figure 25:
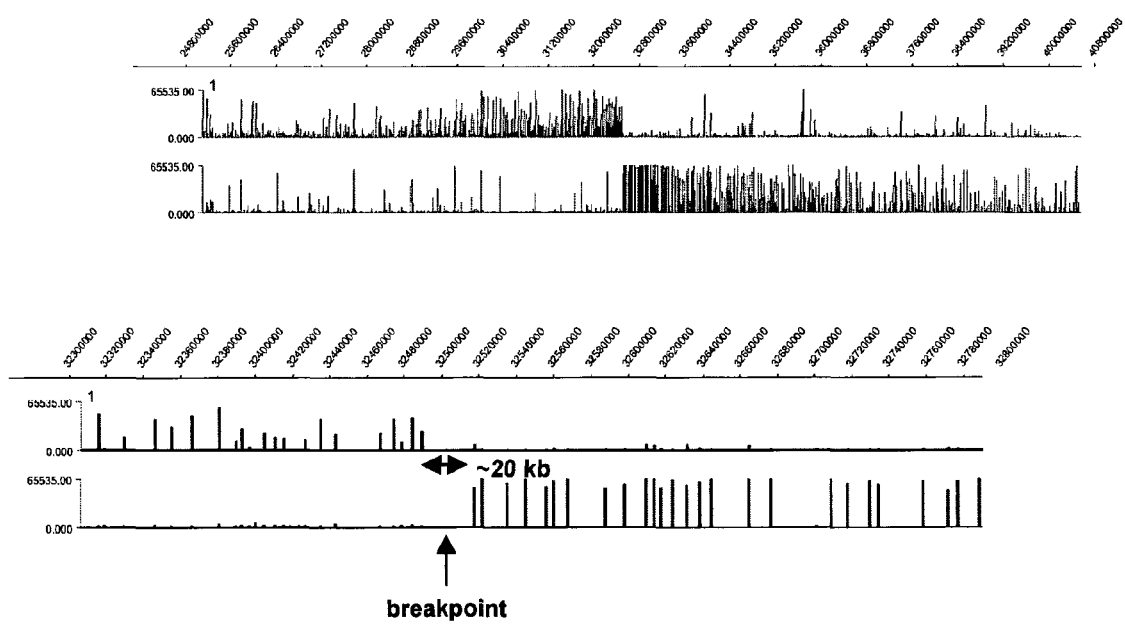

When tested on a patient sample involving a chromosome 1:chromosome 7 translocation the results shown in FIG. 25 are obtained. In this particular sample the target sequences on the array represented a selection of sequences located next to HindIII sites (see above for the derivation of target sequences).

Figure 26:
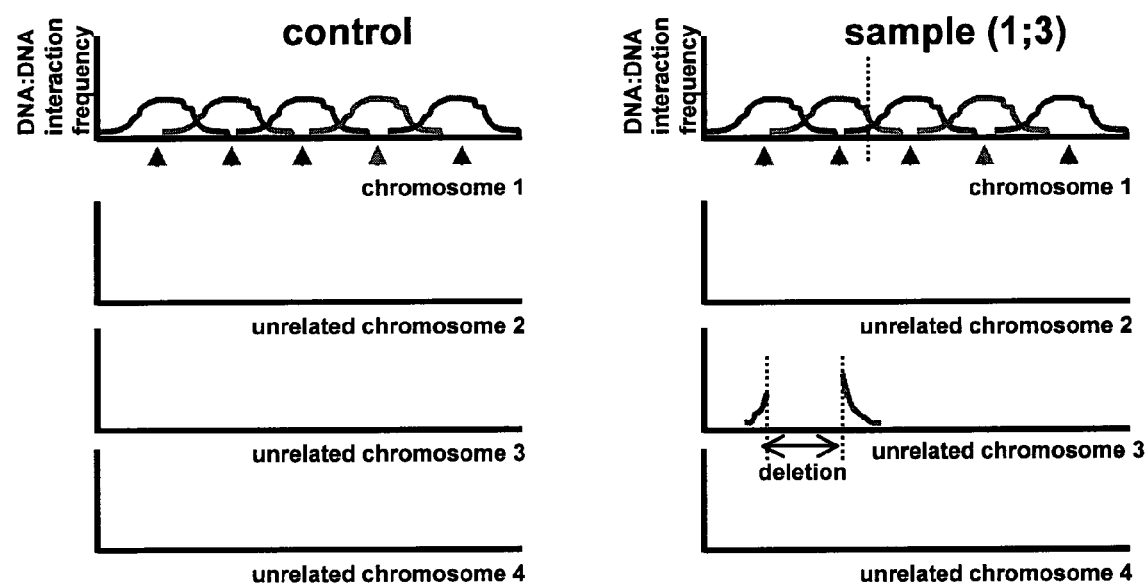

If translocations occurred with loss of DNA at the breakpoints (i.e. unbalanced translocations), each of the two chromosome-specific dyes will give strong hybridisation signals on a mutually exclusive set of probes on the unrelated chromosome that do not directly neighbour each other on the linear template of the unrelated chromosome. The probes located on the unrelated chromosome in between the two sets of probes showing inter-chromosomal DNA-DNA interactions represent the genomic region that was lost. The most outer probes of this region mark the restriction sites near the breakpoints on the unrelated chromosome (see FIG. 26).

Figure 27:
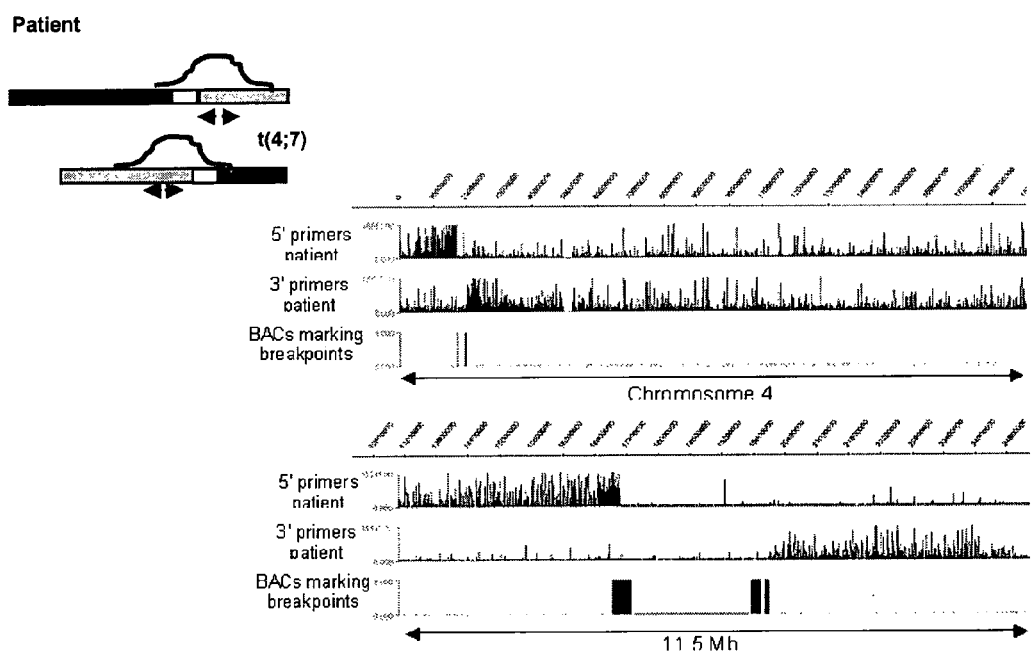

When tested on a patient sample involving a chromosome 4:chromosome 7 translocation with an unknown amount of deleted DNA at the breakpoint the results shown in FIG. 27 are obtained. In this particular sample the target sequences on the array again represented a, selection of sequences located next to HindIII sites. The result shows that both the translocation and the deletion (approx 2 Mb) are detected.

Figure 28:
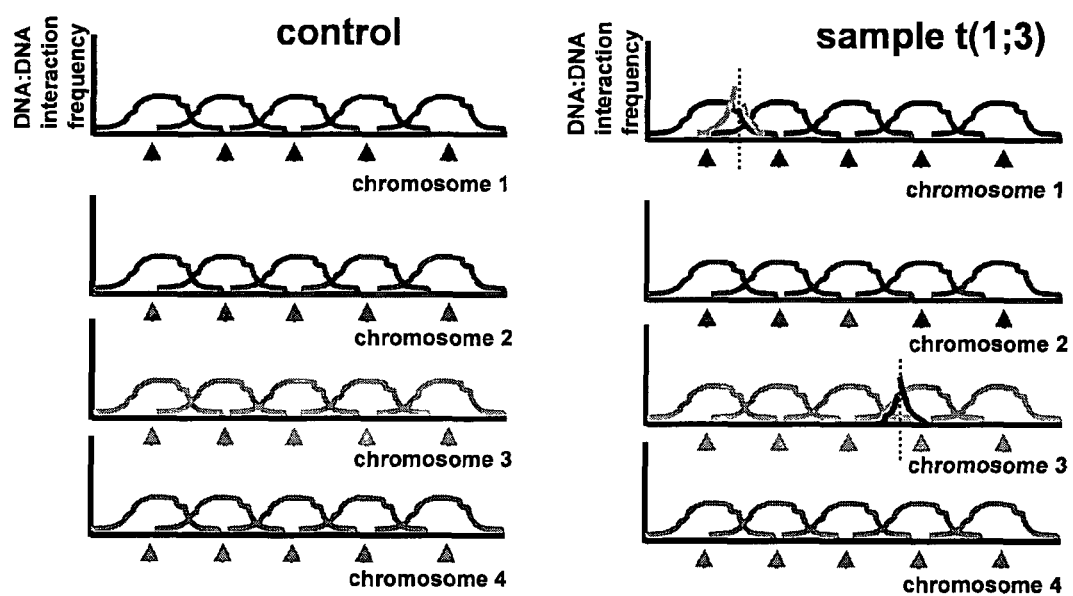

In a still further preferred embodiment, multiple dyes (e.g. 24 dyes) are available and used to differentially label each chromosome (FIG. 28). Thus, all DNA sequences that interact with target sequences present on the same chromosome are labelled identically and different from those located on other chromosomes. The identification of DNA-DNA interactions between chromosomes that occur in test samples but not control samples are indicative for a translocation and identify the two rearranged chromosomes.

A subsequent 4C analysis directed specifically towards the chromosomes involved in the translocation allows the identification of breakpoints. Here, one or each chromosome is labelled with two unique dyes that are used such that they alternate between DNA fragments interacting with target sequences that neighbour on the linear chromosome template.

If translocations are balanced, each of the two chromosome-specific dyes should give strong hybridisation signals on a mutually exclusive set of probes directly neighbouring each other on the linear template of the unrelated chromosome. The breakpoint on this unrelated chromosome is located in between the two sets of probes showing positive hybridisation signals.

If translocations occurred with loss of DNA at the breakpoints (i.e. unbalanced translocations), each of the two chromosome-specific dyes will give strong hybridisation signals on a mutually exclusive set of probes on the unrelated chromosome that do not directly neighbour each other on the linear template of the unrelated chromosome. The probes located on the unrelated chromosome in between the two sets of probes showing inter-chromosomal DNA-DNA interactions represent the genomic region that was lost. The most outer probes of this region mark the restriction sites near the breakpoints on the unrelated chromosome.

In another preferred embodiment, less than 24 dyes are available and each dye is used to uniquely label all DNA fragments that interact with target sequences present on the same chromosome. Thus, with 1, 2, 3, 4, 6, 8, 10, 12 etc dyes, 1, 2, 3, 4, 6, 8, 10, 12 etc. chromosomes can be labelled uniquely. Labelled DNA fragments belonging to each of these chromosomes can be hybridised together to an array containing probes representing the complete genome. The appearance of hybridisation signals representing DNA-DNA interactions on an unrelated chromosome identifies this chromosome as a translocation partner. A subsequent 4C analysis directed specifically towards the chromosomes involved in the translocation allows the identification of breakpoints (as described above).

In another preferred embodiment, less than 48 dyes are available and each chromosome is labelled with two unique dyes that are used such that they alternate between DNA fragments interacting with target sequences that neighbour on the linear chromosome template. Thus, with 2, 4, 6, 8, 10, 12, 14, 16, 18, 20, 22, 24 etc dyes 1, 2, 3, 4, 5, 6, 7, 8, 9, 10, 11, 12 etc. chromosomes can be labelled uniquely. All DNA fragments can be hybridised together to an array containing probes representing the complete genome. Hybridisation signals on an unrelated chromosome represent inter-chromosomal DNA-DNA interactions and identify this chromosome as a translocation partner. The transition from low to high signals on an unrelated chromosome identifies the primary restriction enzyme recognition site near the DNA breakpoint.

In a yet further preferred embodiment, less than 48 dyes are available and each chromosome is labelled with more than two unique dyes that are used such that they alternate between DNA fragments interacting with target sequences that neighbour on the linear chromosome template. All DNA fragments can be hybridised together to an array containing probes representing the complete genome. Hybridisation signals on an unrelated chromosome represent inter-chromosomal DNA-DNA interactions and identify this chromosome as a translocation partner. The transition from low to high signals on an unrelated chromosome identifies the primary restriction enzyme recognition site near the DNA breakpoint.

How to Identify Other Translocation Breakpoints

Breakpoints identified on one chromosome according to any of the strategies mentioned above can subsequently be used to identify breakpoints on the translocating partner chromosome. This can be done for example via sequencing of products obtained through long-range PCR over DNA junctions or ligation-mediated (LM-)PCR or inverse PCR on DNA circles created by restriction enzyme digestion and religation of (non-crosslinked) genomic DNA, using primers specific for the one chromosome that read into sequences of the other chromosome.

In one preferred embodiment, each of the aforementioned screens for genomic rearrangements may be followed by a dedicated 4C experiment directed against target sequences near candidate breakpoints to unambiguously identify them as such.

Aspects of the methods described above for the detection of different types of genomic rearrangements may be combined to simultaneously screen the genome for their occurrence.

If genomic tiling arrays are used instead of 4C arrays, transitions in signal intensities for probes juxtaposed on the linear chromosome template that are observed in patient, but not in control, samples, indicate the position of breakpoints associated with a genomic rearrangement (instead of the primary restriction enzyme recognition site near the DNA breakpoint).

Sequencing

High throughput DNA sequencing promises to become an affordable and more quantitative alternative for micro-arrays to analyse large collections of DNA sequences. Examples or high-throughput sequencing approaches are listed in E. Y. Chan, Mutation Research 573 (2005) 13-40 and include, but are not limited to, near-term sequencing approaches such as cycle-extension approaches, polymerase reading approaches and exonuclease sequencing, revolutionary sequencing approaches such as DNA scanning and nanopore sequencing and direct linear analysis. Examples of current high-throughput sequencing methods are 454 (pyro)sequencing, Solexa Genome Analysis System, Agencourt SOLiD sequencing method (Applied Biosystems), MS-PET sequencing (Ng et al., 2006, nar.oxfordjournals.org/cgi/content/full/34/12/e84).

Sequencing can replace array hybridisation in high-throughput analysis of the results of 4C and other approached based on detection of genomic interactions. The frequency of occurrence of a sequence is indicative of the frequency of association in the genome, and can be analysed in the same way as the hybridisation results are analysed in the foregoing.

Sequencing is performed on the template as provided by steps a-g, described in claim 1. Alternatively, the sequencing can be performed on the PCR products obtained by methods as described by Lomvardas et al., Cell 126, 403-413, Jul. 28, 2006 or by Ling et al., Science 312, 14 Apr. 2006, 269-272.

Sequencing is initiated from one or both ends of the PCR products. Both ends of the PCR product consist of nucleotide sequences of known nucleotide composition, with at least one end being target nucleotide sequence, and flank a nucleotide sequence of interest that was interacting and ligated to the target nucleotide sequence. Depending on the sequencing method used, adapters may need to be added to one or both ends of the PCR products. Adapters may be oligonucleotide sequences required for the sequencing method of interest, which may or may not contain moieties that for example allow them to be captured. Adapters may be ligated to the PCR products directly or after blunting the ends of the PCR products. Alternatively, PCR primer sets, as used in step g (claim 1), may contain overhangs that represent adapter sequences or may contain overhangs that introduce restriction enzyme cleavage sites that can be used for subsequent ligation of adapters specific or non-specific for each end of the PCR product.

In 4C experiments that aim to identify the DNA sequences interacting with a single nucleotide target sequence, sequencing needs to read across the primary ligation event (step c) and/or the secondary ligation event (step f) such that sufficient sequence information is obtained to identify the nucleotide sequences of interest. Typically, this requires the sequencing and identification of stretches of minimally 8-30 nucleotides beyond the ligation junction into the nucleotide sequence of interest (see FIG. 28).

In multiplex 4C sequencing needs to read across the primary ligation event (step c) and/or the secondary ligation event (step f) such that sufficient sequence information is obtained to identify both the target nucleotide sequence and the nucleotide sequence of interest that together form the ligation product. Typically, this requires the sequencing and identification of stretches of 8-30 nucleotides at each side of the ligation junction. The identification of the target nucleotide sequence will provide each ligation product with a 'home address'. Primers used in step g that hybridise to the target nucleotide sequence need to be located at a distance from the primary and secondary ligation junction that is far enough for sequencing to unambiguously identify this. 'home address'. Depending on the method of sequencing, this distance may minimally be 0, 10, 20 30, 40, 50, 60, 70, 80, 90 or 100 nucleotides away from the ligation junction.

Figure 29:
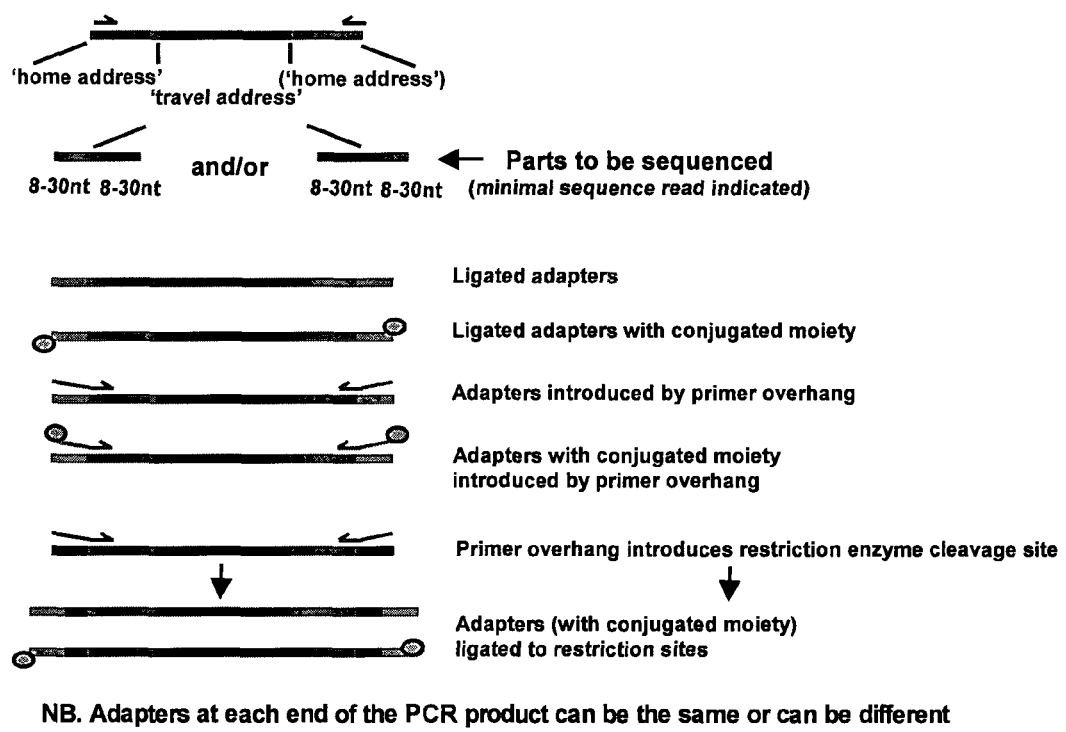

In single-plex and multiplex 4C, when PCR products consist of a nucleotide sequence of interest flanked on each side by target nucleotide sequences, reading from the one end of the PCR product across the primary ligation junction, and reading from the other end of the PCR product across the secondary ligation junction, provides the same information. Thus, sequences obtained from one side of the PCR product are sufficient for the analysis of DNA-DNA interactions. Sequences obtained from the other side of the PCR product may be used to complement or to verify data. See FIG. 29.

Priming of the actual sequence reactions can be done using the standard primers routinely used by the respective high-throughput sequencing platforms. It can also be done with custom-made sequencing primers that partially or completely overlap the inverse PCR primers used to amplify sequences captured by a given target sequence. This would prevent re-reading the entire inverse PCR primer sequence and allow the reading of more nucleotides of the captured fragment, which therefore can be identified more easily and mapped to the genome. These custom-made sequencing primers may then also partially anneal to the adapter sequences normally used as the DNA strand complementary to the sequencing primer.

In a multiplex set-up, multiple sequencing primers that overlap both with the adapter sequence and with the outer ends of the inverse PCR amplified DNA products can be used simultaneously, such that each target fragment included in the analysis has its own unique sequence primer. The overlap with the outer ends of the inverse PCR amplified DNA products (ie. the inverse PCR primer sequence) should be such that sufficient nucleotides of the target sequence are still available for sequencing and such that each target sequence (home-address) can be identified unambiguously. Depending on the nature and number of target sequences analysed simultaneously, this means that in one embodiment, the sequencing primers may hybridise 1 to 20 nucleotides away from the restriction site that forms the junction between the target sequence and the captured sequence. The identification of each combination of target sequence and captured sequence may also be done using di-tag sequencing, which provides sequence information of both ends of each DNA fragment analysed.

In another embodiment, the sequencing primers are designed for each target sequence such that they are close to the primary and/or secondary restriction enzyme recognition sites analysed and may overlap partially or completely with the primary and/or secondary restriction enzyme recognition sites analysed.

In one embodiment, the high throughput sequencing technology used is the Solexa (Illumina) sequencing.

In one embodiment, sequencing may be directed to the side of the primary restriction enzyme recognition site. This may prevent reading random ligation events that occur during the second ligation step.

In one embodiment, sequencing may be directed to the side of the secondary restriction enzyme recognition site.

Data Analysis

Ligation products analysed by 4C technology are composed of a 'home address' (target nucleotide sequence) and an interacting nucleotide sequence of interest ('travel address'). In the case of single-plex 4C this 'home address' is known (being the one target nucleotide sequence analysed).

In cases of multiplex 4C, the 'home address' is identified by electronically comparing the obtained target nucleotide sequence against a library/database containing all target nucleotide sequences included in the analysis. The obtained 'travel address' (i.e. nucleotide sequence of interest) is identified by electronically comparing its sequence to a library/database containing all genomic DNA fragments that are located between a primary and secondary restriction enzyme recognition site of choice.

To visualise the data and facilitate the analysis, in a preferred embodiment each sequenced ligation product is plotted graphically along the linear template of the chromosomes, at the genomic location of the 'travel address' (nucleotide sequence of interest). Unique colour codes reveal the 'home address' of each ligation product and the frequency of detection of each ligation product is indicated graphically. Genomic rearrangements can be detected by dividing each interaction frequency measured in the one sample (e.g. obtained from a patient) over those measured in the other sample (e.g. from healthy subject). These values can be plotted along the linear chromosome templates as well.

A decrease in DNA-DNA interaction frequency in the test sample is indicative for a deletion. Typically, this coincides with an increase in DNA-DNA interaction frequencies for sequences beyond the most distal breakpoint as measured from the target sequence. An increase in DNA-DNA interaction frequency in the test sample is indicative for a duplication. Typically, this coincides with a decrease in DNA-DNA interaction frequencies for sequences beyond the most distal breakpoint as measured from the target sequence. An inversion in DNA-DNA interaction frequency in the test sample is indicative for a genomic inversion. The detection of DNA-DNA interactions across chromosomes is indicative for a translocation. Breakpoints are detected as described for the micro-array analysis.

Biomarkers

The identification of rearrangements—such as translocations, inversions and deletions, which are associated with a disease allows the identification of biomarkers which can be used to diagnose the disease. For example, hybridisation probes or PCR primers can be designed which detect a given rearrangement, and used to diagnose the disease in a patient. PCR probes can be designed according to techniques known in the art, such that a region susceptible to rearrangement in a disease state is amplified using the primers; the nature of the amplification product will be indicative of the presence or absence of the disease. Alternatively, hybridisation probes or primers can be designed which will hybridise exclusively in the presence or absence of the rearrangement. Fusion proteins resulting from rearrangements can be detected by techniques such as antibody detection with antibodies designed according to techniques known in the art or mass spectrometry.

Subject

The term "subject" includes mammals—such as animals and humans.

Agent

The agent may be an organic compound or other chemical. The agent may be a compound, which is obtainable from or produced by any suitable source, whether natural or artificial. The agent may be an amino acid molecule, a polypeptide, or a chemical derivative thereof, or a combination thereof The agent may even be a polynucleotide molecule—which may be a sense or an anti-sense molecule, or an antibody, for example, a polyclonal antibody, a monoclonal antibody or a monoclonal humanised antibody.

Various strategies have been developed to produce monoclonal antibodies with human character, which bypasses the need for an antibody-producing human cell line. For example, useful mouse monoclonal antibodies have been "humanised" by linking rodent variable regions and human constant regions (Winter, G. and Milstein, C. (1991) Nature 349, 293-299). This reduces the human anti-mouse immunogenicity of the antibody but residual immunogenicity is retained by virtue of the foreign V-region framework. Moreover, the antigen-binding specificity is essentially that of the murine donor. CDR-grafting and framework manipulation (EP 0239400) has improved and refined antibody manipulation to the point where it is possible to produce humanised murine antibodies which are acceptable for therapeutic use in humans. Humanised antibodies may be obtained using other methods well known in the art (for example as described in U.S. Pat. No. 239,400).

The agents may be attached to an entity (e.g. an organic molecule) by a linker which may be a hydrolysable bifunctional linker.

The entity may be designed or obtained from a library of compounds, which may comprise peptides, as well as other compounds, such as small organic molecules.

By way of example, the entity may be a natural substance, a biological macromolecule, or an extract made from biological materials such as bacteria, fungi, or animal (particularly mammalian) cells or tissues, an organic or an inorganic molecule, a synthetic agent, a semi-synthetic agent, a structural or functional mimetic, a peptide, a peptidomimetics, a peptide cleaved from a whole protein, or a peptides synthesised synthetically (such as, by way of example, either using a peptide synthesizer or by recombinant techniques or combinations thereof, a recombinant agent, an antibody, a natural or a non-natural agent, a fusion protein or equivalent thereof and mutants, derivatives or combinations thereof.

Typically, the entity will be an organic compound. For some instances, the organic compounds will comprise two or more hydrocarbyl groups. Here, the term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. For some applications, preferably the entity comprises at least one cyclic group. The cyclic group may be a polycyclic group, such as a non-fused polycyclic group. For some applications, the entity comprises at least the one of said cyclic groups linked to another hydrocarbyl group.

The entity may contain halo groups—such as fluoro, chloro, bromo or iodo groups.

The entity may contain one or more of alkyl, alkoxy, alkenyl, alkylene and alkenylene groups—which may be unbranched- or branched-chain.

Disease

Aspects of the present invention may be used for the treatment and/or prevention and/or diagnosis and/or prognosis of a disease—such as those listed in WO-A-98/09985.

For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; diseases associated with viruses and/or other intracellular pathogens; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue. Specific cancer related disorders include but not limited to: solid tumours; blood born tumours such as leukemias; tumor metastasis; benign tumours, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; wound granulation; corornay collaterals; cerebral collaterals; arteriovenous malformations; ischeniic limb angiogenesis; neovascular glaucoma; retrolental fibroplasia; diabetic neovascularization; heliobacter related diseases, fractures, vasculogenesis, hematopoiesis, ovulation, menstruation and placentation.

Preferably, the disease is cancer—such as acute lymphocytic leukemia (ALL), acute myeloid leukemia (AML), adrenocortical cancer, anal cancer, bladder cancer, blood cancer, bone cancer, brain tumor, breast cancer, cancer of the female genital system, cancer of the male genital system, central nervous system lymphoma, cervical cancer, childhood rhabdomyosarcoma, childhood sarcoma, chronic lymphocytic leukemia (CLL), chronic myeloid leukemia (CML), colon and rectal cancer, colon cancer, endometrial cancer, endometrial sarcoma, esophageal cancer, eye cancer, gallbladder cancer, gastric cancer, gastrointestinal tract cancer, hairy cell leukemia, head and neck cancer, hepatocellular cancer, Hodgkin's disease, hypopharyngeal cancer, Kaposi's sarcoma, kidney cancer, laryngeal cancer, leukemia, liver cancer, lung cancer, malignant fibrous histiocytoma, malignant thymoma, melanoma, mesothelioma, multiple myeloma, myeloma, nasal cavity and paranasal sinus cancer, nasopharyngeal cancer, nervous system cancer, neuroblastoma, non-Hodgkin's lymphoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, prostate cancer, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and Wilms' tumor.

Kits

The materials for use in the methods of the present invention are ideally suited for preparation of kits.

Such a kit may comprise containers, each with one or more of the various reagents (typically in concentrated form) utilised in the methods described herein, including, for example, a primary restriction enzyme, a secondary restriction enzyme, a cross-linking agent, a ligation enzyme (eg. a ligase) and an agent to reverse the cross-linking (eg. proteinase K).

Oligonucleotides may also be provided in containers which can be in any form, e.g., lyophilized, or in solution (e.g., a distilled water or buffered solution), etc.

In a preferred aspect of the present invention, there is provided a kit comprising a set of probes as described herein, an array and optionally one or more labels.

A set of instructions will also typically be included.

Uses

Advantageously, the present invention can be used in order to obtain information about the spatial organisation of nucleotide sequences—such as genomic loci in vitro or in vivo.

By way of example, 4C technology can be used to study the three dimensional organisation of one or more gene loci. In particular, this technology can be used to study the role of one or more transcription factors in the three dimensional organisation of one or more gene loci.

By way of further example, 4C technology can be used to study the role of trans-acting factors and cis-regulatory DNA elements.

By way of further example, 4C technology can be used to study long range gene regulation in vitro or in vivo.

By way of further example, 4C technology can be used to study intra-chromosomal proximity and interaction.

By way of further example, 4C technology can be used to study inter-chromosomal proximity and interaction.

By way of further example, 4C technology can be used to identify nucleotide sequences that function with a promoter, enhancer, silencer, insulator, locus control region, origin of replication, MAR, SAR, centromere, telomere or any other sequence of interest in a regulatory network.

By way of further example, 4C technology can be used to identify genes responsible for a phenotype (disease) in cases where a mutation and/or deletion happens to affect a distant regulatory element and their mapping therefore fails to provide such information.

By way of further example, 4C technology can be used to eventually reconstruct the spatial conformation of gene loci, large genomic regions or even complete chromosomes.

By way of further example, 4C technology can be used to define potential anchor sequences that keep certain chromosomes together in the nuclear space.

By way of further example, 4C technology can be used to eventually reconstruct at high resolution the positioning of chromosomes with respect to each other.

By way of further example, 4C technology can be used in diagnosis (eg. prenatal diagnosis) to detect or identify genomic rearrangements and/or aberrations—such as translocations, deletions, inversions, duplications.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J.

Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

The invention will now be further described by way of Example, which are meant to serve to assist one of ordinary skill in the art in carrying out the invention and are not intended in any way to limit the scope of the invention.

Example 1

Materials & Methods Section that Goes with FIG. 2, 13, 14, 15, 16, 17, 19

4C Technology

The initial steps of the 3C technology procedure were performed as described previously (Splinter et al. (2004). *Methods Enzymol* 375, 493-507 (2004), yielding ligation products between HindIII fragments. This HindIII-ligated 3C template (~50 µg) was digested overnight at 100 ng/µl with 50 U of a secondary, frequent cutting, restriction enzyme, being either DpnII (HS2, Rad23A) or NlaIII (β-major). To avoid constraints in DNA circle formation (Rippe et al. (1995) *Trends Biochem Sci* 20, 500-6), care was taken to choose a secondary restriction enzyme that did not cut within about 350-400 bp from the HindIII restriction site that demarcates the restriction fragment of interest (i.e. the 'bait'). After secondary restriction enzyme digestion, DNA was phenol extracted, ethanol precipitated and subsequently ligated at low concentration (50 µg sample in 14 ml using 200 U ligase (Roche), 4 hours at 16° C.) to promote DpnII- or DpnII-circle formation. Ligation products were phenol extracted and ethanol precipitated, using glycogen (Roche) as a carrier (20 µg/ml). The circles of interest were linearised by digesting overnight with a 50 U of a tertiary restriction enzyme that cuts the bait in between the primary and secondary restriction enzyme recognition sites, using the following restriction enzymes: SpeI (HS2), PstI (Rad23A) and PflmI (β-major). This linearisation step was performed to facilitate subsequent primer hybridization during the first rounds of PCR amplification. Digested products were purified using a QIAquick nucleotide removal (250) column (Qiagen).

PCR reactions were performed using the Expand Long Template PCR system (Roche), using conditions carefully optimized to assure linear amplification of fragments sized up to 1.2 kb (80% of 4C-PCR fragments are smaller than 600 bp). PCR conditions were as follows: 94° C. for 2 minutes, 30 cycles of 94° C. for 15 seconds, 55° C. for 1 minute and 68° C. for 3 minutes, followed by a final step of 68° C. for 7 minutes. The maximum amount of template that still shows linear range of amplification was determined. For this, serial dilutions of template were added to PCR reactions, amplified DNA material was run out on an agarose gel and PCR products were quantified using ImageQuant software. Typically, 100-200 ng of template per 50 µl PCR reaction gave products in the linear range of amplification. 16 to 32 PCR reactions were pooled and purified this 4C template using the QIAquick nucleotide removal (250) system (Qiagen). Purified 4C template was labeled and hybridized to arrays according to standard ChIP-chip protocols (Nimblegen Systems of Iceland, LLC). Differentially labeled genomic DNA, which was digested with the primary and secondary enzyme used in the 4C procedure, served as a control template to correct for differences in hybridisation efficiencies. For each experiment two independently processed samples were labeled with alternate dye orientations.

```
4C-Primer-sequences used:

HS2:
5'-ACTTCCTACACATTAACGAGCC-3',      (SEQ ID NO: 1)

5'-GCTGTTATCCCTTTCTCTTCTAC-3'      (SEQ ID NO: 2)

Rad23A:
5'-TCACACGCGAAGTAGGCC-3',          (SEQ ID NO: 3)

5'-CCTTCCTCCACCATGATGA-3'          (SEQ ID NO: 4)

β-major:
5'-AACGCATTTGCTCAATCAACTACTG-3',   (SEQ ID NO: 5)

5'-GTTGCTCCTCACATTTGCTTCTGAC-3'    (SEQ ID NO: 6)
```

4C Arrays

Arrays and analysis were based on NCBI build m34. Probes (60-mers) were selected from the sequences 100 bp up—and downstream of HindIII sites. The CG-content was optimized towards 50%, for uniform hybridization signals. To prevent cross-hybridization, probes that had any similarity with highly abundant repeats (RepBase 10.09)[3] were removed from the probe set. In addition, probes that gave more than two BLAST hits in the genome were also removed from the probe set. Sequence alignments were performed using MegaBLAST (Zhang et al. (2000) *J Comput Biol* 7, 203-14) using the standard settings. A hit was defined as an alignment of 30 nt or longer.

4C Data Analysis

The signal ratio 4C-sample/genomic DNA was calculated for each probe and the data was visualized with SignalMap software provided by Nimblegen Systems. Data were analyzed using the R package (http://www.r-project.org), Spotfire and Excel. Unprocessed hybridization ratios showed clusters of 20-50 positive 4C-signals along the chromosome template. To define these clusters, a running mean was applied. Various window sizes were used, ranging from 9-39 probes, which all identified the same clusters. Results shown were based on a window size of 29 probes (on average 60 kb) and were compared to the running mean performed across randomized data. This was done for each array separately. Consequently, all measurements were appreciated relative to the amplitude and noise of that specific array. The False Discovery Rate (FDR), defined as (no. false positives)/(no. of false positives+no. of true positives) was determined as follows: (number of positives in the randomised set)/(number of positives in the data). The threshold level was determined using a top down approach to establish the minimal value for which: FDR<0.05.

Next, biological duplicate experiments were compared. Windows that met the threshold in both duplicates were considered positive. When comparing randomized data, no windows were above threshold in both duplicates. Positive windows directly adjacent on the chromosome template were joined (no gaps allowed), creating positive areas.

Expression Analysis

For each tissue, three independent microarrays were performed according to Affymetrix protocol (mouse 430_2 arrays). Data were normalized using RMA ca-tools; www-.bioconductor.org) and for each probe-set the measurements of the three microarrays were averaged. In addition, when multiple probe-sets represented the same gene, they were also averaged. Mas5calls (Affy library: www.bioconductor.org) was used to establish "present", "absent" and "marginal" calls. Genes with a "present" call in all three arrays and an expression value bigger than 50 were called expressed. 'Fetal liver-specific genes' were classified as genes that met our criteria of being expressed in fetal liver and had more than five times higher expression values compared to fetal brain. To provide a measure of overall transcriptional activity around each gene, a running sum was applied. For this, we used log-transformed expression values. For each gene we calculated the sum of the expression of all genes found in a window 100 kb upstream of the start and 100 kb downstream of the end of the gene, including the gene itself. Resulting values for active genes found inside positive 4C regions (n=124, 123 and 208 respectively for HS2 in liver, Rad23A in brain and Rad23A in liver) were compared to the values obtained for active genes outside positive 4C areas (n=153, 301 and 186, respectively, where n=153 corresponds to the number of active, non-interacting, genes present between the most centromeric interacting region and the telomere of chromosome 7); the two groups were compared using a one tailed Wilcoxon rank sum test.

FISH Probes

The following BAC clones (BACPAC Resources Centre) were used; RP23-370E12 for

Hbb-1, RP23-317H16 for chr.7 at 80.1 Mb (OR gene cluster), RP23-334E9 for Uros, RP23-32C19 for chr.7 at 118.3 Mb, RP23-143F10 for chr.7 at 130.1 Mb, RP23-470N5 for chr.7 at 73.1 Mb, RP23-247L11 for chr.7 at 135.0 Mb (OR gene cluster), RP23-136A15 for Rad23A, RP23-307P24 for chr.8 at 21.8 Mb and RP23-460F21 for chr.8 at 122.4 Mb. For a chromosome 7 centromere specific probe we used P1 clone 5279 (Genome Systems Inc.) that anneals to DNA segment D7Mit21. Random prime labeled probes were prepared using BioPrime Array CGH Genomic Labeling System (Invitrogen). Prior to labeling, DNA was digested with DpnII and purified with a DNA clean and concentrator-5 kit (Zymo research). Digested DNA (300 ng) was labeled with SpectrumGreen dUTP (Vysis) or Alexa fluor 594 dUTP (Molecular probes) and purified through a GFX PCR DNA and Gel Band Purification kit (Amersham Biosciences) to remove unincorporated nucleotides. Specificity of labeled probes was tested on metaphase spreads prepared from murine ES cells.

Cryo-FISH

Cryo-FISH was performed as described before[5]. Briefly, E14.5 liver and brain were fixed for 20 min in 4% paraformaldehyde/250 mM HEPES, pH 7.5 and cut into small tissue blocks, followed by another fixation step of 2 hrs in 8% paraformaldehyde at 4° C. Fixed tissue blocks were immersed in 2.3 M sucrose for 20 min at room temperature, mounted on a specimen holder and snap-frozen in liquid nitrogen. Tissue blocks were stored in liquid nitrogen until sectioning. Ultrathin cryosections of approximately 200 nm were cut using an Reichert Ultramicrotome E equipped with cryo-attachment (Leica). Using a loop filled with sucrose, sections were transferred to coverslips and stored at −20° C. For hybridization, sections were washed with PBS to remove sucrose, treated with 250 ng/ml RNase in 2×SSC for 1 hr at 37° C., incubated for 10 min in 0.1 M HCL, dehydrated in a series of ethanol and denatured for 8 min at 80° C. in 70% formamide/2×SSC, pH 7.5. Sections were again dehydrated directly prior to probe hybridization. 500 ng labeled probe was co-precipitated with 5 µg of mouse Cot1 DNA (Invitrogen) and dissolved in hybmix (50% formamide, 10% dextran sulfate, 2×SSC, 50 mM phosphate buffer, pH 7.5). Probes were denatured for 5 min at 95° C., reannealed for 30 min at 37° C. and hybridized for at least 40 hrs at 37° C. After posthybridization washes, nuclei were counterstained with 20 ng/ml DAPI (Sigma) in PBS/0.05% Tween-20 and mounted in Prolong Gold antifade reagent (Molecular Probes).

Images were collected with a Zeiss Axio Imager Z1 epifluorescence microscope (×100 plan apochromat, 1.4 oil objective), equipped with a CCD camera and Isis FISH Imaging System software (Metasystems). A minimum of 250 β-globin or Rad23A alleles was analyzed and scored as overlapping or non-overlapping with BACs located elsewhere in the genome, by a person not knowing the probe combination applied to the sections. Replicated goodness-of-fit tests (G-statistic)[6] were performed to assess significance of differences between values measured for 4C-positive versus 4C negative regions. Overview of the results is provided in Table 2.

Although we found statistically significant differences between background (0.4-3.9%) and true (5-20.4%) interaction frequencies, it may be clear that frequencies measured by cryo-FISH are lower than those measured by others using different. FISH protocols. Sectioning may separate some interacting loci and cryo-FISH measurements will therefore slightly underestimate true interaction frequencies. On the other hand, current 2D- and 3D FISH procedures will overestimate these percentages due to limited resolution in the z-direction. In the future, improved microscopy techniques in combination with more specific FISH probes will better reveal true interaction frequencies.

Example 2

The 3C procedure (i.e. formaldehyde fixation, (primary) restriction enzyme digestion, re-ligation of cross-linked DNA fragments and DNA purification) is carried out essentially as described (Splinter et al., (2004) *Methods Enzymol.* 375: 493-507), yielding a DNA mixture ('3C template') containing restriction fragments that are ligated because they were originally close in the nuclear space.

Inverse PCR is performed to amplify all fragments ligated to a given restriction fragment ('bait'; chosen because it contains a promoter, enhancer, insulator, matrix attachment region, origin of replication or any other first (target) nucleotide sequence).

For this, DNA circles are created by digesting the 3C template with a secondary restriction enzyme (preferably a frequent cutter recognizing tetra- or penta-nucleotide sequences), followed by ligation under dilute conditions such that intra-molecular interactions are favoured. To minimise a bias in circle formation due to topological constraints (Rippe et al, (2001) Trends in Biochem. Sciences 26, 733-40), a secondary restriction enzyme should be chosen that preferably cuts the bait at >350-400 bp from the primary restriction site. To increase inverse PCR amplification efficiency and reproducibility, circles are best linearised before PCR amplification by a restriction enzyme (eg. a 6 or more by cutter) that cuts the bait between the diagnostic primary and secondary restriction site.

Digestion of the 3C template with the secondary restriction enzyme, circularisation through ligation under diluted conditions and linearisation of bait-containing circles are performed under conditions standard for such DNA manipulations to yield a DNA template for inverse PCR amplification ('4C template').

Accordingly, 10 µg of 3C template is digested in 100 µl with 20 U of the secondary restriction enzyme (overnight), followed by heat-inactivation of the enzyme and DNA purification. Ligation is performed in 10 ml (1 ng/µl DNA) with 50 U T4 ligase (4 hrs at 16° C., 30 min at RT), followed by DNA purification. Finally, linearisation of the circles of interest is done in 100 µl with 20 U of restriction enzyme (overnight), followed again by DNA purification.

For inverse PCR, two bait-specific primers are designed, each as close as possible to the primary and directly neighbouring secondary restriction enzyme recognition site, respectively, and each with its 3'end facing outwards so that extension proceeds immediately across the restriction sites into a fragment ligated to the bait. Inverse PCR with these primers is preferably carried out on 100-400 ng DNA of 4C template (per 50 µl PCR reaction mix), to include a maximum number of ligation events per PCR reaction. We perform inverse PCR applying the Expand Long Template PCR System (Roche), using buffer 1 according to manufacturer's procedures.

The following PCR cycles are performed:
1. 2 min 94° C.
2. 15 sec 94° C.
3. 1 min 55° C.
4. 3 min 68° C.
5. repeat step 2-4 29× (or anything between 25-40×)
6. 7 min 68° C.
7. end Gel electrophoresis is performed to analyse reproducibility between individual PCR reactions. Typically, identical product patterns should be obtained.

In order to obtain sufficient material for labelling by random priming and array hybridisation, multiple PCR reactions (each obtained after 30 cycles of PCR) can be pooled, (instead of increasing the number of PCR cycles per reaction). As an alternative for random primed labelling, labelled nucleotides can be incorporated in the last cycles of PCR (e.g. 30 cycles (no label)+10 cycles (label)).

Example 3

Figure 8:
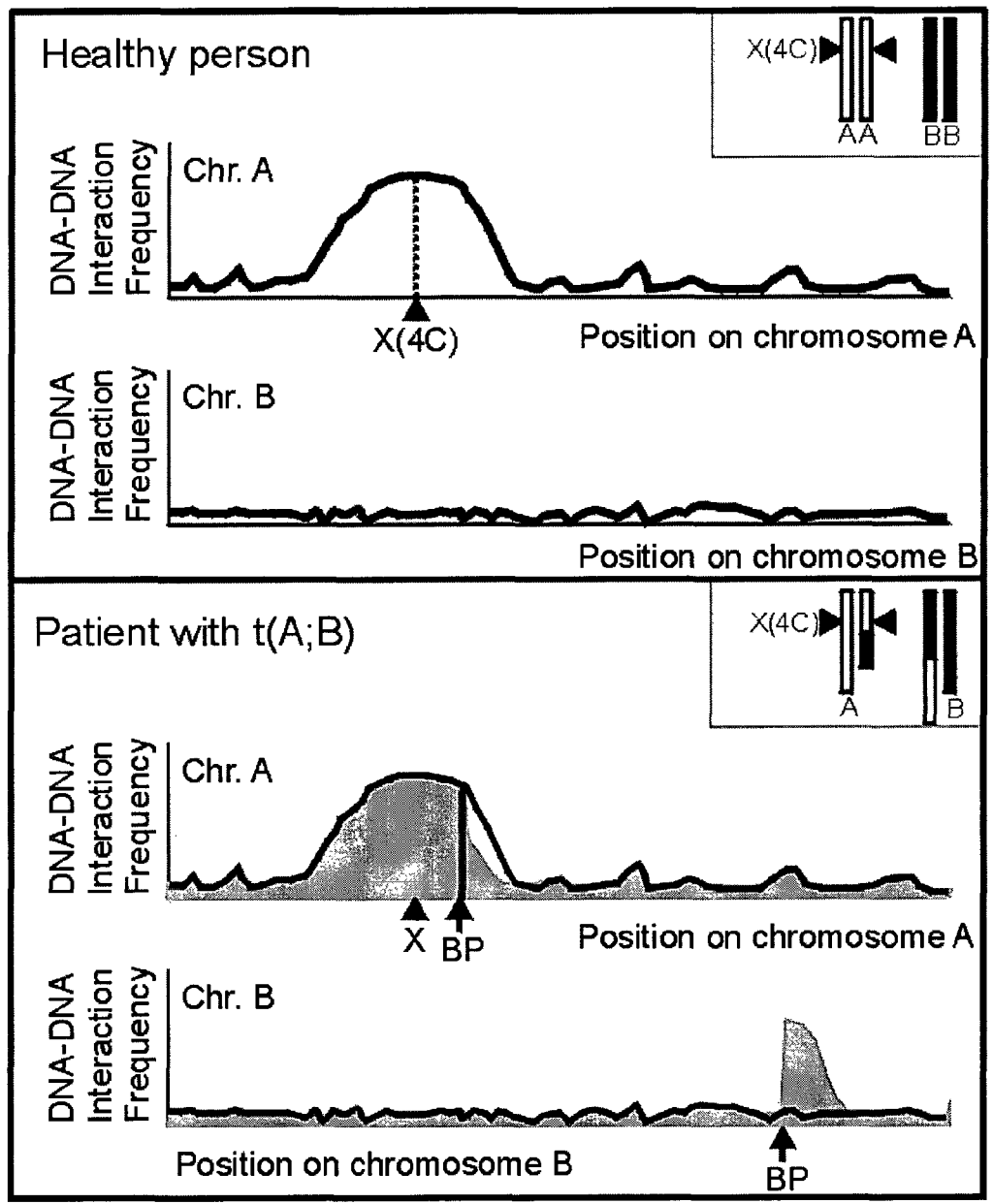
Figure 9:
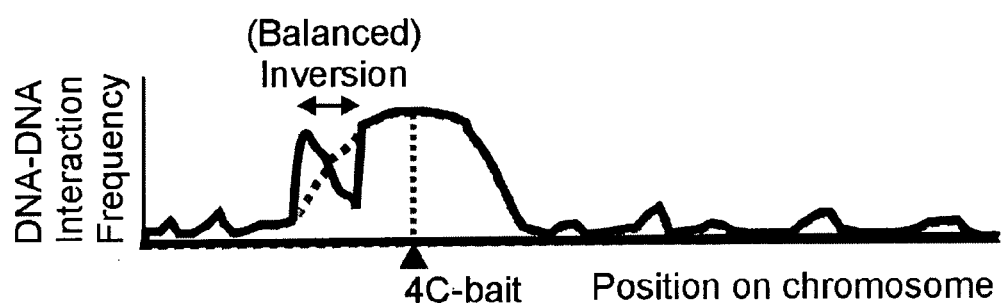
Figure 10:
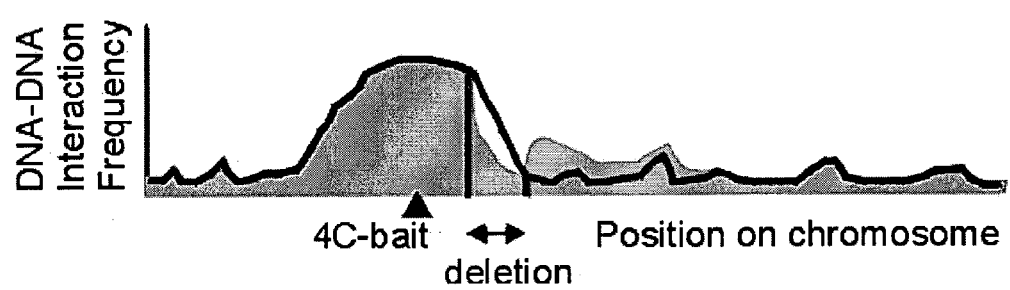
Figure 11:
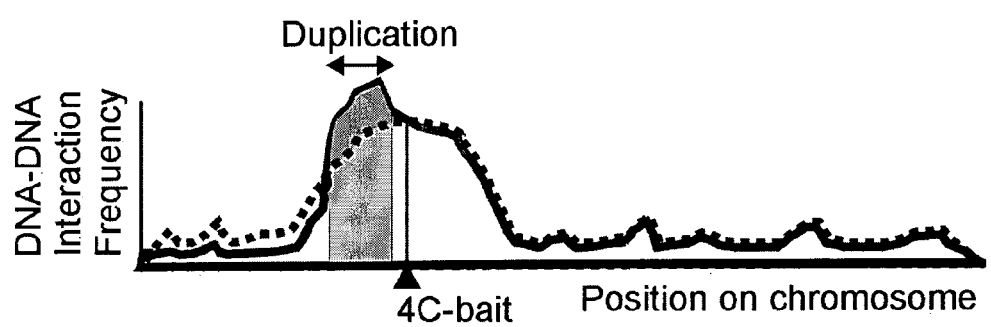

Detection of Translocation Using 4C Technology 4C technology is used to measure the interaction frequencies for a given sequence X present on a given chromosome A in cells from a healthy subject and in cells from a patient carrying a single, reciprocal, translocation between chromosome A and B with the breakpoint being close to sequence X (as shown in FIG. 8).

In normal cells this analysis reveals elevated hybridization signals (i.e. frequent interactions with X) for (almost) every probe located within 0.2-10 Mb of sequence X on chromosome A (the actual size of the chromosomal region showing strong cross-linking signals depends mostly on the complexity of the sample that was hybridized to the array). Elsewhere on the same chromosome A, as well as on other chromosomes, no such large region (on the linear DNA template) of probes with elevated hybridization signals is observed.

In patient cells however, hybridization signals with all chromosome A probes located on the other side of the breakpoint are reduced by ~50% (one copy of chromosome A is still intact and will produce normal signals), while a unique (i.e. not present in normal cells) concentration of elevated hybridization signals is observed for probes bordering the breakpoint on chromosome B. In fact, the abrupt transition between probes showing no versus strong hybridization signals on chromosome B reveals the location of the breakpoint on chromosome B.

Example 4

Figure 12:
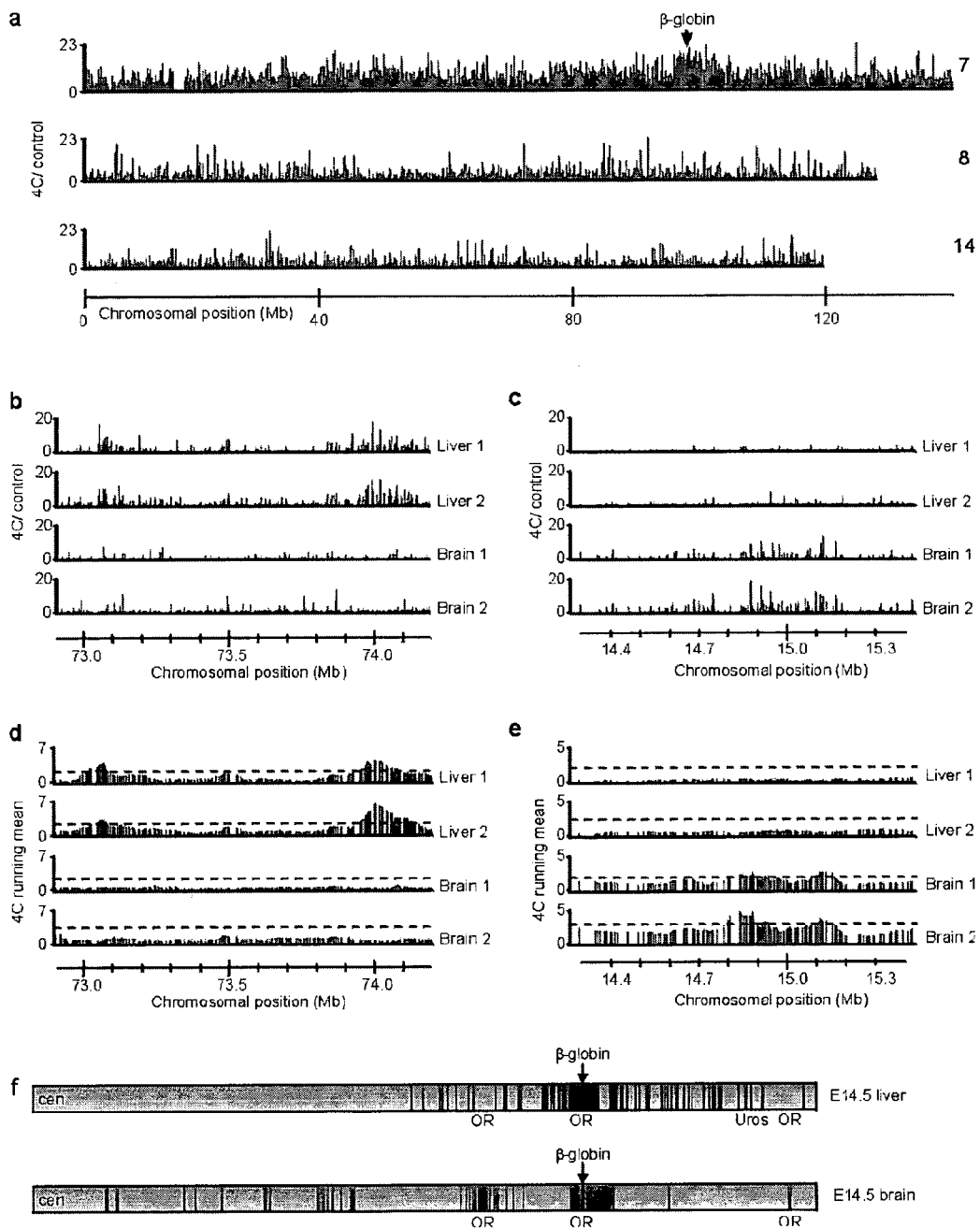
Figure 13:
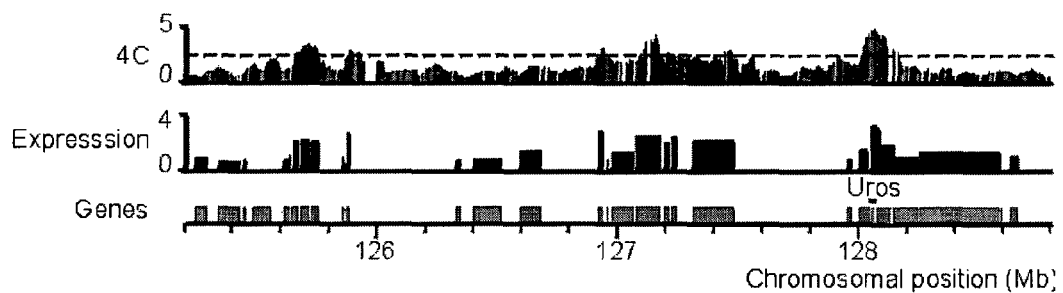
Figure 13:
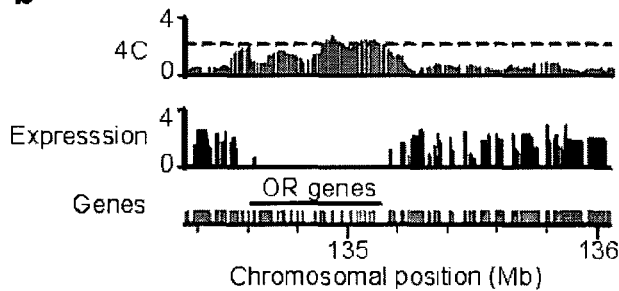
Figure 13:
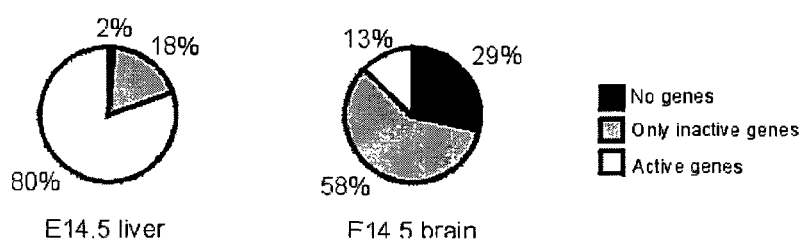

Analysis of 4C Technology Results 4C technology was used to characterise the genomic environment of the mouse β-globin locus control region (LCR), focusing on a restriction fragment containing its hypersensitive site 2 (HS2). The LCR is a strong erythroid-specific transcription regulatory element required for high levels of β-globin gene expression. The β-globin locus is present on chromosome 7 at position 97 Mb, where it resides in a large, 2.9 Mb, cluster of olfactory receptor genes that are transcribed only in olfactory neurons. Interactions were analysed in two tissues: E14.5 fetal liver, where the LCR is active and the β-globin genes are transcribed highly, and E14.5 fetal brain, where the LCR is inactive and the globin genes are silent. In both tissues, the great majority of interactions were found with sequences on chromosome 7 and very few LCR interactions were detected with six unrelated chromosomes (8, 10, 11, 12, 13, 14) (FIG. 12a). The strongest signals on chromosome 7 were found within a 5-10 Mb region centered around the chromosomal position of β-globin, in agreement with the idea that interaction frequencies are inversely proportional to the distance (in basepairs) between physically linked DNA sequences. It was not possible to interpret the interactions in this region quantitatively. We reasoned that these nearby sequences were together with β-globin so frequently that their large overrepresentation in our hybridisation samples saturated the corresponding probes. This was confirmed when we performed hybridisations with samples diluted 1:10 and 1:100 and found that signal intensity was reduced at probes outside and at the edge, but not inside this region (data not shown).

The 4C procedure yielded highly reproducible data. FIG. 2b-c shows unprocessed ratios of 4C-signals over control hybridisation signals for two 1.5 Mb regions on chromosome 7, roughly 25 Mb and 80 Mb away from the β-globin gene. At this level of resolution the results from independently processed samples were almost identical. Both in fetal liver and in brain, clusters of positive signals were identified on chromosome 7, often at chromosomal locations tens of megabases away from β-globin. These clusters typically consisted of minimally 20-50 probes with increased signal ratios juxtaposed on the chromosome template (FIG. 12b-c). Each probe on the array analyses an independent ligation event. Moreover, only two copies of the HS2 restriction fragment are present per cell, each of which can only ligate to one other restriction fragment. Therefore, the detection of independent ligation events with 20 or more neighbouring restriction fragments strongly indicates that the corresponding locus contacts the β-globin LCR in multiple cells.

To determine the statistical significance of these clusters, data of individual experiments were ordered on chromosomal maps and analysed using a running mean algorithm with a window size of approximately 60 kb. The running mean distribution of randomly shuffled data was used to set a threshold value, allowing a false discovery rate of 5%. This analysis identified 66 clusters in foetal liver and 45 in brain that reproducibly were found in duplicate experiments (FIG. 12d-f). Indeed, high resolution FISH confirmed that such clusters truly represent loci that interact frequently (see below).

Thus, 4C technology identifies long-range interacting loci by the detection of independent ligation events with multiple restriction fragments clustered at a chromosomal position.

Figure 16:
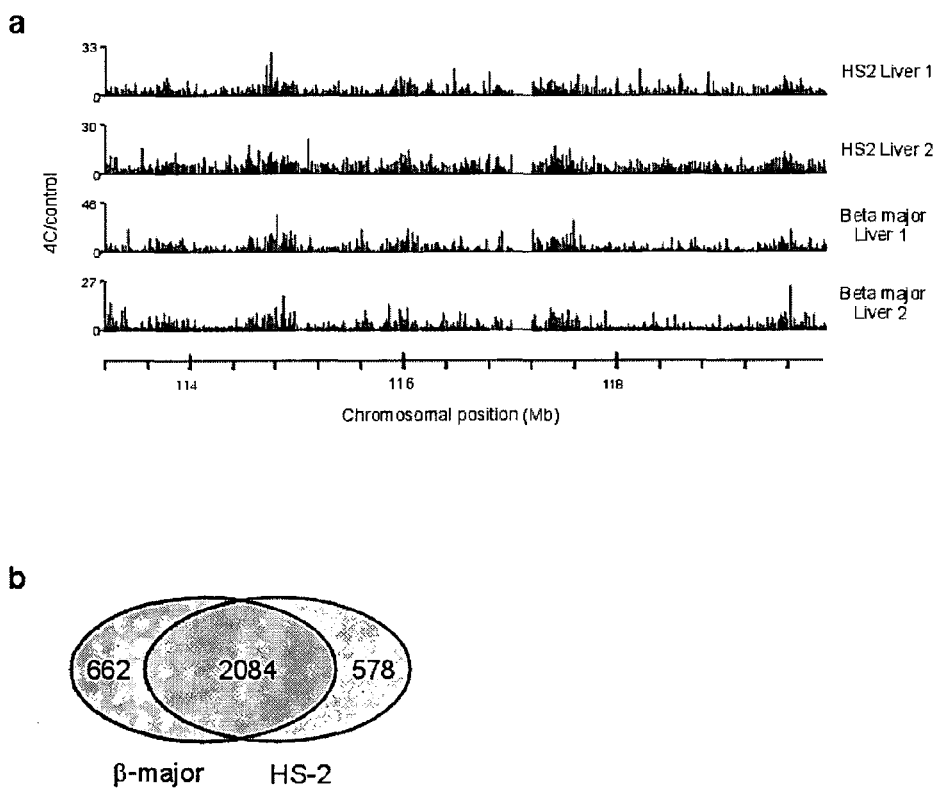

A completely independent series of 4C experiments was performed with a different inverse PCR primerset that investigated the genomic environment of the β major gene, located ~50 kb downstream of HS2. In foetal liver, the β major gene is highly transcribed and frequently contacted by the LCR. Almost identical clusters of long-range interactions with β major as with HS2 were found, both in foetal liver and in brain, further substantiating that these loci frequently contact the β-globin locus (FIG. 16).

Example 5

The Active and Inactive β-Globin Locus Occupy Distinct Genomic Environments

A comparison between the two tissues revealed that the actively transcribed β-globin locus in foetal liver interacts with a completely different set of loci than its transcriptionally silent counterpart in brain ($\tau=-0.03$; Spearman's Rank correlation) (FIG. 12f). This excluded that results were influenced by the sequence composition of the probes. In foetal liver, the interacting DNA segments were located within a 70 Mb region centred around the β-globin locus, with the majority (40/66) located towards the telomere of chromosome 7. In foetal brain, interacting loci were found at similar or even larger distances from β-globin compared to foetal liver and with the great majority of interactions (43/45) located towards the centromere of chromosome 7. These data demonstrated that the active and inactive β-globin locus contact different parts of chromosome 7.

Figure 17:
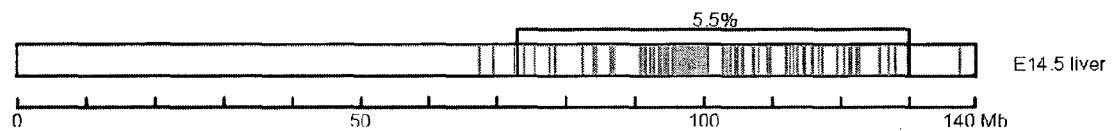

Six other chromosomes (8, 10, 11, 12, 13 and 14) were represented on the micro-arrays. Strong hybridisation signals on these chromosomes were rare, typically appeared isolated on the linear DNA template and often were absent from duplicate experiments. Also, running mean levels across these chromosomes never reproducibly came close to the levels scored for chromosome 7 (FIG. 17). Thus, our data showed that the β-globin locus mostly contacted loci elsewhere on the same chromosome, in agreement with the preferred location of this locus inside its own chromosome territory. We note that the α-globin locus was also present on the array (chromosome 11) and did not score positive for interaction with β-globin, in agreement with the recent demonstration by FISH that mouse α- and β-globin do not frequently meet in the nuclear space (Brown, J. M. et al. (2006) *J Cell Biol* 172, 177-87).

Figure 14:
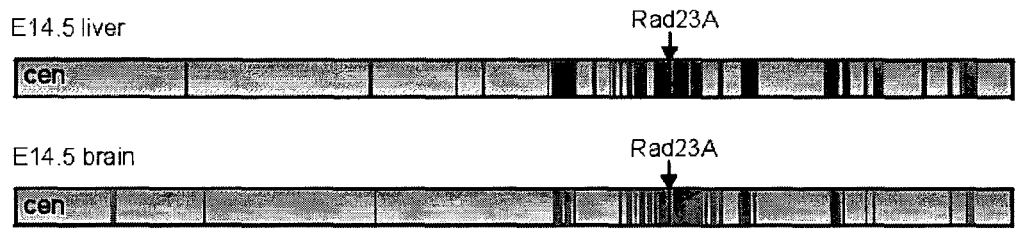
Figure 14:
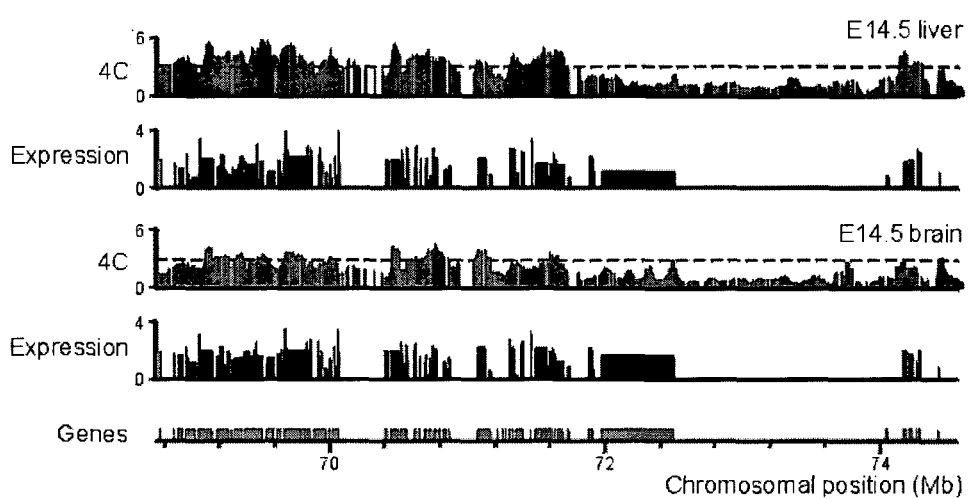
Figure 14:
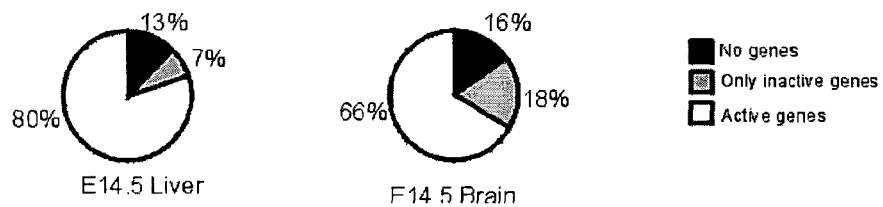
Figure 15:
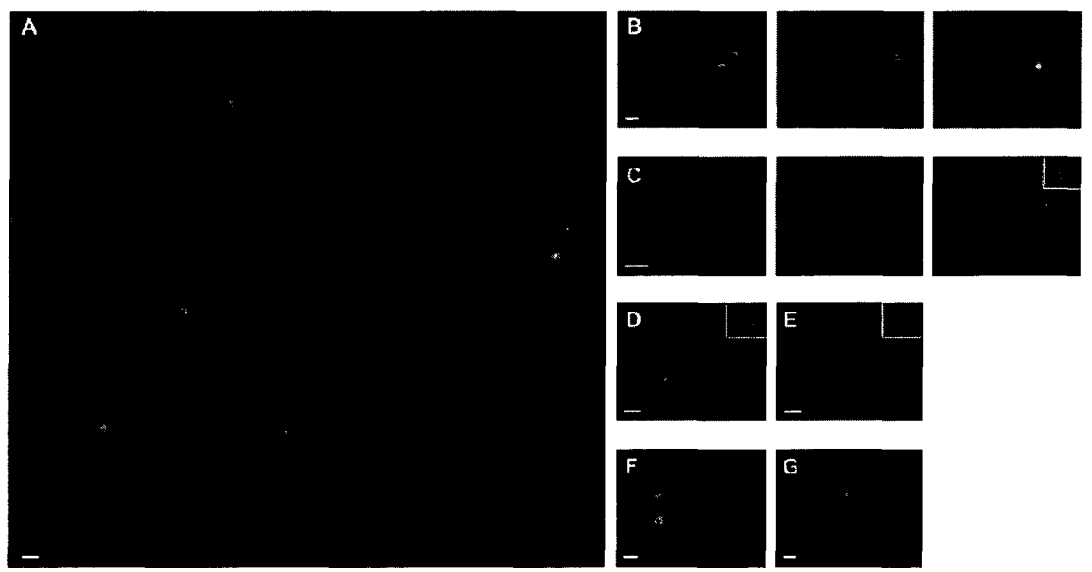
Figure 15:
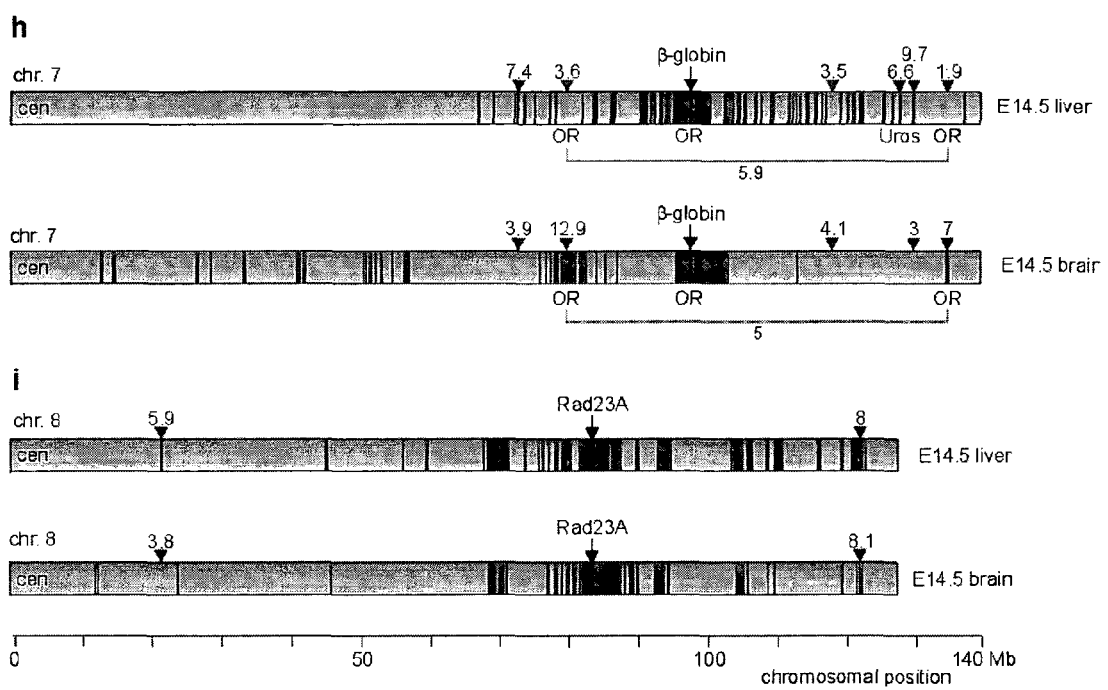

In order to better understand the relevance of the observed long-range interactions on chromosome 7, we compared the interacting loci to the chromosomal positions of genes. In addition, Affymetrix expression array analysis was performed to determine transcription activity at these positions in the two tissues. Although the average size of interacting areas in foetal liver and brain was comparable (183 kb and 159 kb, respectively), dramatic differences were observed in their gene content and activity. In foetal liver, 80% of the β-globin interacting loci contained one or more actively transcribed genes, while in foetal brain the great majority (87%) showed no detectable gene activity (FIG. 14). Thus, the β-globin locus is embedded in a very different genomic environment in the two tissues. In brain, where the locus is not active, it primarily contacts transcriptional silent loci located towards the centromere of chromosome 7. In foetal liver, where the locus is highly active, it interacts preferentially with actively transcribed regions located more prominently towards the telomeric side of chromosome 7. Importantly, 4C technology identified both Uros and Eraf, (~30 Mb away from β-globin) as genes interacting with the active β-globin locus in fetal liver, in agreement with previous observations made by FISH (Osborne, C. S. et al. (2004) *Nat Genet* 36, 1065-71 (2004)). Interestingly, in brain contacts were observed with the two other olfactory receptor gene clusters present on chromosome 7 that were located at each side of, and 17 and 37 Mb away from, β-globin.

Not all transcribed regions on chromosome 7 interact with the active β-globin locus in foetal liver. Therefore, we searched for a denominator shared exclusively by the interacting loci but not by other active regions in fetal liver. The β-globin genes, Uros and Eraf are all erythroid-specific genes that may be regulated by the same set of transcription factors, and it is an attractive idea that these factors co-ordinate the expression of their target genes in the nuclear space. We compared Affymetrix expression array data from E14.5 foetal liver with that of foetal brain to identify genes expressed preferentially (>5-fold more) in foetal liver. As such, 28% of the active genes on chromosome 7 were classified as "foetal liver-specific", of which 25% were found in a co-localising area. Thus, we found no enrichment of "foetal liver-specific" genes in the co-localising areas. More importantly, 49 out of 66 (74%) interacting regions did not contain a "foetal liver-specific" and it is therefore concluded that our data showed no evidence for co-ordinate expression of tissue-specific genes in the nuclear space. The β-globin genes are transcribed at exceptional high rates and it was next asked whether the locus preferentially interacted with other regions of high transcriptional activity, being either highly expressed genes or areas with a high density of active genes. Using Affymetrix counts as a measure for gene activity, we performed a running sum algorithm to measure overall transcriptional activity within 200 kb regions around actively transcribed genes. This analysis revealed that transcriptional activity around interacting genes was not higher than around non-interacting active genes on chromosome 7 (p=0.9867; Wilcoxon Rank sum).

Example 6

The Genomic Environment of a Housekeeping Gene is Largely Conserved Between the Tissues It was next investigated whether a gene that is expressed similarly in both tissues also switches its genomic environment. Rad23A is a ubiquitously expressed gene that resides in a gene-dense cluster of mostly housekeeping genes on chromosome 8. Both in E14.5 foetal liver and in brain, this gene and many of its direct neighbours are active. 4C analysis was performed and identified many long-range interactions with loci up to 70 Mb away from Rad23A. Importantly, interactions with Rad23A were highly correlated between foetal liver and brain ($\tau=0.73$; Spearman's Rank correlation) (FIG. 14a). A shared hallmark of these loci was again that they contained actively transcribed genes. Thus, in both tissues roughly 70% contained at least one active gene (FIG. 14b-c). Regions around interacting genes displayed statistically significant higher levels of gene activity compared to active genes elsewhere on the chromosome, as determined by a running sum algorithm (p<0.001 for both tissues). Thus, unlike the β-globin locus, the Rad23A gene that is located in a gene-rich region preferentially interacts over distance with other chromosomal regions of increased transcriptional activity. It was observed by FISH that the chromosomal area containing Rad23A resides mostly at the edge of (90%) or outside (10%) its chromosome territory (unpublished, D. Noordermeer, M. Branco, A. Pombo and W. de Laat). However, the 4C analysis only revealed intra-chromosomal interactions and no area on chromosome 7, 10, 11, 12, 13 or 14 reproducibly met our stringent criteria for interaction. Thus, Rad23A is mostly involved in intra-chromosomal interactions that are similar in two very different tissues. If Rad23A has preferred neighbouring loci on these unrelated chromosomes, they do not interact frequently enough to be detected under the conditions used here for 4C technology.

Example 7

Validation of 4C Technology by High-Resolution Microscopy

To validate the results obtained by 4C technology, cryo-FISH experiments were performed. Cryo-FISH is a recently developed microscopy technique, which has the advantage over current 3D-FISH protocols that it better preserves the nuclear ultra-structure while offering improved resolution in the z-axis by the preparation of ultra-thin cryo-sections (Branco, M. R. & Pombo, A (2006). PLoS Biol 4, e138). 4C data were verified by measuring how frequent β-globin or Rad23A alleles (always n>250) co-localised with more than 15 selected chromosomal regions in 200 nm ultra-thin sections prepared from E14.5 liver and brain. Importantly, all interaction frequencies measured by cryo-FISH were in perfect agreement with the 4C results (FIG. 16). For example, distant regions that were identified to interact with β-globin by 4C technology co-localised more frequently than intervening areas not detected by 4C (7.4% and 9.7%, versus 3.6% and 3.5%, respectively). Also, the two distant olfactory receptor gene clusters identified by 4C technology to interact with β-globin in foetal brain but not liver scored co-localisation frequencies respectively of 12.9% and 7% in brain, versus 3.6% and 1.9% in liver sections. In summary, co-localisation frequencies measured for loci positively identified by 4C technology were all significantly higher than frequencies measured for background loci ($p<0.05$; G-test). We concluded that 4C technology faithfully identified interacting DNA loci. Finally, we used cryo-FISH to demonstrate that loci identified to interact with β-globin also frequently contacted each other. This was true for two active regions separated over large chromosomal distance in foetal liver (FIG. 17) as well as for two inactive OR gene clusters far apart on the chromosome in brain (FIG. 16). Interestingly, frequent contacts between these two distant OR gene clusters were also found in foetal liver, where they did not interact with the OR gene cluster that contained the actively transcribed β-globin locus. These data indicated that nuclear interactions between distinct OR gene clusters were not a peculiarity of the foetal brain tissue analysed. It is tempting to speculate that such spatial contacts facilitate the communication between the many OR genes required to ensure that only a single allele is transcribed per olfactory neuron (Shykind, B. (2005) Hum Mol Genet 14 Spec No 1, R33-9.

Example 8

Nuclear Organisation of Active and Inactive Chromatin Domains

The observations described herein demonstrate that not only active, but also inactive genomic regions form distinct regions in the nuclear space that involve many long-range contacts, strongly suggesting that each DNA segment has its own preferred set of interactions. Our data suggest that when the β-globin locus is switched on, it leaves a transcriptional silent genomic environment and enters a nuclear area where interactions with active domains are favoured. It is anticipated that such a dramatic repositioning upon transcriptional activation may well be a hallmark only of tissue-specific genes that reach a certain expression level and, more importantly, lie isolated from other active genes on the linear chromosome template, as is the case for β-globin. It is proposed that the extensive network of long-range interactions that are identified both between inactive and between active genomic loci, reflects cell-to-cell differences in chromosome conformations more than being a consequence of dynamic movements during interphase (Chakalova et al. (2005) Nat Rev Genet 6, 669-77 (2005). Presumably, different degrees of de-condensation after cell division drive the active genomic regions away from inactive chromatin (Gilbert, N. et al. (2004) Cell 118, 555-66 (2004)) and contacts between distant loci of similar chromatin composition are stabilised mostly through affinities between chromatin-bound proteins. Spatial juxtaposition between distant loci may be functional, but may also simply be the consequence of the unfolding patterns of a chromosome. While individual loci can move within a restricted nuclear volume, the general conformation of a chromosome would largely be maintained throughout the cell cycle and requiring cell division for resetting. This idea is in agreement with life cell imaging studies showing restricted motion of tagged DNA loci in the nuclear interior (Chubb et al. (2002) Curr Biol 12, 439-45 (2002)) and fits well with studies showing that nuclear chromatin position information is frequently propagated during the cell division without being conserved in the population of cells (Essers, J. et al. Mol Biol Cell 16, 769-75 (2005); Gerlich, D. et al. Cell 112, 751-64 (2003)).

Example 9

Proof-of-Principle

4C Technology Accurately Detects Deletions in a Patient Sample (FIG. 19)

The presence of a deletion present in a leukaemia patient as revealed by 4C using a target nucleotide sequence that is either at 2 Mb (A) or at 1.3 Mb (B) upstream ('to the left') from the first breakpoint. Note that deletions cause a reduction of DNA interaction signals at the deleted region, but also cause an increase in DNA:DNA interaction frequencies for sequences directly downstream ('at the right') of the last breakpoint. This is particularly obvious when interactions with target nucleotide sequence B are closely examined (see bottom two graphs). Based on 4C data primers were designed on each side of the deleted region and breakpoint was identified by sequencing: plain text is sequence upstream of deletion, in bold indicated is an inserted nucleotide, underlined is the sequence downstream of the deletion.

Example 10

Proof-of-Principle

4C Technology Accurately Detects a Balanced Translocation in a Patient Sample (FIG. 25)

Proof of principle for the detection of balanced translocations. Detection of t(1;7) translocation as described in (R. Burnett et al., Blood, Vol 84, No 4 (Aug. 15, 1994: pp 1232-1236). Target nucleotide sequences flank the TCRb locus on chromosome 7, with the red signals representing DNA:DNA interactions with the target sequence that is located upstream of the TCRb locus, and the blue signals representing DNA:DNA interactions with the target sequence that is located downstream of the TCRb locus. Depicted are the interacting DNA signals found on chromosome 1. Top panel shows the theoretical signal distribution. The middle and lower panel show the actual signal distribution. The bottom panel shows signals at a resolution of individual probes juxtaposed on the chromosome template. Note that in case of a balanced translocation target nucleotide sequences flanking the breakpoint will show a mutually exclusive set of interchromosomal DNA interaction signals that directly border each other on the linear chromosome template of the translocating partner chromosome. Position of sequenced breakpoint (described in Burnett et al., 1994) is indicated by an arrow at the bottom panel.

Example 11

Proof-of-Principle

4C Technology Accurately Detects an Unbalanced Translocation in a Patient Sample (FIG. 27)

Detection of unbalanced translocations. Detection of t(4;7) translocation as described in (R J Galjaard et al., Am J Med Genet A. 2003 Aug. 30;121(2):168-73). Target nucleotide sequences locate to chromosome 7; the depicted interacting DNA signals are located on chromosome 4. Two target sequences were used located upstream (5') and downstream (3') of the breakpoint on chromosome 7. Interacting DNA signals located on chromosome 4 are indicated (for both target sequences in blue). The region in between the clusters of interacting DNA fragments on chromosome 4 has been deleted in this patient. Top: signals for the complete chromosome 4. Bottom panel 4C data: signals at a 11.5 MB region around the breakpoints on chromsome 4. Based on these 4C data, the HindIII restriction fragment on chromosome 4 containing the translocation breakpoint was identified and used to map the breakpoint by sequencing.

The sequence is provided at the bottom of the figure, where underlined sequence is from chromosome 4, bold is found both on 7 and 4 and plain sequence is from chromosome 7.

Example 12

Rapid High-Resolution Identification of Balanced Genomic Rearrangements by 4C Technology Summary Current techniques to study genetic variation fail, or do not accurately identify balanced chromosomal rearrangements (inversions, translocations) that frequently occur in the human population and can cause disease. Here we demonstrate that 4C technology detects balanced inversions and translocations, as well as unbalanced translocations and deletions, at a resolution (~7 kilobases) allowing immediate sequencing of the breakpoints. 4C technology is used to characterize rearrangements underlying congenital abnormalities and leukaemia. The LMO3 gene is identified as a novel translocation partner of the T cell receptor β gene (TCRB) in T cell acute lymphoblastic leukemia (T-ALL). These results establish 4C technology as a powerful new clinical research tool for the accurate analysis of genomic rearrangements, important for diagnosis of disease, prognosis of and, ultimately, optimal patient care.

Introduction

Chromosomal rearrangements (deletions, amplifications, inversions, translocations) can be the cause of disease, particularly when they affect gene expression due to gain or loss of genes, creation of fusion-genes, or repositioning of transcription regulatory DNA elements. Rearrangements arising in the germline can give rise to congenital defects, those in somatic tissue can result in neoplasia. Following the completion of the human genome sequencing projects, it has now become a major task to characterize structural variants in the human genome, as it is becoming increasingly clear that genomic diversity occurs naturally in the human population and can be linked with susceptibility to disease (1-6).

Microarray-based comparative genomic hybridization (array-CGH) is a widely used high-throughput genomics approach that can detect chromosomal amplifications or deletions at a resolution of a few kilobases or even less. CGH relies on the measurement of changes in DNA copy number such as seen in deletions or amplifications and therefore fails to identify translocations and inversions that occur without loss or gain of DNA content. It is unknown how frequently such balanced events occur but they are estimated to constitute up to 20% of all structural variations (7). At present their detection largely depends on cytogenetic approaches such as chromosomal karyotyping, which have the disadvantage that they miss events (approx. 20%) and provide limited resolution (maximum 5-10 megabases). This necessitates further, labour-intensive, analysis to identify the actual genetic aberration underlying the disease. Here, we demonstrate that Chromatin Conformation Capture on Chip (4C) technology (8) identifies both balanced and unbalanced genomic rearrangements at a resolution (~7 kb, see below) that allows immediate cloning and sequencing of the chromosomal breakpoints. Importantly, this high-resolution strategy requires the use of a single microarray to screen the entire genome and therefore is cost-effective.

Our initial results with 4C showed that no matter the folding of the chromatin and the long-range interactions of a given locus, DNA fragments close on the linear chromosome template are always captured most efficiently, resulting in strong and often even saturated hybridization signals for probes within a region of at least 5-10 megabases surrounding the target sequence. This is in agreement with the idea that the DNA segments located closer on a flexible chromatin fiber will interact more frequently (9). Local fragments are also captured much more efficiently than segments megabases away that frequently loop towards the target sequence (8). Random capturing of restriction fragments is rare, as demonstrated by the very low frequency of signals from probes located on unrelated chromosomes. Thus, 4C technology allows reconstructing physical maps of chromosome templates around target sequences and hence it should also be capable of identifying changes in these maps as the result of genomic rearrangements.

Materials & Methods

Sample Preparation

T-ALL patient samples and healthy control T-cell samples were handled as described previously (Vlierberghe et al., *Leukemia* 20, 1245 (July 2006); Simonis et al., *Nat Genet* 38, 1348 (November 2006)). The EBV-transformed cell line derived from the PAP patient was cultured and handled as described before (Simonis et al., *Nat Genet* 38, 1348 (November 2006); Galjaard et al., *Am J Med Genet A* 121, 168 (Aug. 30, 2003).

4C Array Design

The 60 bp probes were designed within 100 bp from a HindIII site, using criteria described previously that for example select only unique DNA sequences (Simonis et al., *Nat Genet* 38, 1348 (November 2006)). To be able to cover the entire genome with the 400.000 probes that fit on the nimblegen microarray, a selection was made. Probe numbers were first reduced by keeping only one probe per HindIII fragment, instead of one on each side. Secondly, probes were selected such that the spacing of probes was as equal as possible across the genome.

4C Analysis 4C analysis was performed as described previously (2), using the following primer sequences:

```
                                          (SEQ ID NO: 7)
5'-end of TCRB CATGAAGAAACGAGCACCC CCTTGA
TGTTTCTCCCTTTACC (SEQ ID NO: 8)
3'-end of TCRB TGTCAGGCTCTTCTCCTACAC GTCG
TCCAGAACACTCACC (SEQ ID NO: 9)
Centromeric t(4; 7) AATCCAGGGCTACTTCCAG CCGTGATGCT
ATCTGCCA (SEQ ID NO: 10)
Telomeric t(4; 7) TGTTGGAAGACCAGGTGAAG TGTCGTGGAAA
GCGAGTG (SEQ ID NO: 11)
Deletion 9 CAATCCCAGATACATTCCTCATACAAATACTTTCCAAGA
CTGGAC (SEQ ID NO: 12)
3' of TCRA GAATATGTTATGCTTGATCC TTCCAT
GAGAGAAGTCTAG
```

4C data was visualized using SignalMap software. To create whole chromosome view pictures of the 4C data, a running mean with a window size of 29 probes was calculated using the R package (www.r-project.org).

Restriction-Fragment-Paired-End-Sequencing

10 μg of genomic DNA was first digested in 500 μl with 10 U of an enzyme that recognizes 6 bases (HindIII, BgIII or EcoRI) (37° C. for 2 hours). Samples were purified by phenol-chloroform extraction and ethanol precipitation. Subsequently, samples were ligated in 2 ml with 40 U of ligase (Roche) for 4 hours at 16° C. and 30 minutes at 20° C.

Ligated samples were purified by phenol-chloroform extraction and ethanol precipitation.

A second digestion was performed with a restriction enzyme that recognizes 4-bases (e.g. NlaIII or DpnII) under the same conditions as described for the 6-base recognizing enzyme. Subsequent ligation was also as described above. Samples were purified by phenol-chloroform extraction and ethanol precipitation. Selected fragments were PCR amplified from 50-100 ng of DNA, using the following conditions: 94° C. for 3 minutes, followed by 30 cycles of 15 seconds at 94° C., 1 minute at 55° C. and 2 minutes at 72° C. and one final step of 7 minutes at 72° C.

Results

Identifying Translocation Breakpoints

Figure 33:
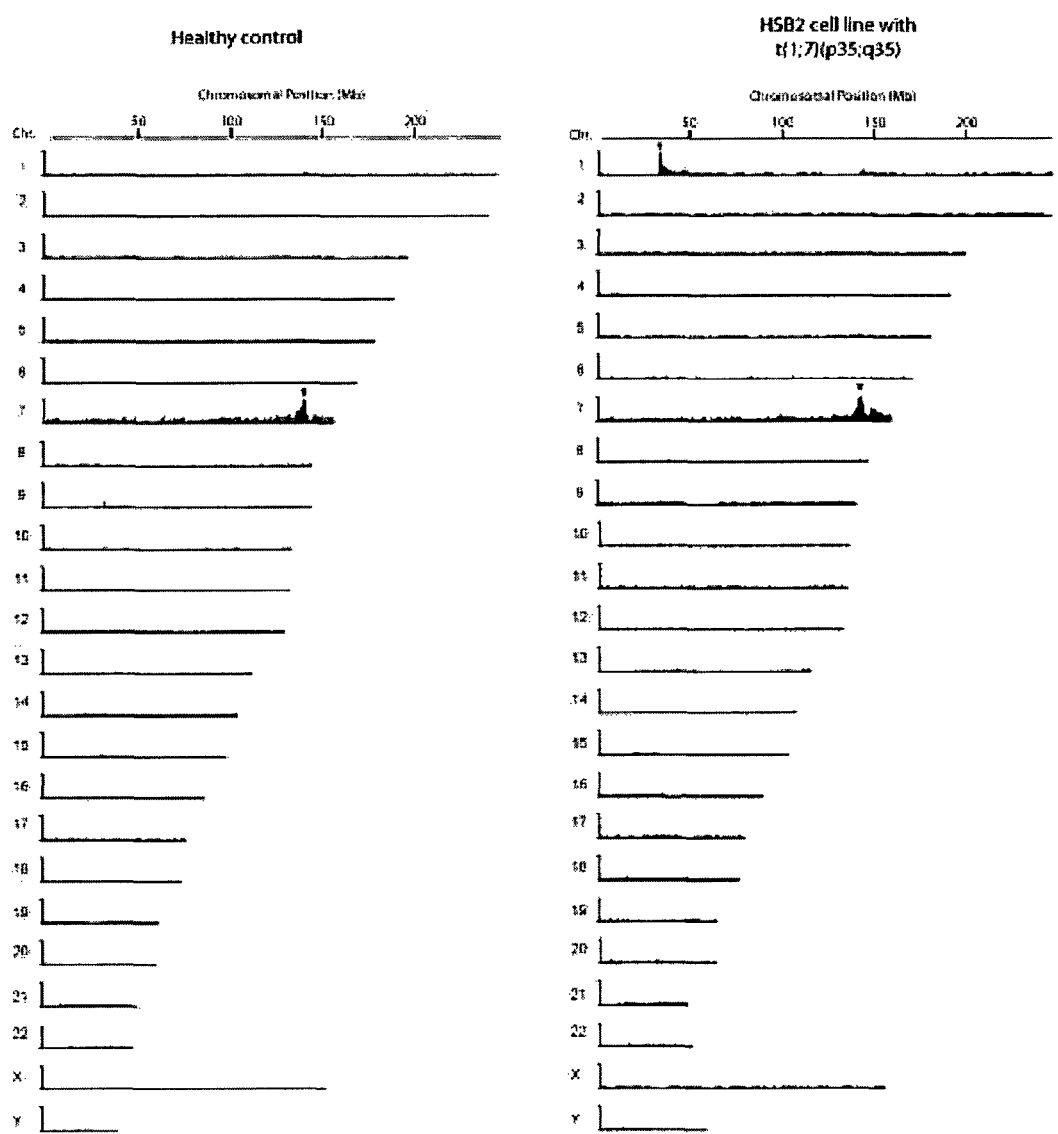

To test this, 4C technology was first applied to the HSB-2 T-ALL cell line, containing a reciprocal translocation t(1;7) (p35;q35) between the T cell receptorβ (TCRB) locus on 7q35 and the LCK locus on 1p35 (10). Two independent 4C experiments were performed, each analyzing interactions with a different restriction fragment on chromosome 7 located on either side of the breakpoint in the TCRB locus and at a distance of 462 kb and 239 kb, respectively. In both cases, strong hybridization signals around the TCRB locus on chromosome 7 were observed in a healthy control sample and the HSB-2 sample. The control sample showed no, or background, signals on all other chromosomes (FIG. 30A; FIG. 33). In contrast, the HSB-2 sample showed additional very high signals specifically across a megabase region on 1p35 (FIG. 30B). These signals represented restriction fragments on chromosome 1 captured by the two fragments on chromosome 7 in HSB-2, indicating that parts of these chromosomes were brought in close physical proximity. The most telomeric TCRB target sequence on chromosome 7 captured restriction fragments towards the centromeric side of the LCK gene on chromosome 1. Conversely, the most centromeric TCRB target sequence captured fragments towards the telomeric side of LCK. This is in agreement with the orientation of the t(1;7) translocation. Moreover, the first restriction fragments captured on chromosome 1 in both experiments directly flank the previously identified chromosomal breakpoint. Thus, 4C locates translocation breakpoints to a position in between the pair of probes that represents the transition from non-captured to captured restriction fragments. In this case, the two 4C experiments analyzing interactions with chromosome 7 target sequences each identify the breakpoint on chromosome 1 involved in the balanced t(1;7) translocation within 27 kb.

Identifying Inversions

Figure 34:
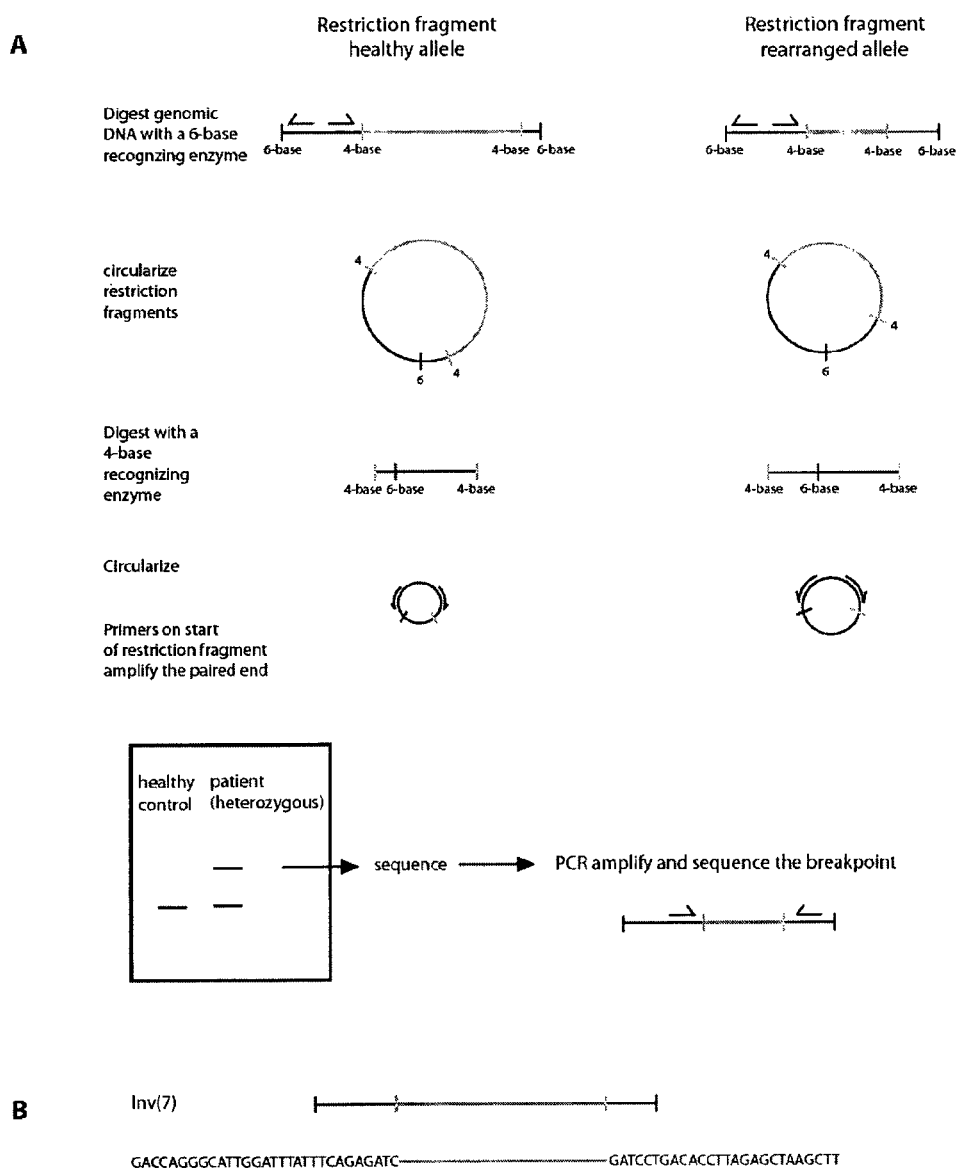

Next, we tested if 4C can also identify inversions. We applied 4C technology to a pedriatic T-ALL patient sample that, based on FISH and microarray expression studies, was suspected to carry an inversion on chromosome 7, inv(7) (p15q35). This abnormality leads to the rearrangement of the TCRB locus into the HOXA gene cluster, as was previously described for other patients (11, 12). Again two experiments were performed, using the same set of TCRB target fragments that identified the t(1;7) translocation described above. The two target sequences efficiently captured many fragments covering megabases of DNA on the other side of chromosome 7 around the HOXA locus in the 4 patient sample only (FIG. 30C-D). Moreover, each target sequence captured a distinct chromosomal region around the HOXA gene cluster, indicating that the two fragments are linked to different parts of chromosome 7. The most 3' TCRB target fragment captured the most 3' HOXA fragments, while the most 5' TCRB target fragment captured the most 5' HOXA fragments, thus revealing an inversion between the loci. The two captured regions around HOXA directly flank each other, showing that the inversion was balanced and not accompanied by (extensive) loss of HOXA sequences. The two probes that mark the transition between non-captured and captured fragments revealed the position of the breakpoint, which located to a 6 kb region near the HOXA9 gene of the HOXA cluster (FIG. 30D). Confirmation that this region indeed carries the breakpoint was obtained by sequencing, using a restriction-fragment-paired-end sequencing approach (FIG. 34). We therefore conclude that 4C technology is the first high-throughput genomics approach that can detect balanced translocations and inversions. The resolution provided by 4C technology allows immediate cloning of the breakpoints. 4C technology is therefore the first technique that can detect balanced genetic events at such high resolution.

Identification of Unbalanced Translocations

Figure 31:
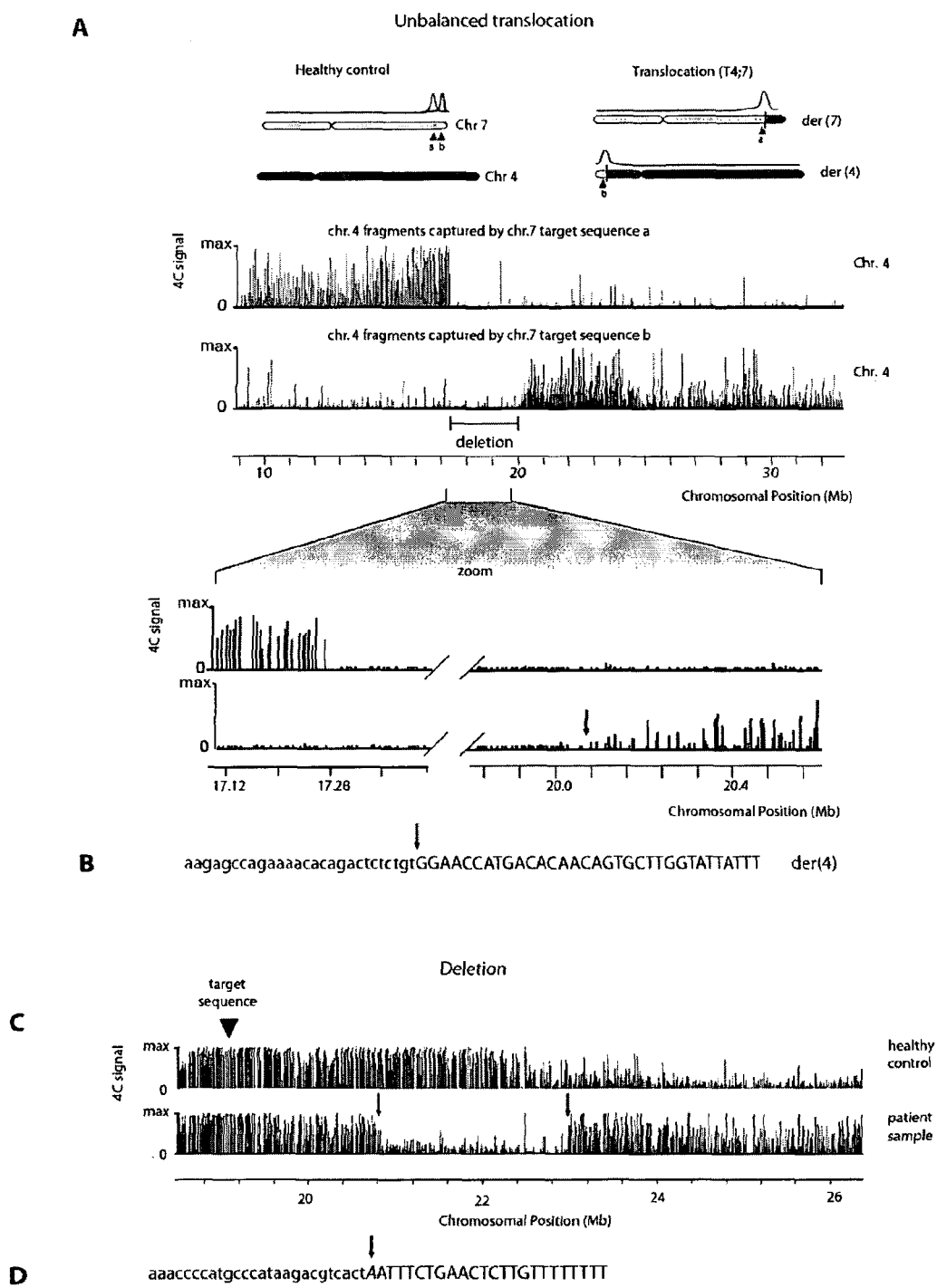
Figure 35:
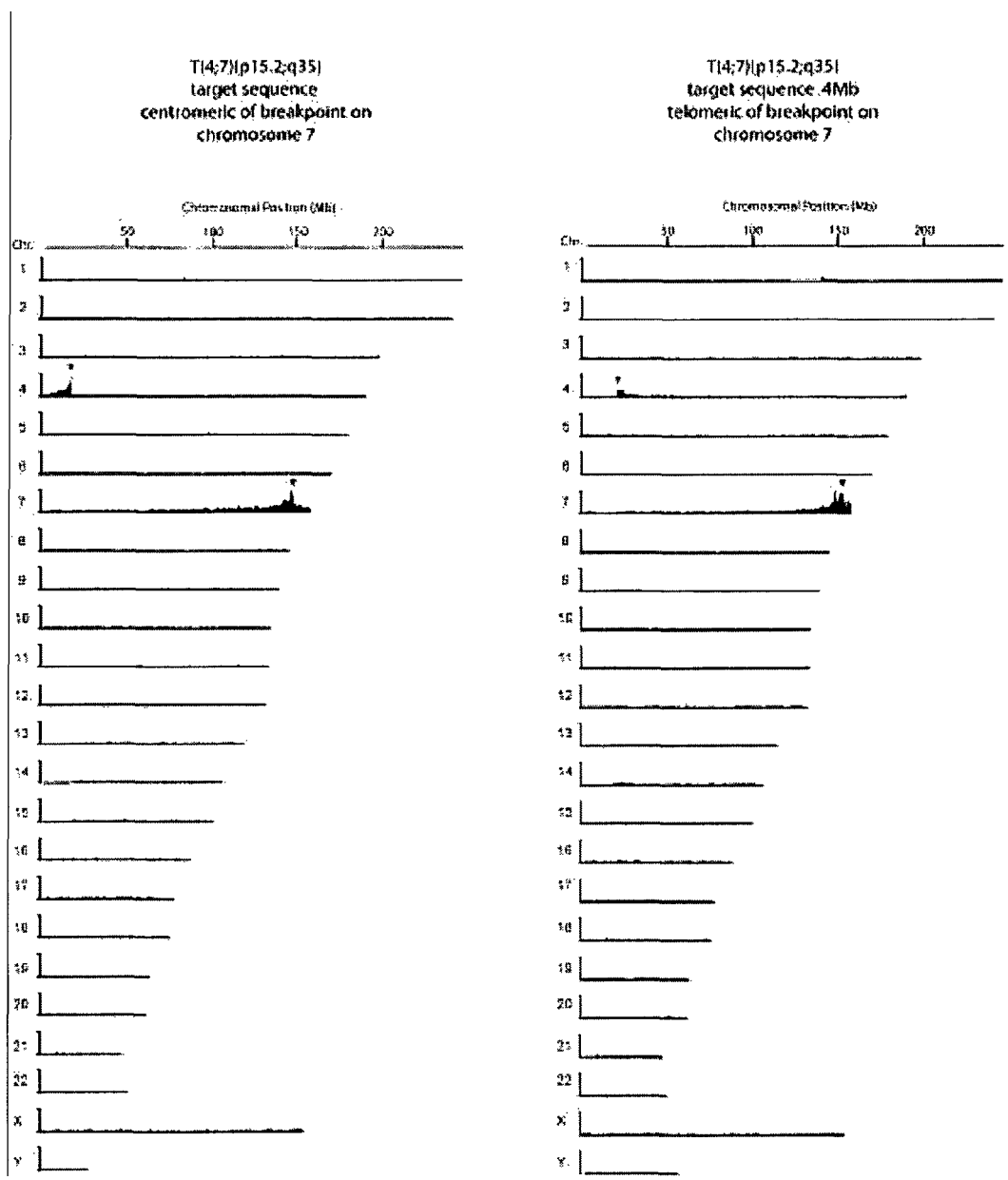

The potential of 4C technology was further explored by applying it to an EBV transformed cell line derived from a patient with Postaxial Polydactyly (PAP). PAP is an autosomal dominant heritable disorder characterized by extra ulnar of fibular digits. The patient cells were previously characterized by karyotyping and FISH to contain an unbalanced translocation between chromosomes 4 and 7 with a microdeletion, t(4;7)(p15.2;q35). However, the limited resolution of FISH precluded defining the extent of the deletion and the exact positions of the breakpoints (13). Two 4C experiments were performed, each analyzing DNA interactions with a target fragment located on another side of the rearranged part of chromosome 7, one of which being 4 megabases away from the nearest breakpoint (see below). In both experiments, genomic fragments were captured not only on chromosome 7 but also on chromosome 4, at 4p15.2 (FIG. 31A; FIG. 35). In contrast to what was found for the balanced translocation, the chromosome 4 fragments captured by the two target sequences did not directly neighbor each other. One breakpoint was located at position 17.28 Mb (NCBI 36) and the other was found at position 20.08 Mb of chromosome 4, showing that the t(4;7) translocation was accompanied by a 2.8 Mb deletion on chromosome 4. To verify that the transitions from captured to non-captured restriction fragments indeed mark the positions of the breakpoints, the breakpoint that was least obvious from the 4C data, located at 20.08 Mb, was cloned and sequenced (FIG. 31B). This confirmed the position of the breakpoint on chromosome 4 at 20.08 Mb inside the gene SLIT2 and revealed that it was rearranged with an intergenic sequence on chromosome 7 that was 4 Mb away from the target sequence used to identify the breakpoint. This shows that 4C target sequences can capture DNA fragments and identify rearrangements even when the breakpoints are several megabases away. When 4C analysis is directed to both sides of a genomic breakpoint, it can immediately identify whether a translocation or inversion is balanced or is accompanied by additional rearrangements such as a deletion (i.e. unbalanced).

Identification of Deletions

We next investigated whether 4C technology can identify a deletion that is not associated with a translocation. For this, we analyzed another pedriatric T-ALL patient sample that, based upon array-CGH data, contained a homozygous deletion of the p15/p16 loci on 5 chromosome 9p21. The exact size of the deletion and the actual breakpoints were not known. We defined a target fragment located ~2 Mb away from one of the estimated breakpoints. As expected, a region lacking probe signals was observed, demarcating the deleted area (FIG. 31C). An increase in hybridization signals for the region immediately downstream of the deletion is observed in the patient sample versus the healthy control sample. This is because the region is in closer proximity on the linear template to the target fragment due to the deletion. Based on the 4C data, PCR primers flanking the ~2 Mb deleted region were designed that allowed amplification across the breakpoints; sequencing of the PCR products confirmed the positions of the two breakpoints flanking the deletion (FIG. 31D). We conclude that 4C technology can identify homozygous deletions. Deletions reveal themselves as regions containing reduced hybridization signals in combination with more downstream sequences that show increased hybridization signals.

Figure 32:
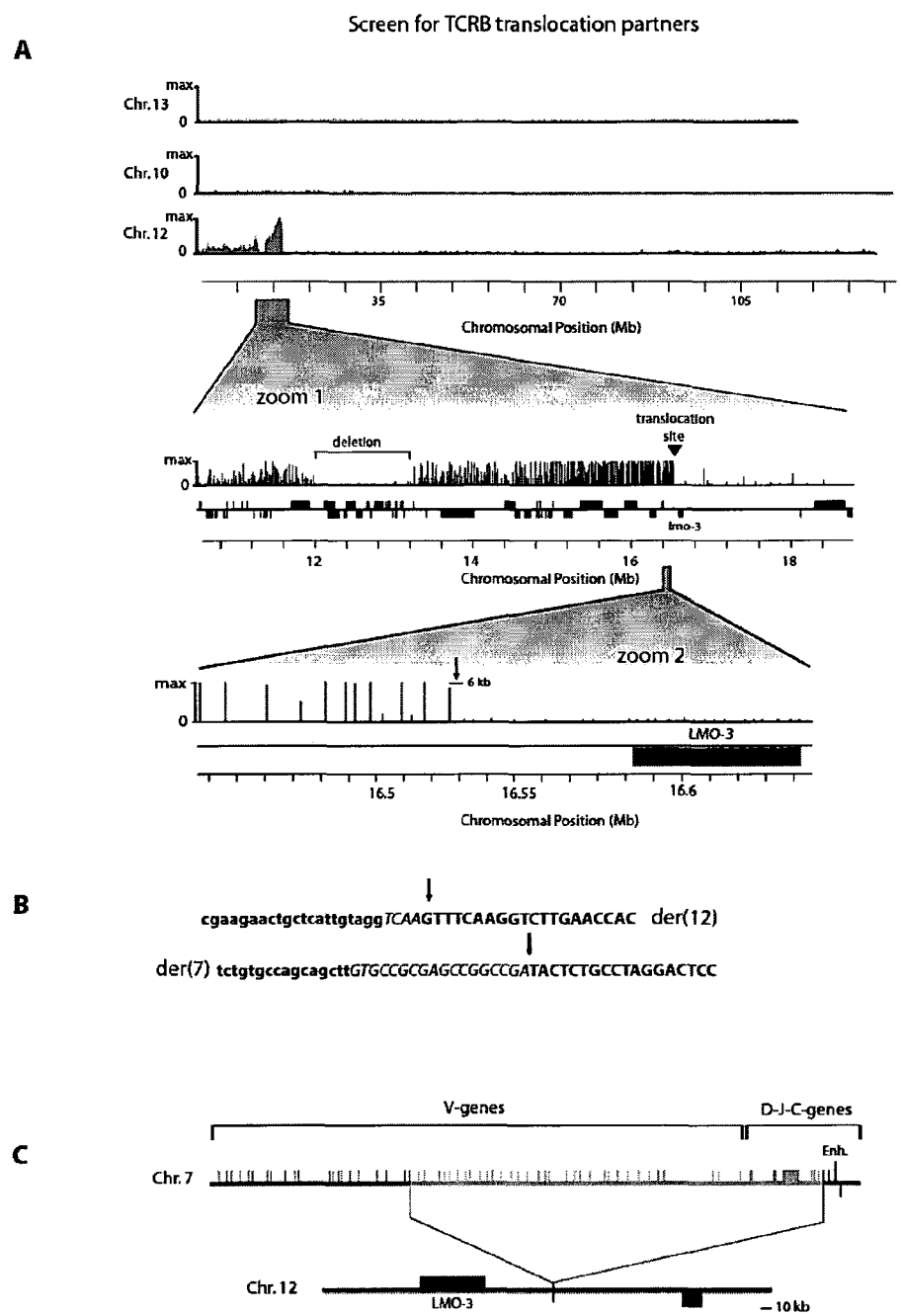
Figure 36:
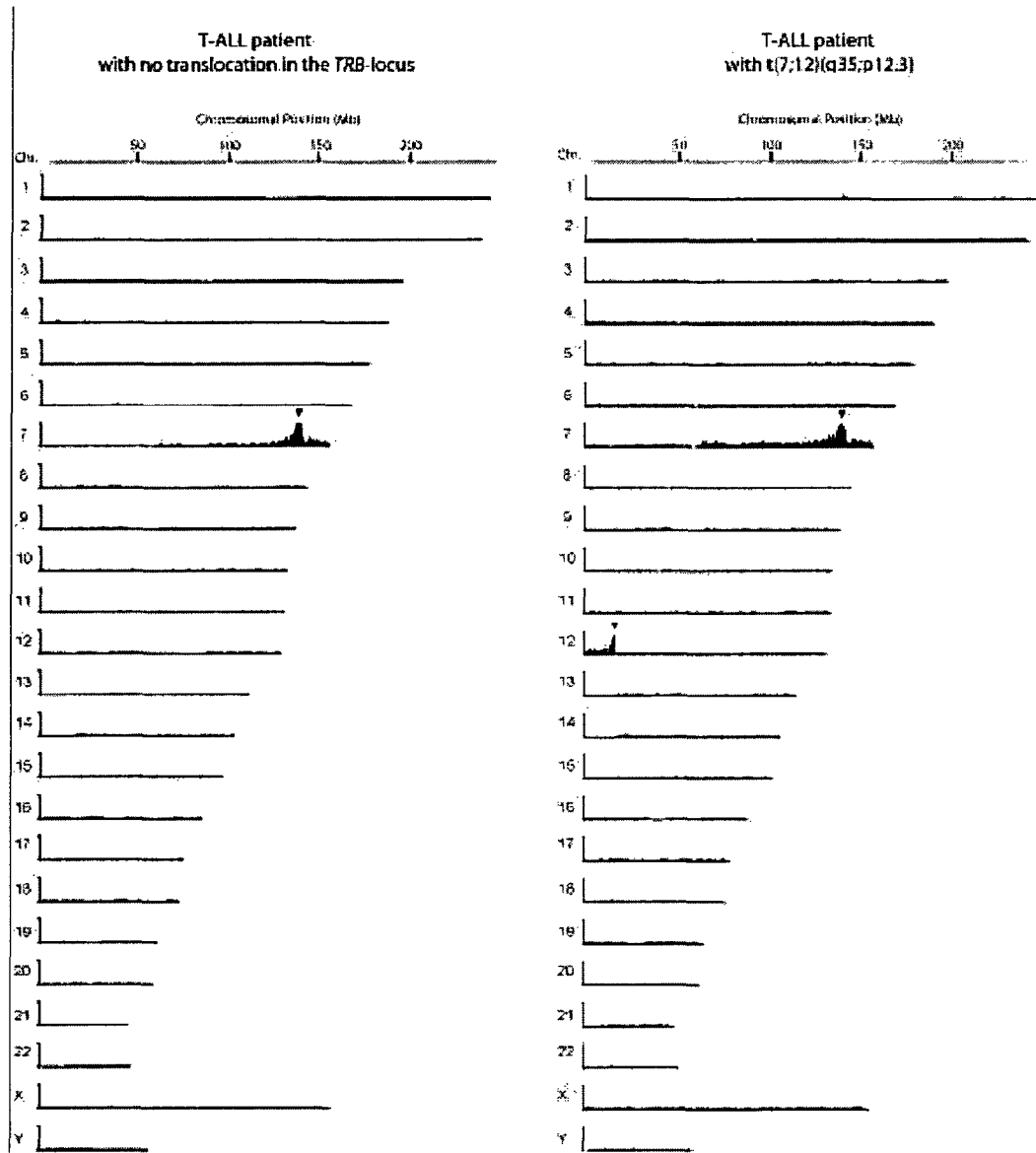
Figure 37:
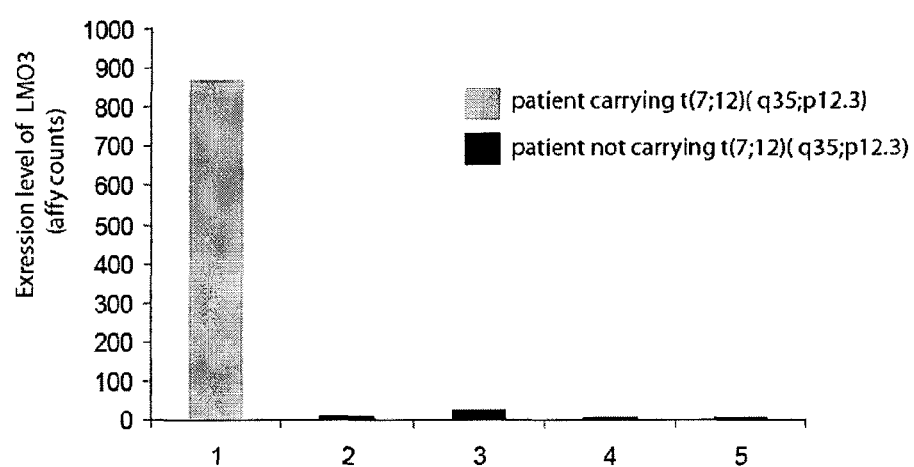

Uncharacterized Patient Samples 4C technology was applied to the screening of uncharacterized T-ALL patient samples for genetic rearrangements associated with the TCRB locus or the T-cell Receptor α (TCRA) locus. In T-ALL, chromosomal translocations frequently occur during attempted VDJ recombination of the TCR loci. Samples from five T-ALL patients, which were previously shown not to carry any of the recurrent genetic abnormalities associated with T-ALL (data not shown), were analyzed by 4C technology, using a target sequence near TCRB and one near TCRA. None of the samples showed rearrangements with the TCRA locus (data not shown), and four out of five patient samples also showed no rearrangement with TCRB (FIG. 36), which was subsequently confirmed by FISH. One patient sample however, showed a translocation between TCRB and the p arm of chromosome 12 (FIG. 32A; FIG. 36). In addition, the patient was found to carry a large deletion on chromosome 12, which was confirmed by an oligo-arrayCGH experiment (data not shown). This deletion is located ~3 Mb away from the translocation breakpoint, again showing that 4C target sequences can identify rearrangements over large distances. The translocation t(7;12) (q35;p12.3) has not been described before in T-ALL. The two probes on chromosome 12 that mark the transition between captured and non-captured restriction fragments were 6 kb apart and located just downstream of the Lim-domainonly gene LMO3. Restriction-fragment-paired-end-sequencing was used to confirm that these probes demarcate the region containing the breakpoint. Sequencing of the breakpoints present on both derivative chromosomes demonstrated that chromosome 12 was rearranged without the loss of a single nucleotide, while the break in chromosome 7 was accompanied by a deletion of almost 400 kb of TCRB sequences (FIG. 32B). This deletion was possibly due to deletion events associated with attempted VDJ recombination of the TCRB locus. Both breakpoints also contained intervening basepairs of unknown origin (4 and 18 bp, respectively), which may represent the random nucleotides that are normally also incorporated during VDJ recombination. Interestingly, the translocation positions the enhancer of TCRB 70 kb downstream of the LMO-3 gene (FIG. 32C), which is comparable to its normal position relative to TCRB. Microarray expression data showed that while LMO3 is normally off in T-ALL patient samples, the gene is highly expressed in this T-ALL sample (FIG. 37). The protein family members LMO-1 and LMO-2, but not LMO3, have previously been found as oncogenic translocation partners of the TCR loci in T-ALL. Interestingly, LMO3 was recently found to act as an oncogene in neuroblastoma (14). Thus, 4C technology applied to the screening of uncharacterized patient samples for genetic aberrations led to the discovery of a previously undetected translocation and established LMO-3 as a putative new T-cell oncogene.

Conclusions

These data establish 4C technology as the first genomics approach that can identify balanced genetic abnormalities such as reciprocal translocations and inversions. In addition, it is clear that 4C technology can identify homozygous deletions and deletions associated with translocations. 4C technology may also identify heterozygous unbalanced events based on changes in captured DNA copy numbers. A major advantage of 4C technology over paired-end sequencing approaches (15) or even whole genome (high throughput) sequencing is that the identification of balanced rearrangements does not rely on capturing the single sequence fragment that carries the breakpoint; instead, 4C technology identifies balanced rearrangements based on the capture of many fragments covering several megabases across the breakpoint. For example, reciprocal translocations are identified based on the capture of many fragments locating on one part of a chromosome by a target sequence located on another chromosome. This makes the technology more robust than other approaches. The resolution of 4C technology is high and allows the immediate cloning and sequencing of the genetic breakpoints, as was demonstrated for four different rearrangements. Even breakpoints located several megabases away from the target sequence can easily be identified. The resolution is essentially identical to the average size of the fragments created by the restriction enzyme. Using an enzyme that creates smaller fragments should even further increase the resolution of this technique. 4C technology can be applied to all sorts of cell types such as blood cancer cells, solid tumors, amniocytes collected for prenatal diagnosis, etc., as long as sufficient cells can be isolated (or cultured) containing intact DNA. We currently start with about 10 million cells, but this amount can be reduced, as we hybridize PCR amplified ligation junctions originating from ~0.5 million genome equivalents. Current 4C technology requires selection of a target sequence and is therefore particularly suited for the screening for rearrangements near loci frequently involved in a disease, such as the T cell receptor genes in T-ALL or the B-cell receptor (BCR) heavy and light chain loci in human lymphomas. The technique is also very useful for the fine-mapping of poorly characterized rearrangements, for example of translocations or inversions that were found based on chromosomal karyotyping.

Example 13

Multiplex 4C-Sequencing

Experimental Design

Figure 38:
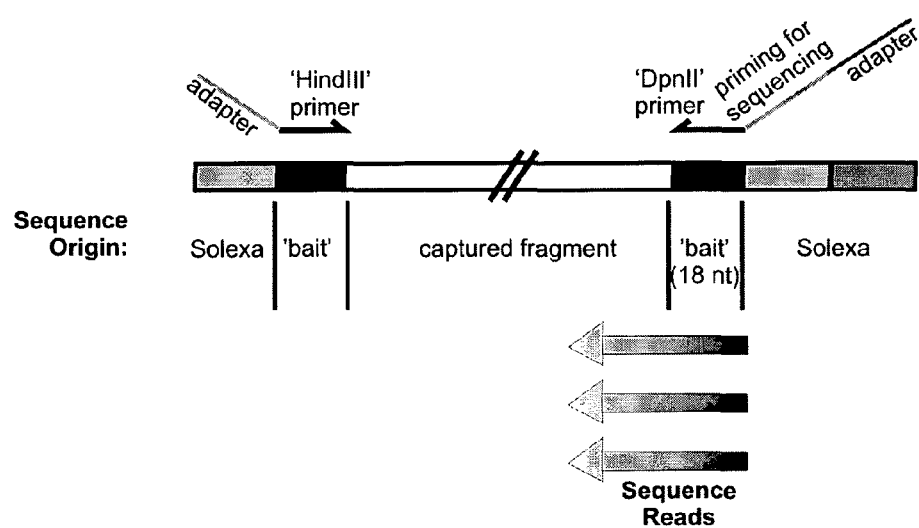

This example is based on one of several high throughput sequencing technologies (Solexa), but may be modified to fit other platforms. In order to use Solexa (Illumina) sequencing for the analysis of 4C results, sequencing is directed to the ligation junctions. Therefore, inverse PCR primers were designed for each target sequence such that they are close to the primary and secondary restriction enzyme recognition sites analysed. Here, we designed short inverse PCR primers (18-mers) that each overlap partially or completely with the primary (HindIII) and secondary (DpnII) restriction enzyme recognition sites analysed. The Solexa adapter and sequence-priming sequences were added as 5' overhangs to the inverse PCR primers (FIG. 38).

Three target sequences (baits) were selected on human chromosome 7, respectively at position 85, 105 and 139 Mb. The primer sets used to amplify the fragments captured by each of these baits are as follows:

```
85 Mb:
DpnII-primer: atgtgactcctctagatc                             (SEQ ID NO: 13)

DpnII-primer with adapter: aatgatacggcgaccaccgaa             (SEQ ID NO: 14)
cactctttccctacacgacgctcttccgatct-atgtgactcctct agatc HindIII-primer: ccctgaacctcttgaagct                          (SEQ ID NO: 15)

HindIII-primer with adapter: caagcagaagacggcatac             (SEQ ID NO: 16)
ga-ccctgaacctcttgaagct 105 Mb:
DpnII-primer: cggcctccaattgtgatc                             (SEQ ID NO: 17)

DpnII-primer with adapter: aatgatacggcgaccaccgaa             (SEQ ID NO: 18)
cactctttccctacacgacgctcttccgatct-cggcctccaattgtg atc HindIII-primer: gaattgcttttggtaagctt                         (SEQ ID NO: 19)

HindIII-primer with adapter: caagcagaagacggcatac             (SEQ ID NO: 20)
ga-gaattgcttttggtaagctt 139 Mb:
DpnII-primer: ttttagccctgacagatc                             (SEQ ID NO: 21)

DpnII-primer with adapter: aatgatacggcgaccaccgaa             (SEQ ID NO: 22)
cactctttccctacacgacgctcttccgatct-ttttagccctgacag atc HindIII-primer: agtcaaacataagcctaagc                         (SEQ ID NO: 23)

HindIII-primer with adapters: caagcagaagacggcata             (SEQ ID NO: 24)
cga-agtcaaacataagcctaagc
```

Figure 39:
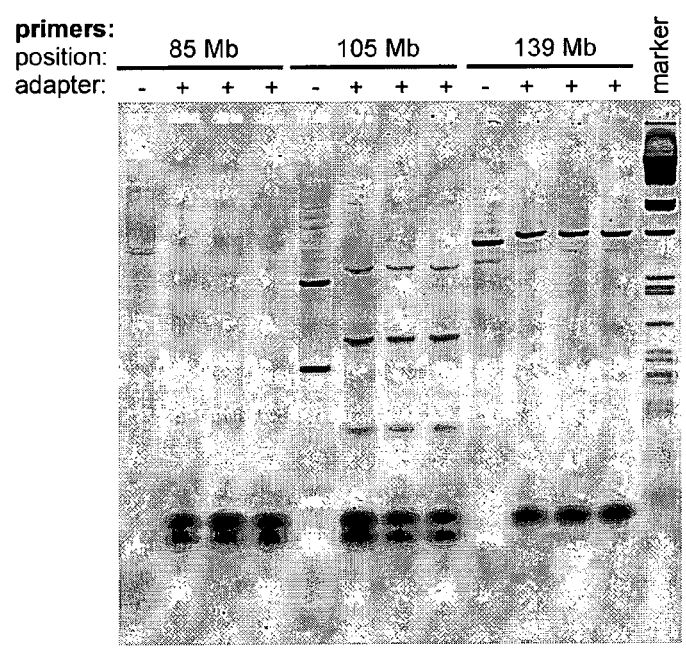

Each primer set (with adapters) was used in a separate PCR reaction; 3 PCR reactions (using 200 ng of template per reaction) were performed under standard conditions (described in Simonis et al., *Nature Methods* 2007, vol. 4, 895-901). 4C template was prepared from the HSB-2 T-ALL cell line, containing a reciprocal translocation t(1;7)(p35;q35) between the T cell receptor-beta (TCRB) locus on 7q35 and the LCK locus on 1p35 (Burnett, R. C., et al., *Blood* 84, 1232-6 (1994)). PCR products are shown in FIG. 39.

Subsequently, the PCR reactions were pooled per primer set and purified over Amersham clean up columns. The DNA concentration was measured and equal amounts of material amplified by each primer set were mixed. This mix was analysed by Solexa sequencing.

Solexa Sequencing Results

Total number of reads (one lane): $4.9*10^6$ sequences.

93% of the sequences start with one of the expected primer sequences.

When analysing the first 12 basepairs (bp) across the DpnII ligation junction and comparing these 12 basepairs to a local database containing all 12 bp genomic fragments that flank the relevant DpnII sites in the genome (ie. those directly adjacent to a HindIII site) we find that: 37% contain unique 12 bp catch, 34% contain non-unique 12 bp catch, and 29% contain no expected 12 bp catch.

Of all $4.9*106$ sequences: 34% contained primer+unique catch, 32% contained primer+non-unique-catch. In total therefore 66% contained an expected first 30 bp sequence.

Per primer set the total number of sequences and the nature of these sequences are as follows:

Primer set 1 (85 Mb):

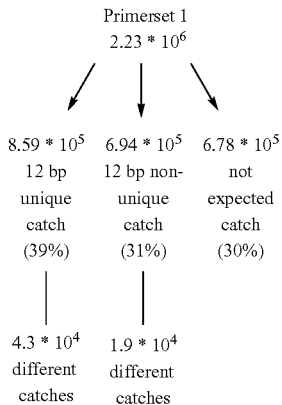

Primer set 2 (105 Mb):

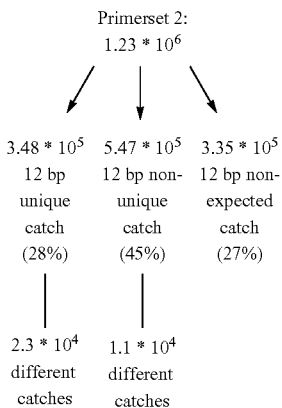

Primer set 3 (139 Mb):

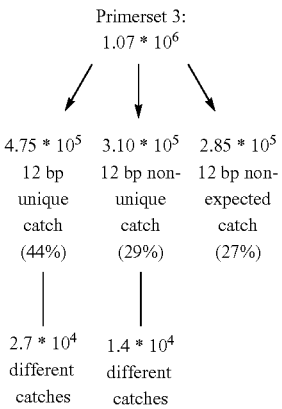

Figure 40:
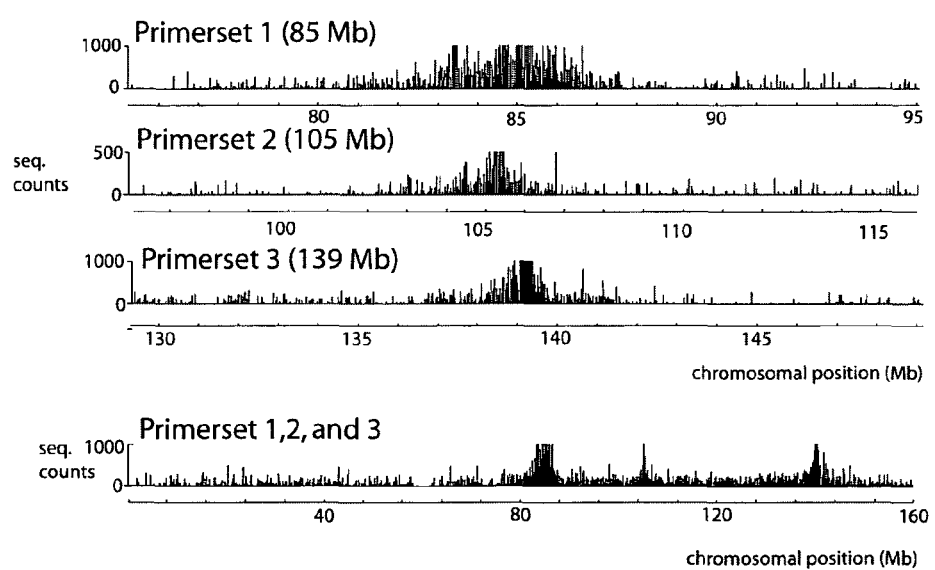
Figure 41:
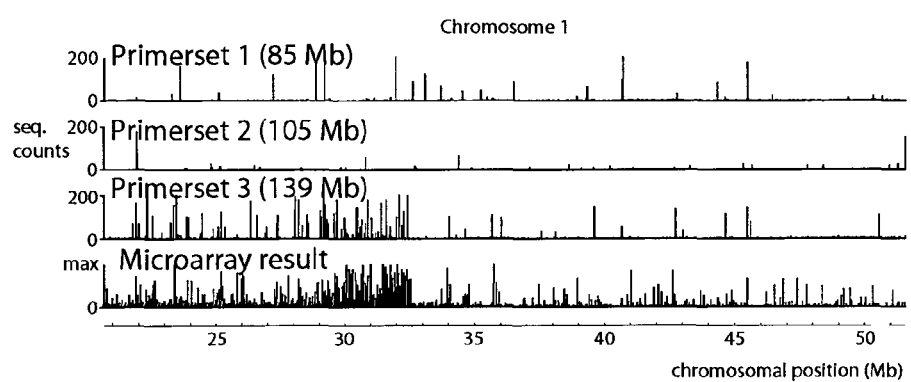
Figure 41:
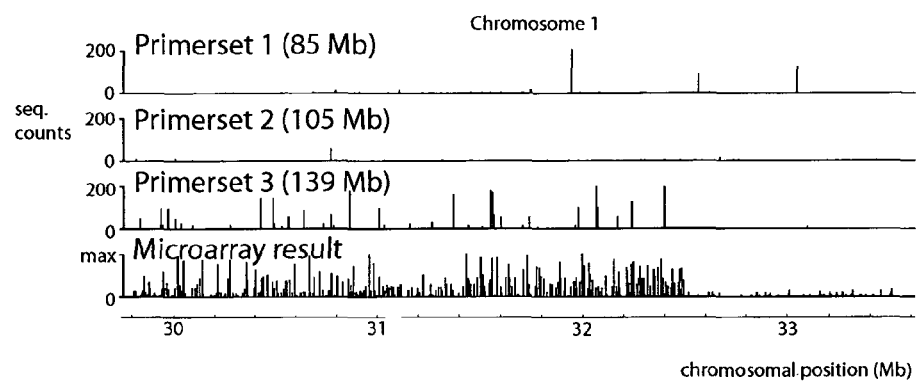

When captured sequences are plotted at their chromosomal positions, the data are shown in FIGS. 40 and 41.

In summary, the data provide a proof-of-principle for multiplex-4Sequencing. For each sequence, the bait and the captured sequence can be identified. The technique may be further improved:

1. Sequencing may be better directed to the HindIII side (instead of the DpnII side); this prevents reading random ligation events that occurred during the second ligation step.
2. Using less frequent cutters (7- or 8-cutters instead of 6-cutters) would increase the genomic distance captured (covered) by each bait.
3. Using a restriction enzyme that does not digest repetitive DNA (or is relatively under-represented in repetitive DNA) would increase the number of interpretable reads.

Further Aspects 1

1. A method for analysing the frequency of interaction of a target nucleotide sequence with one or more nucleotide sequences (eg. one or more genomic loci) comprising the use of a nucleotide sequence or an array of probes or a set of probes or an array as described herein.
2. A method for identifying one or more DNA-DNA interactions that are indicative of a particular disease state or carrier status comprising the use of a nucleotide sequence or an array of probes or a set of probes or an array as described herein.
3. A method of diagnosis or prognosis of a disease or syndrome or carrier status caused by or associated with a change in a DNA-DNA comprising the use of a nucleotide sequence or an array of probes or a set of probes or an array as described herein.
4. An assay method for identifying one or more agents that modulate a DNA-DNA interaction comprising the use of a nucleotide sequence or an array of probes or a set of probes or an array as described herein.
5. A method for detecting the location of a breakpoint (eg. a translocation) comprising the use of a nucleotide sequence or an array of probes or a set of probes or an array as described herein.
6. A method for detecting the location of an inversion comprising the use of a nucleotide sequence or an array of probes or a set of probes or an array as described herein.
7. A method for detecting the location of a deletion comprising the use of a nucleotide sequence or an array of probes or a set of probes or an array as described herein.
8. A method for detecting the location of a duplication comprising the use of a nucleotide sequence or an array of probes or a set of probes or an array as described herein.

9. A method for analysing the frequency of interaction of a target nucleotide sequence with one or more nucleotide sequences of interest (eg. one or more genomic loci) comprising the steps of:
(a) providing a sample of cross-linked DNA;
(b) digesting the cross-linked DNA with a primary restriction enzyme;
(c) ligating the cross-linked nucleotide sequences;
(d) reversing the cross linking;
(e) optionally digesting the nucleotide sequences with a secondary restriction enzyme;
(f) optionally ligating the nucleotide sequences;
(g) amplifying the one or more nucleotide sequences of interest that are ligated to the target nucleotide sequence using at least two oligonucleotide primers, wherein each primer hybridises to a known DNA sequence that flanks the nucleotide sequences of interest;
(h) hybridising the amplified sequence(s) to an array or sequencing the amplified sequences; and
(i) determining the frequency of interaction between the DNA sequences.

Further Aspects 2

Still further aspects of the present invention are set forth below in the numbered paragraphs.

1. A circularised nucleotide sequence comprising a first and a second nucleotide sequence separated by primary restriction enzyme recognition sites, wherein said first nucleotide sequence is a target nucleotide sequence and said second nucleotide sequence is obtainable by cross-linking genomic DNA.
2. The circularised nucleotide sequence according to paragraph 1, wherein the target nucleotide sequence is selected from the group consisting of a promoter, an enhancer, a silencer, an insulator, a matrix attachment region, a locus control region, a transcription unit, an origin of replication, a recombination hotspot, a translocation breakpoint, a centromere, a telomere, a gene-dense region, a gene-poor region, a repetitive element and a (viral) integration site.
3. The circularised nucleotide sequence according to paragraph 1, wherein the target nucleotide sequence is a nucleotide sequence that is associated with or causes a disease, or is located less then 15 Mb on a linear DNA template from a locus that is associated with or causes a disease.
4. The circularised nucleotide sequence according to any of paragraphs 1-3, wherein the target nucleotide sequence is selected from the group consisting of: AML1, MLL, MYC, BCL, BCR, ABL1, IGH, LYL1, TAL1, TAL2, LMO2, TCR α/δ, TCRβ and HOX or other loci associated with disease as described in "Catalogue of Unbalanced Chromosome Aberrations in Man" 2nd edition. Albert Schinzel. Berlin: Walter de Gruyter, 2001. ISBN 3-11-011607-3.
5. The circularised nucleotide sequence according to any of paragraphs 1-4 wherein the primary restriction enzyme recognition site is a 6-8 bp recognition site, preferably selected from the group consisting of BglII, HindIII, EcoRI, BamHI, SpeI, PstI and NdeI.
6. The circularised nucleotide sequence according to any of the preceding paragraphs, wherein the secondary restriction enzyme recognition site is a 4 or 5 bp nucleotide sequence recognition site.
7. The circularised nucleotide sequence according to any of the preceding paragraphs, wherein the secondary restriction enzyme recognition site is located at greater than about 350 bp from the primary restriction site.
8. The circularised nucleotide sequence according to any of the preceding paragraphs, wherein the nucleotide sequence is labelled.

9. A method for preparing a circularised nucleotide sequence comprising the steps of:
(a) providing a sample of cross-linked DNA;
(b) digesting the cross-linked DNA with a primary restriction enzyme;
(c) ligating the cross-linked nucleotide sequences for circularisation;
10. A method according to paragraph 9, wherein the cross-linked nucleotide sequence is amplified using. PCR.
11. A method according to paragraph 10, wherein the cross-linked nucleotide sequence is amplified using inverse PCR.
12. A method according to paragraph 10 or paragraph 11, wherein the Expand Long Template PCR System (Roche) is used.

TABLE 2

| Interaction | in 4C | N | % over-lapping | in Cryo-FISH | P value |
|---|---|---|---|---|---|
| B-globin - Chr.7 73.1 Mb | + | 258 | 7.4 | + | P < 0.001 |
| B-globin - Chr.7 80.1 Mb (OR) | − | 254 | 3.6 | − | |
| B-globin - Chr.7 118.3 Mb | − | 255 | 3.5 | − | |
| B-globin - Chr.7 127.9 Mb (Uros) | + | 259 | 6.6 | + | P < 0.001 |
| B-globin - Chr.7 130.1 Mb | + | 413 | 9.7 | + | P < 0.001 |
| B-globin - Chr.7 135.0 Mb (OR) | − | 261 | 1.9 | − | |
| B-globin - D7Mit21 | x | 258 | 0.4 | − | |
| Chr.7 80.1 Mb - Chr.7 135.0 Mb | x | 253 | 5.9 | + | P < 0.05 |
| Chr.7 73.1 Mb - Chr.7 130.1 Mb | x | 254 | 5.5 | + | P < 0.05 |
| Rad23A - Chr. 8 21.8 Mb | + | 255 | 5.9 | + | P < 0.05 |
| Rad23A - Chr. 8 122.4 Mb | + | 261 | 8 | + | P < 0.001 |
| B-globin - Chr.7 73.1 Mb | − | 256 | 3.9 | − | |
| B-globin - Chr.7 80.1 Mb (OR) | + | 256 | 12.9 | + | P < 0.001 |
| B-globin - Chr.7 118.3 Mb | − | 242 | 4.1 | − | |
| B-globin - Chr.7 130.1 Mb | − | 263 | 3 | − | |
| B-globin - Chr.7 135.0 Mb (OR) | + | 256 | 7 | + | P < 0.05 |
| B-globin - D7Mit21 | | 258 | 6.2 | + | P < 0.05 |
| Chr.7 80.1 Mb - Chr.7 135 Mb | | 261 | 5 | + | P < 0.1 |
| Rad23A - Chr. 8 21.8 Mb | − | 260 | 3.8 | − | |
| Rad23A - Chr. 8 122.3 Mb | + | 258 | 8.1 | + | P < 0.001 |

REFERENCES

Blanton J, Gaszner M, Schedl P. 2003. Protein:protein interactions and the pairing of boundary elements in vivo. Genes Dev 17:664-75.

Dekker, J., Rippe, K., Dekker, M., and Kleckner, N. 2002. Capturing chromosome conformation. Science 295: 1306-11.

Drissen R, Palstra R J, Gillemans N, Splinter E, Grosveld F, Philipsen S, de Laat W. 2004. The active spatial organization of the beta-globin locus requires the transcription factor EKLF. Genes Dev 18:2485-90.

Horike S, Cai S, Miyano M, Cheng J F, Kohwi-Shigematsu T. 2005. Loss of silent-chromatin looping and impaired imprinting of DLX5 in Rett syndrome. Nat Genet 37:31-40.

Murrell A, Heeson S, Reik W. 2004. Interaction between differentially methylated regions partitions the imprinted genes Igf2 and H19 into parent-specific chromatin loops. Nat Genet 36:889-93.

Palstra, R. J., Tolhuis, B., Splinter, E., Nijmeijer, R., Grosveld, F., and de Laat, W. 2003. The beta-globin nuclear compartment in development and erythroid differentiation. Nat Genet 35: 190-4.

Patrinos, G. P., de Krom, M., de Boer, E., Langeveld, A., Imam, A. M. A, Strouboulis, J., de Laat, W., and Grosveld, F. G. (2004). Multiple interactions between regulatory regions are required to stabilize an active chromatin hub. Genes & Dev. 18: 1495-1509.

Spilianakis C G, Flavell R A. 2004. Long-range intrachromosomal interactions in the T helper type 2 cytokine locus. Nat Immunol 5:1017-27.

Tolhuis, B., Palstra, R. J., Splinter, E., Grosveld, F., and de Laat, W. 2002. Looping and interaction between hypersensitive sites in the active beta-globin locus. Molecular Cell 10: 1453-65.

Vakoc C R, Letting D L, Gheldof N, Sawado T, Bender M A, Groudine M, Weiss M J,

Dekker J, Blobel G A. 2005. Proximity among distant regulatory elements at the beta-globin locus requires GATA-1 and FOG-1. Mol Cell. 17:453-62

REFERENCES FOR EXAMPLE 12

1. *Nature* 447, 661 (Jun. 7, 2007).
2. D. F. Easton et al., *Nature* 447, 1087 (Jun. 28, 2007).
3. L. Feuk, A. R. Carson, S. W. Scherer, *Nat Rev Genet* 7, 85 (February 2006).
4. A. J. Sharp, Z. Cheng, E. E. Eichler, *Annu Rev Genomics Hum Genet* 7, 407 (2006).
5. A. J. Iafrate et al., *Nat Genet* 36, 949 (September 2004).
6. M. R. Mehan, N. B. Freimer, R. A. Ophoff, *Hum Genomics* 1, 335 (August 2004).
7. E. E. Eichler et al., *Nature* 447, 161 (May 10, 2007).
8. M. Simonis et al., *Nat Genet* 38, 1348 (November 2006).
9. K. Rippe, *Trends Biochem Sci* 26, 733 (December 2001).
10. R. C. Burnett, M. J. Thirman, J. D. Rowley, M. O. Diaz, *Blood* 84, 1232 (Aug. 15, 1994).
11. F. Speleman et al., *Leukemia* 19, 358 (March 2005).
12. J. Soulier et al., *Blood* 106, 274 (Jul. 1, 2005).
13. R. J. Galjaard et al., *Am J Med Genet A* 121, 168 (Aug. 30, 2003).
14. M. Aoyama et al., *Cancer Res* 65, 4587 (Jun. 1, 2005).
15. E. Tuzun et al., *Nat Genet* 37, 727 (July, 2005).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for analysing the frequency of interaction of two or more target nucleotide sequences with one or more nucleotide sequences of interest comprising the steps of:
   (a) providing a sample of cross-linked DNA;
   (b) digesting the cross-linked DNA with a primary restriction enzyme;
   (c) ligating the cross-linked nucleotide sequences, wherein the ligation reaction results in the formation of DNA circles;
   (d) reversing the cross linking;
   (e) optionally digesting the nucleotide sequences with a secondary restriction enzyme;
   (f) ligating one or more DNA sequences of known nucleotide composition to the available secondary restriction enzyme digestion site(s) that flank the one or more nucleotide sequences of interest wherein the ligation reaction results in the formation of DNA circles;
   (g) amplifying the one or more nucleotide sequences of interest using at least two oligonucleotide primers, wherein each primer hybridises to the DNA sequences that flank the nucleotide sequences of interest using multiplex PCR;
   (h) hybridising the amplified sequence(s) to an array; and
   (i) determining the frequency of interaction between the DNA sequences.

2. The method according to claim 1 where step (u) comprises the analysis of ligation products between target sequences and cross-linked sequences of interest by means of sequencing.

3. The method according to claim 1, further comprising pooling of some or all of the PCR products obtained for each of the target sequences in step (g) and subsequent simultaneous analysis of their DNA interactions.

4. The method according to claim 3, further comprising wherein two or more amplified sequences are differentially labelled prior to pooling and analysis by hybridisation to an array.

5. The method according to claim 3, further comprising wherein two or more amplified sequences are identically labelled and analysed by hybridisation to an array when the sequences reside on different chromosomes.

6. The method according to claim 3, further comprising wherein two or more amplified sequences are identically labelled when the sequences reside on the same chromosome at a distance that is for enough for minimal overlap between DNA-DNA interaction signals.

7. The method according to claim 1, wherein high throughput sequencing is used to analyse the ligation junctions formed between target sequences and captured sequences of interest.

8. The method according to claim 7, wherein sequencing is directed to the ligation junctions formed between target sequences and captured sequences of interest by the addition of adapter sequences required for sequencing to the ends of the amplified sequences.

9. The method according to claim 8, wherein sequencing is directed to the ligation junctions formed between target sequences and captured sequences of interest by the addition of the complete, or part of the, adapter sequences required for sequencing as 5' overhangs to the oligonucleotide primers used to amplify the one or more nucleotide sequences of interest.

10. The method according, to claim 8, wherein sequencing is directed to the ligation junctions formed between target sequences and captured sequences of interest by the conjugation of a biotin substance or other moiety to the oligonucleotide primers used to amplify the one or more nucleotide sequences of interest, followed by streptavidin or otherwise mediated purification of the PCR amplified material.

11. The method according to claim 7, wherein sequencing is directed to the ligation junctions between target sequences and captured sequences of interest by designing the oligonucleotide primers used to amplify the one or more nucleotide sequences of interest within 400, 300, 200, 150, 100, 90, 80 70, 60, 50, 40, 30, 20, 10, 9, 8, 7, 6, 5, 4, 3, 2, 1 nucleotides from the primary and/or secondary restriction enzyme recognition site(s) analysed.

12. The method according to claim 7, wherein sequencing is directed to the ligation junctions between target sequences and captured sequences of interest by designing the oligonucleotide primers used to amplify the one or more nucleotide sequences of interest such that they partially or completely overlap with the primary and/or secondary restriction enzyme recognition site analysed.

13. The method according to claim 7, wherein sequences are read across the ligation junction such that when multiplexed or pooled PCR samples are analysed, sufficient sequence information is obtained on either side of the ligation junction to unambiguously identify each target sequence and each captured sequence of interest.

14. The method according to claim 1, wherein the target nucleotide sequence is selected from the group consisting of a genomic rearrangement, promoter, an enhancer, a silencer, an insulator, a matrix attachment region, a locus control region, a transcription unit, an origin of replication a recombination hotspot, a translocation breakpoint, a centromere, a telomere, a gene-dense region, a gene-poor region, a repetitive element and a integration site.

15. The method according to claim 1, wherein the target nucleotide sequence is a nucleotide sequence that is associated with or causes a disease, or is located up to or greater than 15 Mb on a linear DNA template from a locus that is associated with or causes a disease.

16. The method according to claim 1, wherein the target nucleotide sequence is selected from the group consisting of: AML1, MLL, MYC, BCL, BCR, ABL1, IGH, LYL1, TAL1, TAL2, LMO2, TCRα/δ, TCRβ and HOX or other loci associated with disease.

17. The method according to claim 1, wherein the target sequences are distributed along the linear genome template such that the interacting sequences cover an entire chromosome or the genome.

18. The method according to claim wherein the primary restriction enzyme is a restriction enzyme that recognises a 6-8 bp recognition site.

19. The method according to claim 18, wherein the primary restriction enzyme is selected from the group consisting of BglII, HindIII, EcoRI, BamHI, SpeI, PstI and NdeI.

20. The method according to claim 18, wherein the primary restriction enzyme is selected based on its absence from, or under representation in repetitive sequences.

21. The method according to claim 1, wherein the secondary restriction enzyme is of restriction enzyme that recognises a 4 or 5 bp nucleotide sequence recognition site.

22. The method according to claim 1, wherein the secondary restriction enzyme recognition site is located at greater than 350 bp from the primary restriction site in the target nucleotide sequence.

23. A method for analysing the frequency of interaction of a target nucleotide sequence with one or more DNA sequences comprising the steps of:
  (a) providing a sample of cross-linked DNA;
  (b) digesting the cross-linked DNA with a primary restriction enzyme;
  (c) ligating the cross-linked DNA sequences;
  (d) reversing the cross linking;
  (e) optionally digesting the DNA sequences with a secondary restriction enzyme;
  circularising the nucleotide sequences;
  (g) amplifying one or more DNA sequences obtained in step (f) that are ligated to the target nucleotide sequence;
  (h) optionally hybridising the amplified sequences to an array or analysing the amplified sequences by sequencing; and
  (i) determining the frequency of interaction between the DNA sequences.

24. A method for identifying the frequency of interaction of two or more target nucleotide sequences with one or more nucleotide sequences of interest that are indicative of a particular disease state comprising the step of performing steps (a)-(i) of claim 1, wherein in step (a) a sample of cross-linked DNA is provided from a diseased and a non-diseased cell, and wherein a difference between the frequency of interaction of two or more target nucleotide sequences with one or more nucleotide sequences of interest from the diseased and non-diseased cells indicates a difference in the linear organisation of the chromosome templates, which is indicative of a particular trait or disease state.

25. A method of diagnosis or prognosis of a disease or syndrome caused by or associated with a change in the frequency of interaction of two or more target nucleotide sequences with one or more nucleotide sequences of interest comprising the step of performing steps (a)-(i) of claim 1, wherein step (a) comprises providing a sample of cross-linked DNA from a subject; and wherein step (i) comprises comparing the frequency of interaction of two or more target nucleotide sequences with one or more nucleotide sequences of interest in the subject with that of an unaffected control; wherein a difference between the value obtained from the control and the value obtained from the subject is indicative that the subject is suffering from the disease or syndrome or is indicative that the subject will suffer from the disease or syndrome.

26. The method according to claim 25, wherein a transition from low to high interaction frequencies is indicative of the location of a balanced and/or unbalanced genetic rearrangement.

27. The method according to 25, wherein an inversed pattern of the frequency of interaction of two or more target nucleotide sequences with one or more nucleotide sequences of interest for the subject sample as compared to the control is indicative of a balanced and/or unbalanced inversion.

28. The method according to claim 25, wherein a reduction in the frequency of interaction of two or more target nucleotide sequences with one or more nucleotide sequences of interest for the subject sample as compared to the control, in combination with an increase in the frequency of interaction of two or more target nucleotide sequences with one or more nucleotide sequences of interest for more distant regions, is indicative of a balanced and/or unbalanced deletion.

29. The method according to claim 25, wherein an increase or a decrease in the frequency of interaction of two or more target nucleotide sequences with one or more nucleotide sequences of interest for the subject sample as compared to the control is indicative of a balanced and/or unbalanced duplication or insertion.

30. A method according to claim 25, wherein spectral karyotyping and/or FISH is used prior to performing said method.

31. The method according to claim 25, wherein the disease is a genetic disease.

32. The method according to claim 25, wherein the disease is cancer.

33. A method of diagnosis or prognosis of a disease or syndrome caused by or associated with a change in the frequency of interaction of two or more target nucleotide sequences with one or more nucleotide sequences of interest comprising the step of: performing steps (a)-(i) of claim 1, wherein step (a) comprises providing a sample of cross-linked DNA from a subject; and wherein said method comprises the additional step of: (j) identifying one or more loci that have undergone a genomic rearrangement that is associated with a disease.

34. An assay method for identifying, one or more agents that modulate the frequency of interaction of two or more target nucleotide sequences with one or more nucleotide sequences of interest comprising the steps of:
  (a) contacting a sample with one or more agents; and
  (b) performing steps (a) to (i) of claim 1, wherein step (a) comprises providing cross-linked DNA from the sample;
  wherein a difference between (i) the frequency of interaction between the DNA sequences in the presence of the agent and (ii) the frequency of interaction between the DNA sequences in the absence of the agent is indicative of an agent that modulates the frequency of interaction of two or more target nucleotide sequences with one or more nucleotide sequences of interest.

35. A method for detecting the location of a balanced and/or unbalanced rearrangement (eg. a translocation) comprising the step of:
(a) performing steps (a) to (i) of claim 1; and
(b) comparing the frequency of interaction of two or more target nucleotide sequences with one or more nucleotide sequences of interest with that of a control;
wherein a transition from low to high frequency of interaction of two or more target nucleotide sequences with one or more nucleotide sequences of interest in the sample as compared to the control is indicative of the location of a breakpoint.

36. A method for detecting the location of a balanced and/or unbalanced inversion comprising the steps of:
(a) performing steps (a) to (i) of claim 1; and
(b) comparing the frequency of interaction of two or more target nucleotide sequences with one or more nucleotide sequences of interest with that of a control;
wherein an inversed pattern of frequency of interaction of two or more target nucleotide sequences with one or more nucleotide sequences of interest for the sample as compared to the control is indicative of an inversion.

37. A method for detecting the location of a deletion comprising the steps of:
(a) performing steps (a) to (i) of claim 1; and
(b) comparing the frequency of interaction of two or more target nucleotide sequences with one or more nucleotide sequences of interest between the DNA sequences with that of a control;
wherein a reduction in the frequency of interaction of two or more target nucleotide sequences with one or more nucleotide sequences of interest for the sample as compared to the control is indicative of deletion.

38. A method for detecting the location of a duplication comprising the steps of:
(a) performing steps (a) to (i) of claim 1; and
(b) comparing the frequency of interaction of two or more target nucleotide sequences with one or more nucleotide sequences of interest with that of a control;
wherein an increase in the frequency of interaction of two or more target nucleotide sequences with one or more nucleotide sequences of interest for the subject sample as compared to the control is indicative of a duplication or insertion.

39. A method according to claim 1, wherein nucleotide sequences interacting with two or more target sequences are amplified.

40. A method according to claim 39, wherein the target sequences are positioned at or near genomic loci known to be associated with a diseased state.

41. A method according to claim 40, wherein the target sequences are selected without prior knowledge on the location of a rearrangement and are spaced such that the interacting sequences cover an entire chromosome or the genome, and wherein the identified interacting sequences allow reconstructing linear chromosome maps and genomic rearrangements that occurred within and between chromosomes.

42. A method according to claim 39, wherein the amplified sequences are labelled.

43. A method according to claim 42, wherein the amplified sequences are differentially labelled according to their position in the genome.

44. A method according to claim 39, for the detection of a balanced and/or unbalanced rearrangement, translocation, inversion, deletion, duplication or insertion.

45. A method for analysing the frequency of interaction of two or more target nucleotide sequences with one or more nucleotide sequences of interest comprising the steps of:
(a) providing a sample of cross-linked DNA;
(b) digesting the cross-linked DNA with a primary restriction enzyme;
(c) ligating the cross-linked nucleotide sequences, wherein the ligation reaction results in the formation of DNA circles;
(d) reversing the cross linking; and
(e) sequencing the ligated nucleotide sequences.

46. A method for determining the presence of a genomic rearrangement in a sample by determining the frequency of interaction of two or more target nucleotide sequences with one or more nucleotide sequences of interest comprising the steps of:
(a) providing a sample of nucleic acid, wherein said nucleic acid comprises a nucleotide sequence of known sequence adjacent to the location of the suspected genomic rearrangement;
(b) digesting the DNA with a primary restriction enzyme to form a plurality of restriction fragments;
(c) optionally, purifying the restriction fragments;
(d) ligating the restriction fragments to form circularised DNA;
(e) optionally, purifying the circularised DNA;
(f) digesting the circularised DNA with a secondary restriction enzyme to form a plurality of restriction fragments;
(g) ligating the restriction fragments to form circularised DNA;
(h) amplifying the suspected genomic rearrangement using one or more primers that hybridise to the nucleotide sequence of known sequence; and
(i) sequencing the suspected genomic rearrangement.

47. A method according to claim 1, wherein the array hybridisation step is replaced with a sequencing step.

48. A method according to claim 45, wherein both the target nucleotide sequence and the nucleotide sequence of interest are identified by sequencing.

49. A method according to claim 45, wherein adapter sequences are ligated to the PCR products.

* * * * *

UNITED STATES PATENT AND TRADEMARK OFFICE
CERTIFICATE OF CORRECTION

PATENT NO. : 8,642,295 B2  
APPLICATION NO. : 12/522555  
DATED : February 4, 2014  
INVENTOR(S) : Wouter De Laat et al.

Page 1 of 1

It is certified that error appears in the above-identified patent and that said Letters Patent is hereby corrected as shown below:

In the Claims:

Col. 93, Line 43, Claim 2:
DELETE after step "(u)"
ADD after step --(h)--

Col. 93, Line 62, Claim 6:
DELETE after is "for"
ADD after is --far--

Col. 94, Line 64, Claim 14:
DELETE after and "a"
ADD after and --an--

Col. 95, Line 13, Claim 18:
ADD after claim --1--

Col. 95, Line 39, Claim 23:
ADD before circularizing --(f)--

Signed and Sealed this
Sixth Day of May, 2014

Michelle K. Lee
*Deputy Director of the United States Patent and Trademark Office*

SEQUENCE LISTING

```
<160> NUMBER OF SEQ ID NOS: 32

<210> SEQ ID NO 1
<211> LENGTH: 22
<212> TYPE: DNA
<213> ORGANISM: Artificial
<220> FEATURE:
<223> OTHER INFORMATION: Oligonucleotide primer

<400> SEQUENCE: 1
acttcctaca cattaacgag cc                                                  22

<210> SEQ ID NO 2
<211> LENGTH: 23
<212> TYPE: DNA
<213> ORGANISM: Artificial
<220> FEATURE:
<223> OTHER INFORMATION: Oligonucleotide primer

<400> SEQUENCE: 2
gctgttatcc ctttctcttc tac                                                 23

<210> SEQ ID NO 3
<211> LENGTH: 18
<212> TYPE: DNA
<213> ORGANISM: Artificial
<220> FEATURE:
<223> OTHER INFORMATION: Oligonucleotide primer

<400> SEQUENCE: 3
tcacacgcga agtaggcc                                                       18

<210> SEQ ID NO 4
<211> LENGTH: 19
<212> TYPE: DNA
<213> ORGANISM: Artificial
<220> FEATURE:
<223> OTHER INFORMATION: Oligonucleotide primer
```

-continued

```
<400> SEQUENCE: 4
ccttcctcca ccatgatga                                                     19

<210> SEQ ID NO 5
<211> LENGTH: 25
<212> TYPE: DNA
<213> ORGANISM: Artificial
<220> FEATURE:
<223> OTHER INFORMATION: Oligonucleotide primer

<400> SEQUENCE: 5
aacgcatttg ctcaatcaac tactg                                              25

<210> SEQ ID NO 6
<211> LENGTH: 25
<212> TYPE: DNA
<213> ORGANISM: Artificial
<220> FEATURE:
<223> OTHER INFORMATION: Oligonucleotide primer

<400> SEQUENCE: 6
gttgctcctc acatttgctt ctgac                                              25

<210> SEQ ID NO 7
<211> LENGTH: 41
<212> TYPE: DNA
<213> ORGANISM: Artificial
<220> FEATURE:
<223> OTHER INFORMATION: Oligonucleotide primer

<400> SEQUENCE: 7
catgaagaaa cgagcacccc cttgatgttt ctccctttac c                            41

<210> SEQ ID NO 8
<211> LENGTH: 40
<212> TYPE: DNA
<213> ORGANISM: Artificial
<220> FEATURE:
<223> OTHER INFORMATION: Oligonucleotide primer

<400> SEQUENCE: 8
tgtcaggctc ttctcctaca cgtcgtccag aacactcacc                              40

<210> SEQ ID NO 9
<211> LENGTH: 37
<212> TYPE: DNA
<213> ORGANISM: Artificial
<220> FEATURE:
<223> OTHER INFORMATION: Oligonucleotide primer

<400> SEQUENCE: 9
aatccagggc tacttccagc cgtgatgcta tctgcca                                 37

<210> SEQ ID NO 10
<211> LENGTH: 38
<212> TYPE: DNA
<213> ORGANISM: Artificial
<220> FEATURE:
<223> OTHER INFORMATION: Oligonucleotide primer

<400> SEQUENCE: 10
tgttggaaga ccaggtgaag tgtcgtggaa agcgagtg                                38

<210> SEQ ID NO 11
<211> LENGTH: 45
<212> TYPE: DNA
```

<213> ORGANISM: Artificial
<220> FEATURE:
<223> OTHER INFORMATION: Oligonucleotide primer

<400> SEQUENCE: 11
caatcccaga tacattcctc atacaaatac tttccaagac tggac                45

<210> SEQ ID NO 12
<211> LENGTH: 39
<212> TYPE: DNA
<213> ORGANISM: Artificial
<220> FEATURE:
<223> OTHER INFORMATION: Oligonucleotide primer

<400> SEQUENCE: 12
gaatatgtta tgcttgatcc ttccatgaga gaagtctag                       39

<210> SEQ ID NO 13
<211> LENGTH: 18
<212> TYPE: DNA
<213> ORGANISM: Artificial
<220> FEATURE:
<223> OTHER INFORMATION: Oligonucleotide primer

<400> SEQUENCE: 13
atgtgactcc tctagatc                                              18

<210> SEQ ID NO 14
<211> LENGTH: 71
<212> TYPE: DNA
<213> ORGANISM: Artificial
<220> FEATURE:
<223> OTHER INFORMATION: Oligonucleotide primer

<400> SEQUENCE: 14
aatgatacgg cgaccaccga acactctttc cctacacgac gctcttccga tctatgtgac    60
tcctctagat c                                                        71

<210> SEQ ID NO 15
<211> LENGTH: 19
<212> TYPE: DNA
<213> ORGANISM: Artificial
<220> FEATURE:
<223> OTHER INFORMATION: Oligonucleotide primer

<400> SEQUENCE: 15
ccctgaacct cttgaagct                                             19

<210> SEQ ID NO 16
<211> LENGTH: 40
<212> TYPE: DNA
<213> ORGANISM: Artificial
<220> FEATURE:
<223> OTHER INFORMATION: Oligonucleotide primer

<400> SEQUENCE: 16
caagcagaag acggcatacg accctgaacc tcttgaagct                      40

<210> SEQ ID NO 17
<211> LENGTH: 18
<212> TYPE: DNA
<213> ORGANISM: Artificial
<220> FEATURE:
<223> OTHER INFORMATION: Oligonucleotide primer

<400> SEQUENCE: 17
cggcctccaa ttgtgatc      18

<210> SEQ ID NO 18
<211> LENGTH: 71
<212> TYPE: DNA
<213> ORGANISM: Artificial
<220> FEATURE:
<223> OTHER INFORMATION: Oligonucleotide primer

<400> SEQUENCE: 18
aatgatacgg cgaccaccga acactctttc cctacacgac gctcttccga tctcggcctc      60
caattgtgat c      71

<210> SEQ ID NO 19
<211> LENGTH: 20
<212> TYPE: DNA
<213> ORGANISM: Artificial
<220> FEATURE:
<223> OTHER INFORMATION: Oligonucleotide primer

<400> SEQUENCE: 19
gaattgcttt tggtaagctt      20

<210> SEQ ID NO 20
<211> LENGTH: 41
<212> TYPE: DNA
<213> ORGANISM: Artificial
<220> FEATURE:
<223> OTHER INFORMATION: Oligonucleotide primer

<400> SEQUENCE: 20
caagcagaag acggcatacg agaattgctt ttggtaagct t      41

<210> SEQ ID NO 21
<211> LENGTH: 18
<212> TYPE: DNA
<213> ORGANISM: Artificial
<220> FEATURE:
<223> OTHER INFORMATION: Oligonucleotide primer

<400> SEQUENCE: 21
ttttagccct gacagatc      18

<210> SEQ ID NO 22
<211> LENGTH: 71
<212> TYPE: DNA
<213> ORGANISM: Artificial
<220> FEATURE:
<223> OTHER INFORMATION: Oligonucleotide primer

<400> SEQUENCE: 22
aatgatacgg cgaccaccga acactctttc cctacacgac gctcttccga tcttttagc      60 cctgacagat c      71

<210> SEQ ID NO 23
<211> LENGTH: 20
<212> TYPE: DNA
<213> ORGANISM: Artificial
<220> FEATURE:
<223> OTHER INFORMATION: Oligonucleotide primer

<400> SEQUENCE: 23
agtcaaacat aagcctaagc      20

<210> SEQ ID NO 24

-continued

```
<211> LENGTH: 41
<212> TYPE: DNA
<213> ORGANISM: Artificial
<220> FEATURE:
<223> OTHER INFORMATION: Oligonucleotide primer

<400> SEQUENCE: 24
caagcagaag acggcatacg aagtcaaaca taagcctaag c                 41

<210> SEQ ID NO 25
<211> LENGTH: 157
<212> TYPE: DNA
<213> ORGANISM: Homo sapiens

<400> SEQUENCE: 25
aaggaaaccc catgcccata agacgtcact aatttctgaa ctcttgtttt ttttttttt    60 ttttcaagta gttctcatct aagtagttgt tttttgtcat gagaaaatca gatatgttgc  120
taaaaattca caactattgc aagaaaaaat aaaagac                           157

<210> SEQ ID NO 26
<211> LENGTH: 100
<212> TYPE: DNA
<213> ORGANISM: Homo sapiens

<400> SEQUENCE: 26
ctccaatgta actgtggatt acacctaaaa gagccagaaa acacagactc tctgtggaac    60
catgacacaa cagtgcttgg tattattttt tcctagttag                         100

<210> SEQ ID NO 27
<211> LENGTH: 60
<212> TYPE: DNA
<213> ORGANISM: Homo sapiens

<400> SEQUENCE: 27
aagagccaga aaacacagac tctctgtgga accatgacac aacagtgctt ggtattattt    60

<210> SEQ ID NO 28
<211> LENGTH: 50
<212> TYPE: DNA
<213> ORGANISM: Homo sapiens

<400> SEQUENCE: 28 aaacccatg cccataagac gtcactaatt tctgaactct tgttttttt               50

<210> SEQ ID NO 29
<211> LENGTH: 45
<212> TYPE: DNA
<213> ORGANISM: Homo sapiens

<400> SEQUENCE: 29
cgaagaactg ctcattgtag gtcaagtttc aaggtcttga accac                    45

<210> SEQ ID NO 30
<211> LENGTH: 52
<212> TYPE: DNA
<213> ORGANISM: Homo sapiens

<400> SEQUENCE: 30
tctgtgccag cagcttgtgc cgcgagccgg ccgatactct gcctaggact cc            52

<210> SEQ ID NO 31
<211> LENGTH: 30
<212> TYPE: DNA
```

```
<213> ORGANISM: Homo sapiens

<400> SEQUENCE: 31
gaccagggca ttggatttat ttcagagatc                                      30

<210> SEQ ID NO 32
<211> LENGTH: 26
<212> TYPE: DNA
<213> ORGANISM: Homo sapiens

<400> SEQUENCE: 32
gatcctgaca ccttagagct aagctt                                          26
```